United States Patent
Van Tilburg et al.

(10) Patent No.: US 7,084,127 B2
(45) Date of Patent: Aug. 1, 2006

(54) C2,5'-DISUBSTITUTED AND $N^6$, C2,5'-TRISUBSTITUTED ADENOSINE DERIVATIVES AND THEIR DIFFERENT USES

(75) Inventors: Erica Van Tilburg, Amsterdam (NL); Ad Ijzerman, Haarlem (NL)

(73) Assignees: Universiteit Leiden (NL); Can-Fite Biopharma Ltd. (IL)

( * ) Notice: Subject to any disclaimer, the term of this patent is extended or adjusted under 35 U.S.C. 154(b) by 0 days.

(21) Appl. No.: 10/469,735

(22) PCT Filed: Mar. 3, 2002

(86) PCT No.: PCT/IL02/00160

§ 371 (c)(1),
(2), (4) Date: Mar. 4, 2004

(87) PCT Pub. No.: WO02/070532

PCT Pub. Date: Sep. 12, 2002

(65) Prior Publication Data

US 2004/0132686 A1 Jul. 8, 2004

(30) Foreign Application Priority Data

Mar. 3, 2001 (GB) .................................. 0105337.0

(51) Int. Cl.
*A61K 31/70* (2006.01)
*C07H 19/167* (2006.01)
(52) U.S. Cl. .................... 514/46; 536/27.3; 536/27.62; 536/27.63
(58) Field of Classification Search .................. 514/46; 536/27.3, 27.62, 27.63
See application file for complete search history.

(56) References Cited

U.S. PATENT DOCUMENTS

| 4,357,324 A | | 11/1982 | Montgomery et al. |
| 5,189,027 A | * | 2/1993 | Miyashita et al. ............. 514/46 |
| 5,278,150 A | * | 1/1994 | Olsson et al. .................. 514/46 |
| 5,589,467 A | | 12/1996 | Lau et al. |
| 5,998,388 A | | 12/1999 | Ellis et al. |
| 5,998,423 A | * | 12/1999 | Manneth et al. .......... 514/265.1 |
| 6,407,076 B1 | * | 6/2002 | Box et al. ...................... 514/46 |
| 6,576,620 B1 | * | 6/2003 | Belardinelli et al. ........... 514/46 |
| 6,605,597 B1 | * | 8/2003 | Zablocki et al. ............... 514/46 |

FOREIGN PATENT DOCUMENTS

| WO | WO 97/33591 A1 | 9/1997 |
| WO | WO 98/15276 A1 | 4/1998 |
| WO | WO 99/24450 A2 | 5/1999 |
| WO | WO 99/38877 A2 | 8/1999 |
| WO | WO 99/38877 A3 | 8/1999 |
| WO | WO 00/23457 A1 | 4/2000 |
| WO | WO 00/72799 A2 | 12/2000 |

OTHER PUBLICATIONS (R)van Tilburg et al., "N6,5'-O-Disubstituted Adenosine Derivatives as Partial Agonists for the Human Adenosine A3 Receptor," Journal of Medicinal Chemistry, 42(8), 1393-1400 (1999); Web published Mar. 31, 1999.* van Tilburg et al., "$N^6$,5'-Disubstituted Adenosine Derivatives as Partial Agonists for the Humans Adenosine $A_3$ Receptor," *Journal of Medicinal Chemistry*, 42(8), 1393-1400 (1999); Web published Mar. 31, 1999.*

Homma, Hiroshi et al "Nucleosides and Nucleotides. 112. 2-(1-Hexyn-1-y1)adenosine-5'-uranomides: A New Entry of Selective $A_2$Adenosine Receptor Agonists with Potent Antihypertensive Activity" J.Med. Chem. (1992) vol. 35 pp.: 2881-2890.

Matsuda, Akira et al "Nucleosides and Nucleotides. 103. 2-Alkynyladenosines: A Novel Class of Selective Adenosine $A_2$ Receptor Agonists with Potent Antihypertensive Effects" J. Med. Chem. (1992) vol. 35 pp.: 241-252 (Jan. 24, 1992).

Niiya, Kazunori "2-(N'-Alkylidenehydrazino)adenosines: Potent and Selective Coronary Vasodilators" J. Med. Chem. (1992) vol. 35 pp.: 4557-4561.

Van Der Wenden, Eleonora M. et al "5'-Substituted Adenosine Analogs as New High-Affinity Partial Agonist for the Adenosine $A_1$Receptor" J. Med. Chem (1998) vol. 41 pp.: 102-108.

Vittori, Sauro et al "2-Alkenyl and 2-Alkyl Derivatives of Adenosine and Adenosine-5'-N-Ethyluronamide: Different Affinity and Selectivity of E- and Z-Diastereomers at $A_{2A}$ Adenosine Receptors" J.Med. Chem (1996) vol. 39 pp.: 4211-4217.

(Continued)

Primary Examiner—L. E. Crane
(74) Attorney, Agent, or Firm—Browdy & Neimark, PLLC

(57) ABSTRACT

The present invention concerns novel C2,5'-disubstituted and $N^{6'}$,C2,5'-trisubstituted adenosine derivatives and their different uses. These adenosine derivatives were found to be potent adenosine receptor agonists and thus are of a therapeutic value in the treatment and prophylaxis of diseases and disorders affected by adenosine receptor agonists.

29 Claims, 2 Drawing Sheets

OTHER PUBLICATIONS

Bruns, R., "Adenosine Receptor Activation in Human Fibroblasts: Nucleoside Agonists and Antagonists", Can. J. Physiol. Pharmacol. 1980, 58: 673-691.

Chiang, et al., "S-Adenosyl-L-hemocysteine Hydrolase: Analogues of S-Adenosyl-L-homocysteine as Potential Inhibitors", Molecular Pharmacology. 1977, vol. 13, 939-947.

Cristalli, et al., "2-Alkynel Derivatives of Adenosine and Adenosine-5'-N-ethyluronamide as Selective Agonists at $A_2$ Adenosine Receptors", J. Med. Chem. 1992, vol. 35, 2363-2368.

Cristalli, et al., "Characterization of Potent Ligands at Human Recombinant Adenosine Receptors", Drug Development Research. 1998, vol. 45, 176-181.

Daly, et al., "Agonist Activity of 2- and 5'-substituted Adenosine Analogs and Their N6-Cycloalkyl Derivatives at $A_1$-and $A_2$-Adenosine Receptors Coupled to Adenylate Cyclase", Biochemical Pharmacology, vol. 43 No. 5, 1089-1093.

Gallo-Rodriguez, et al., "Structure-Activity Relationships of N6-Benzyladenosine-5'-uronamides as $A_3$-Selective Adenosine Agonists", J. Med. Chem. 1994, vol. 37, 636-646. Published in ACS ABstracts on Jan. 15, 1994.

Hutchinson, et al., "2-(Arylalkylamino)adenosine-5'-uronamides: A New Class of Highly Selective Adenosine $A_2$ Receptor Ligands", J. Med. Chem. 1990, vol. 33, 1919-1924.

Klotz, et al., "2-Substituted n-ethylcarboxamidoadenosine Derivatives as High-affinity Agonists at Human $A_3$ Adenosine Receptors", Naunyn-Schmiedeberg's Arch Pharmacol. 1999, vol. 360, 103-108. Published online Jul. 13, 1999.

Roelen, et al., "$N^6$, C8-Disubstituted Adenosine Derivatives as Partial Agonists for Adenosine $A_1$ Receptors", J. Med. Chem. 1996, vol. 39, 1463-1471. (Published in ACS Abstracts on Feb. 15, 1996).

Van Tilburg, et al., "2,5'-Disubstituted Adenosine Derivatives: Evaluation of Selectivity and Efficacy for the Adenosine $A_1$, $A_{2A}$ and $A_3$ Receptor", J. Med. Chem. 2002, vol. 45, 420-429. WEB published on Dec. 19, 2001.

Van Tilburg, et al., "6'-O-Alkyl Ethers of N,2-Substituted Adenosine Derivatives: Partial Agonists for the Adenosine $A_1$ and $A_3$ Receptor", J. Med. Chem. 2001, vol. 44, 2966-2975. WEB Published on Jul. 26, 2001.

Van Tilburg, et al., "N6,5'-Disubstituted Adenosine Derivatives as Partial Agonists for the Human Adenosine $A_3$ Receptor", J. Med. Chem. Apr. 22, 1999; vol. 42(8), 1393-1400.

Volpini, et al., "Synthesis of Di- and Tri-Substituted Adenosine Derivatives and Their ffinities at Human Adenosine Receptor Subtypes", Nucleosides & Nucleotides. 1999, vol. 18(11&12), 2511-2520.

* cited by examiner

C2,5'-DISUBSTITUTED AND N⁶, C2,5'-TRISUBSTITUTED ADENOSINE DERIVATIVES AND THEIR DIFFERENT USES

CROSS-REFERENCE TO RELATED APPLICATIONS

This application is a 371 national phase application of PCT/IL02/00160 filed Mar. 3, 2002, the entire content of which is herein incorporated by reference.

FIELD OF THE INVENTION

This invention relates to C2,5'-disubstituted and N⁶,C2, 5'-trisubstituted adenosine derivatives, pharmaceutical compositions containing them and the uses thereof.

LIST OF PRIOR ART

The following is a list of prior art which is considered to be pertinent for describing the state of the art in the field of the invention, all of which are also included in the list of publication that appears at the end of the description before the claims. Acknowledgement of these references herein will be made by indicating their number from the list of publications, which number is also indicated in brackets hereinbelow.

Van der Wenden, E. M., Carnielli, M., Roelen, H. C. P. F., Lorenzen, A., von Frijtag Drabbe Künzel, J. K., IJzerman, A. P, *J. Med. Chem.*, 1998, 41, 102–108 (reference no. 1).

Roelen, H., Veldman, N., Spek, A. L., von Frijtag, Drabbe Künzel, J., Mathot, R. A., IJzerman, A. P., *J. Med. Chem.*, 1996, 39, 1463–1471 (reference no. 2)

Gallo-Rodriquez, C., Ji, X., Melman; N., Siegman, B. D., Sanders, L. H., Orlina, J., Fischer, B., Pu, Q., Olah, M. E., van Galen, P. J. M., Stiles, G. L., Jacobson, K. A., *J. Med. Chem.*, 1994, 37, 636–646 (reference no. 3)

Van Tilburg, E. W., Von Frijtag Drabbe Künzel, J., Groote, M., Vollinga, R. C., Lorenzen, A., IJzerman, A. P., *J. Med. Chem.*, 1999, 42, 1393–1400 (reference no. 5)

Hutchison, A. J., Williams, M., deJesus, R., Yokoyama, R., Oei, H. H., Ghai, G. R., Webb, R. L., Zoganas, H. C., Stone, G. A., Jarvis, M. F., *J. Med. Chem.*, 1990, 33, 1919–1924 (reference no. 6).

Niiya, K., Olsson, R. A., Thompson, R. D., Silvia, S. K., Ueeda, M., *J. Med. Chem.*, 1992, 35, 4557–4561 (reference no. 7).

Cristalli, G., Eleuteri, A., Vittori, S., Volpini, R., Lohse, M. J., Klotz, K.-N., *J. Med. Chem.*, 1992, 35, 2363–2368 (reference no. 8)

Klotz, K.-N., Camaioni, E., Volpini, R., Kachler, S., Vittori, S., Cristalli, G., *Naunyn-Schmiedeberg's Arch. Pharmacol.*, 1999, 360, 103–108 (reference no. 9)

Volpini, R, Camaioni, E., Costanzi, S., Vittori, S., Klotz, K.-N., Cristalli, G., *Nucleosides and Nucleotides*, 1999, 18, 2511–2520 (reference no. 10)

Homma, H., Watanabe, Y., Abiru, T., Murayama, T., Nomura, Y., Matsuda, A., *J. Med. Chem.*, 1992, 35, 2881–2890 (reference no. 25)

Matsuda, A., Shinozaki, M., Yamaguchi, T., Homma, H., Nomoto, R., Miyasaka, T., Watanabe, Y., Abiru, T., Nucleosides and nucleotides. 103. 2-Alkynyladenosines: *J. Med. Chem.*, 1992, 35, 241–252 (reference no. 26)

Cristalli, G., Camaioni, E., Costanzi, S., Vittori, S., Volpini, R., Klotz, K. N., *Drug Dev. Res.*, 1998, 45, 176–181 (reference no. 27)

Chan, C., (G B), G. W., *PCT Int. Appl.* 104 pp. WO 99/38877 A2 990805, 1999 (reference no. 31)

BACKGROUND OF THE INVENTION

Adenosine acts extracellularly via activation of specific membrane-bound receptors called $P_1$-purinoceptors. These adenosine receptors can be divided into four subclasses, $A_1$, $A_{2A}$, $A_{2B}$ and $A_3$ receptors. All four classes are coupled to the enzyme adenylate cyclase. Activation of the adenosine $A_1$ and $A_3$ receptors leads to an inhibition of adenylate cyclase, while activated $A_{2A}$ and $A_{2B}$ receptors stimulate adenylate cyclase. The adenosine receptors are ubiquitously distributed throughout the body. As a consequence, ligands need to be highly selective in their action with respect to receptor subtype and tissue to be of therapeutic value.

Receptor subtype selectivity can be achieved by substituting the adenosine molecule. For example modification at the N⁶ position of adenosine is well tolerated. N⁶-substituents such as cyclopentyl enhance adenosine $A_1$ receptor selectivity relative to the other subtypes,[1,2] while a 3-iodobenzyl group induces adenosine $A_3$ receptor selectivity.[3-5] Bulky substituents such as (ar)alkylamino,[6] alkylidenehydrazino[7] and alkynyl,[8] at the 2-position of the adenine moiety yield selectivity for the adenosine $A_{2A}$ receptor compared to $A_1$. Only more recently, the 2-(ar)alkynyl adenosine derivatives have been evaluated at the adenosine $A_3$ receptor. Quite surprisingly, some of these compounds appeared to be selective for the adenosine $A_3$ receptor rather than for $A_{2A}$.[9,10]

Tissue selectivity is often the result of partial agonism, which may reduce the extent of side effects.[11,12] Due to differences in receptor-effector coupling in various tissues selectivity of action in vivo may be achieved. Partial agonists for the adenosine receptors may be of use as antipsychotic drugs, e.g., via stimulation of the adenosine $A_{2A}$ receptor that leads to inhibition of dopamine $D_2$ receptors in the basal ganglia,[13,14] and as cardio- and cerebroprotective agents via the adenosine $A_3$ receptor when chronically administered.[15,16].

SUMMARY OF THE INVENTION

The present invention provides a compound of the general formula (I):

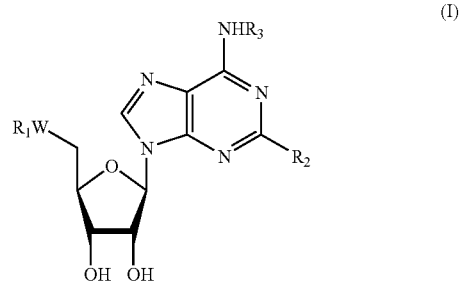

wherein
W represents an oxygen or sulfur atom;
$R_1$ represents a lower alkyl or lower cycloalkyl;

$R_2$ represents a halogen, lower alkenyl, lower alkynyl or lower alkylidenehydrazino group;

$R_3$ represents a hydrogen, lower alkyl, lower cycloalkyl, aryl, anilide or (ar)alkyl; said cycloalkyl, aryl or (ar)alkyl may be substituted with one or more of the substituents selected from halogen, hydroxyl or hydroxyalkyl;

or a salt of said compound.

By the term "alkyl" which may be used herein interchangeably with the term "lower alkyl", it is meant any saturated carbohydrate, either linear or branched chain comprising from 1 to about 10 carbon atoms in the backbone.

Accordingly, the terms "alkenyl" and "alkynyl" which are also used interchangeably and respectively with the terms "lower alkenyl" and "lower alkynyl" refer to linear or branched carbohydrates comprising from 2 to 10 carbon atoms in the backbone, wherein at least two of the carbon atoms are connected via a double or triple bond, respectively.

Thus, it is to be understood that the term "lower" when used a prefix for defining a carbohydrate, refers to any carbohydrate having in its backbone no more than 10 carbon atoms.

When referring to salts of the compound of the present invention it is meant any physiologically acceptable salt. The term "physiologically acceptable salt" refers to any non-toxic alkali metal, alkaline earth metal, and ammonium salts commonly used in the pharmaceutical industry, including the sodium, potassium, lithium, calcium, magnesium, barium ammonium and protamine zinc salts, which are prepared by methods known in the art. The term also includes non-toxic acid addition salts, which are generally prepared by reacting the compounds of this invention with a suitable organic or inorganic acid. The acid addition salts are those which retain the biological effectiveness and properties of the free bases and which are not biologically or otherwise undesirable. Examples include acids are those derived from mineral acids, and include, inter aila, hydrochloric, hydrobromic, sulfuric, nitric, phosphoric, metaphosphoric and the like. Organic acids include, inter alia, tartaric, acetic, propionic, citric, malic, malonic, lactic, fumaric, benzoic, cinnamic, mandelic, glycolic, gluconic, pyruvic, succinic salicylic and arylsulphonic, e.g. p-toluenesulphonic, acids.

The present invention also provides pharmaceutical compositions comprising as active ingredient an effective amount of a compound of the general formula (I) as defined above.

Furthermore, the invention concerns the use of the compounds of the present invention as adenosine receptor ligands, preferably adenosine receptor agonists.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
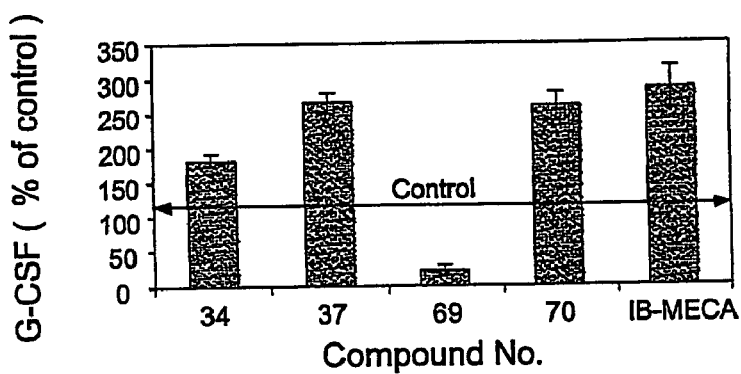
FIG. 1 is a bar graph showing result of in an in vitro assay in which the level of G-CSF production in human cord blood sample in the presence of 50 µM of drug was determined. In particular, the effect of compounds 34, 37, 69 and 70 (as referenced hereinbelow) on the production of G-CSF was tested, while the effect of an adenosine A3 receptor agonist, IB-MECA, served as the control.

The present invention is based on the development of several novel adenosine receptor agonists. Thus, according to a first of its aspects the present invention provides compounds of the general formula (I):

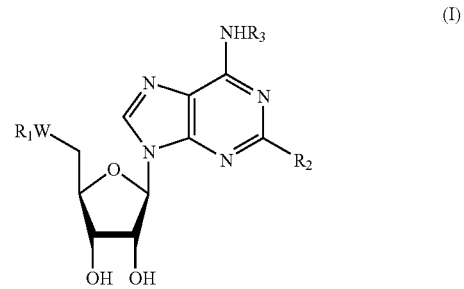

in which

W represents an oxygen, or sulfur atom;

$R_1$ represents a lower alkyl or lower cycloalkyl;

$R_2$ represents a halogen, lower alkenyl, lower alkynyl or lower alkylidenehydrazino;

$R_3$ represents a lower alkyl, lower cycloalkyl, (ar)alkyl, aryl or anilide, said cycloalkyl, aryl or (ar)alkyl may, be substituted with one or more halogen atom(s), hydroxy, hydroxyalkyl;

or a salt of said compound.

More particularly, the present invention provides compounds of general formula (I), wherein the substituents are as follows:

W represents an oxygen or sulfur atom;

$R_1$ represents a lower alkyl or cycloalkyl;

$R_2$ represents a halogen, alkynyl or alkylidenehydrazino; and $R_3$ represents a cycloalkyl or an (ar)alkyl, said aralkyl optionally substituted with at least one halogen atom.

According to some specific embodiments, the compounds of the present invention are those in which W represents a sulfur atom;

$R_1$ represents an alkyl group;

$R_2$ represents a halogen atom; and $R_3$ represents a hydrogen atom.

According to one preferred embodiment, W represents a sulfur atom, $R_1$ is a lower alkyl selected from the group consisting of methyl, ethyl, n- and i-propyl; $R_2$ is iodine; and $R_3$ is a hydrogen.

According to a second preferred embodiment, W is a sulfur atom, $R_1$ is a lower alkyl selected from the group consisting of methyl, ethyl, n- and i-propyl; $R_2$ is an alkynyl group; and $R_3$ is a hydrogen. According to this embodiment, $R_2$ is preferably 1-hexynyl.

According to a third preferred embodiment, W is a sulfur atom, $R_1$ is a lower alkyl selected from the group consisting of methyl, ethyl, n- and i-propyl; $R_2$ is an alkylidenehydrazino; and $R_3$ is a hydrogen. According to this embodiment, $R_2$ is preferably N'-3-methyl-1-butylidenehydrazino.

According to a fourth preferred embodiment, W is an oxygen atom, $R_1$ is an alkyl, $R_2$ is a halogen atom; and $R_3$ is selected from hydrogen, cycloalkyl or a substituted or unsubstituted (ar)alkyl group. More preferably, $R_1$ is a lower alkyl selected from methyl, ethyl, or cyclopropyl, $R_2$ is a chloride, and $R_3$ is a halobenzyl, preferably 3-iodobenzyl.

Specific compounds of the present invention include:
5'-Deoxy-2-iodo-5'methylthioadenosine; (compound 33 hereinafter);
5'-Deoxy-2-iodo-5'-ethylthioadenosine (compound 34 hereinafter);
5'-Deoxy-2-iodo-5'-propylthioadenosine (compound 35 hereinafter).
5'-Deoxy-2-iodo-5'-isopropylthioadenosine (compound 36 hereinafter);
5'-Deoxy-2-(1-hexynyl)-5'-methylthioadenosine (compound 37 hereinafter);
5'-Deoxy-2-(1-hexynyl)-5'-ethylthioadenosine (compound 38 hereinafter);
5-Deoxy-2-(1-hexynyl)-5'-propylthioadenosine (compound 39 hereinafter);
5'-Deoxy-2-(1-hexynyl)-5'-isopropylthioadenosine (compound 40 hereinafter);
5'-Deoxy-2-(N'-3-methyl-1-butylidenehydrazino)-5'-methylthioadenosine (compound 45 hereinafter);
5'-Deoxy-2-(N'-3-methyl-1-butylidenehydrazino)-5'-ethylthioadenosine (compound 46 hereinafter);
5'-Deoxy-2-(N'-3-methyl-1-butylidenehydrazino)-5'-propylthioadenosine (compound 47 hereinafter);
5'-Deoxy-2-(N'-3-methyl-1-butylidenehydrazino)-5'-isopropylthioadenosine (compound 48 hereinafter);
$N^6$-Cyclopentyl-5'-O-methyladenosine (compound 67 hereinafter);
$N^6$-(3-Iodobenzyl)-5'-O-methyladenosine (compound 68 hereinafter);
2-Chloro-5'-O-methyladenosine (compound 69 hereinafter)
$N^6$-Cyclopentyl-2-chloro-5'-O-methyladenosine (compound 70 hereinafter);
$N^6$-(3-Iodobenzyl)-2-chloro-5'-O-methyladenosine (compound 71 hereinafter);
$N^6$-Cyclopentyl-5'-O-ethyladenosine (compound 73 hereinafter);
$N^6$-(3-Iodobenzyl)-5'-O-ethyladenosine (compound 74 hereinafter);
2-Chloro-5'-O-ethyladenosine (compound 75 hereinafter);
$N^6$-Cyclopentyl-2-chloro-5'-O-ethyladenosine (compound 76 hereinafter);
$N^6$-(3-Iodobenzyl)-2-chloro-5'-O-ethyladenosine (compound 77 hereinafter);
$N^6$-Cyclopentyl-5'-O-cyclopropyladenosine (compound 78, 79 hereinafter);
$N^6$-(3-iodobenzyl)-5'-O-cyclopropyladenosine (compound 80 hereinafter);
2-Chloro-5'-O-cyclopropyladenosine (compound 81 hereinafter);
$N^6$-Cyclopentyl-2-chloro-5'-O-cyclopropyladenosine (compound 82 hereinafter);
$N^6$-(3-iodobenzyl)-2-chloro-5'-O-cyclopropyladenosine (compound 83 hereinafter);

The compounds of the present invention may be prepared by several synthesis procedures. For example, the synthesis route to obtain the C2,5'-disubstituted derivatives 33–40 and 45–48 are depicted in scheme 1 hereinbelow:

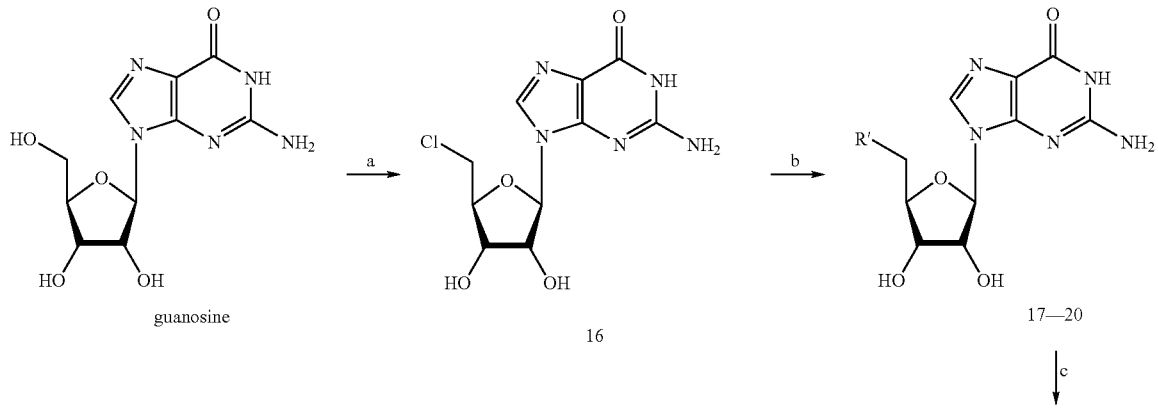

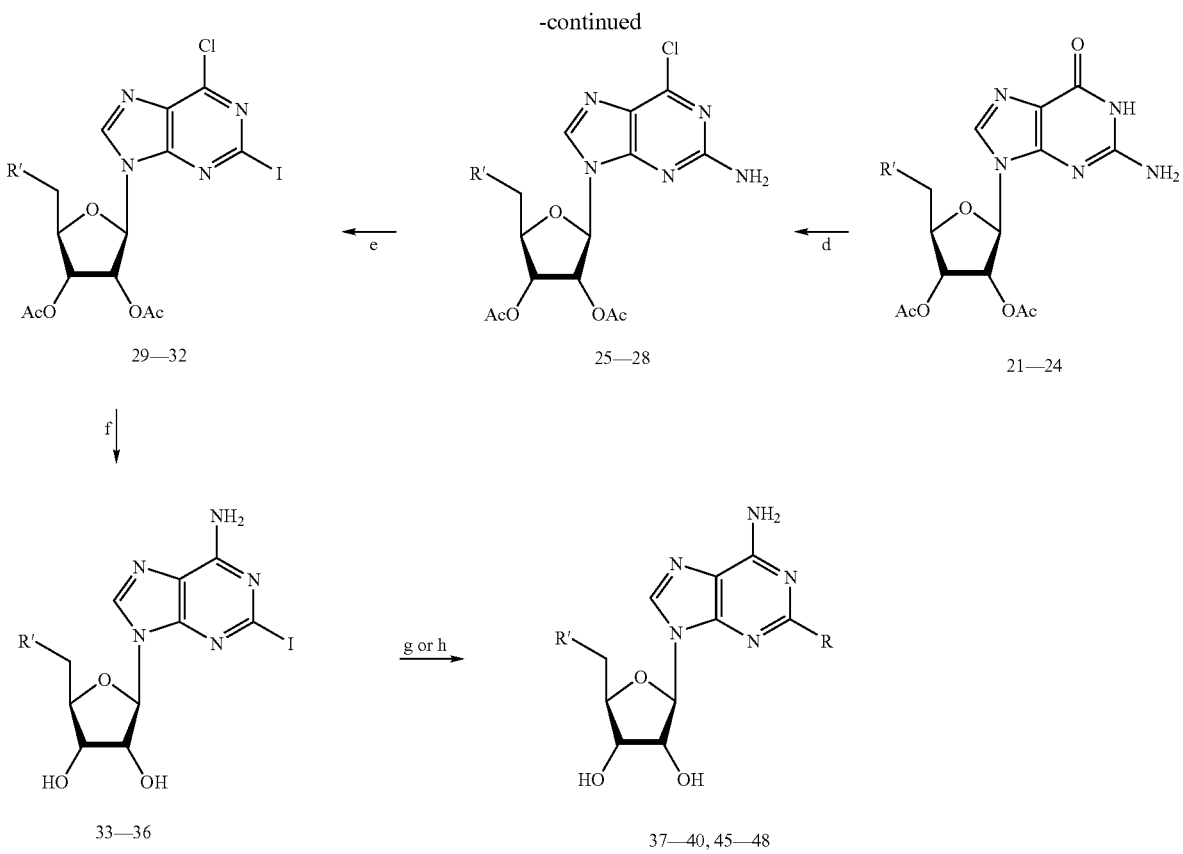

R' = SCH$_3$, SC$_2$H$_5$, S-n—C$_3$H$_7$ or S-i—C$_3$H$_7$; 37—40 R=C≡C(CH$_2$)$_3$CH$_3$;
45 R=NHN=CHCH$_2$CH(CH$_3$)$_2$; (a) HMPA, SOCl$_2$, Dowex 50 W (H$^+$); (b) i) RSH,
2M NaOH, reflux ii) acetic acid; (c) i) DMAP, CH$_3$CN, Et$_3$N, acetic anhydride ii) MeOH;
(d) CH$_3$CN, Et$_4$NCl, N,N-dimethylaniline, POCl$_3$, reflux; (e) I$_2$, CH$_2$I$_2$, CuI, isopentylnitrite,
THF; (f) EtOH/NH$_3$; (g) CH$_3$CN, Et$_3$N, CuI, PdCl$_2$, Ph$_3$P, 1-hexyn; (h) i) isopropanol,
hydrazine monohydrate, reflux ii) MeOH, isovaleraldehyde, reflux According to this scheme, the synthesis of the compounds of the invention started with 2-iodoadenosine (1), which is an important intermediate for the synthesis of several adenosine derivatives, described in literature.[18] 2-Hydrazinoadenosine (2) was synthesized starting from 1 by stirring it with hydrazine monohydrate at 80° C. 2-(N'-3-Methyl-1-butylidenehydrazino)-adenosine (3) was generated by the condensation of 2 with isovaleraldehyde according to the method of Niiya et al.[7] 2-(1-Hexynyl)adenosine (4) was prepared in good yield (88%) by reacting 1 with 1-hexyn.[8,19] Part of the synthesis route for compounds 33–40 and 45–48 was similar to that of compounds 2–4, except for the fact that prior to C-2 substitution, the 5'-alkylthio substituents were introduced. In fact, this was performed in an early stage of the route, i.e. at commercially available guanosine, which was also used as the starting material for 2-iodoadenosine (1) itself. The 5'-(alkylthio)-substituted derivatives 17–20 were obtained by reacting 5'-chloro-5'-deoxy-guanosine (16) with the appropriate thiol in 2 M NaOH.[1,5,20] Subsequently, the 2',3'-hydroxyl groups were acetyl protected to avoid complications during further synthesis, and compounds 21–24 were obtained in quantitative yields.

Chlorination on the 6-position of compounds 21–24 was performed with phosphoryl chloride (POCl$_3$),[18,21] yielding 2-amino-6-chloro-9-(2,3-di-O-acetyl-5-alkylthio-5-deoxy-α-D-ribo-furanosyl)-purine derivatives 25–28 in reasonable to good yields (40–74%). Subsequently, the 2-amino group of compounds 25–28 was replaced by iodine via a diazotization-iodine substitution reaction.[22] This method appeared to be an efficient way to prepare 29–32. The 5'-alkylthio-2-iodoadenosine intermediates, 33–36, were obtained by stirring 29–32 with ethanol saturated with ammonia. The acetyl protecting groups were readily removed under these conditions. The 6-position, however, was aminated only after a few days. Finally, as for compound 3,[8] the 2-(1-hexynyl) group could be easily introduced in 33–36, and the 5'-alkylthio-5'-deoxy-2-(1-hexynyl)adenosine derivatives 37–40 were obtained in good yields. The 5'-aklylthio-5'-deoxy 2-(N'-3-methyl-1-butylidenehydrazino)adenosine derivatives (45–48) were synthesized by the condensation of the 5'-deoxy-2-hydrazino-5'-althylthioadenosine derivatives (41–44) with isovaleraldehyde as described above.[7]

Alternatively, the N$^6$,C2,5'-tri-substituted adenosine derivatives 66–83 of the invention may be prepared by the following scheme 2:

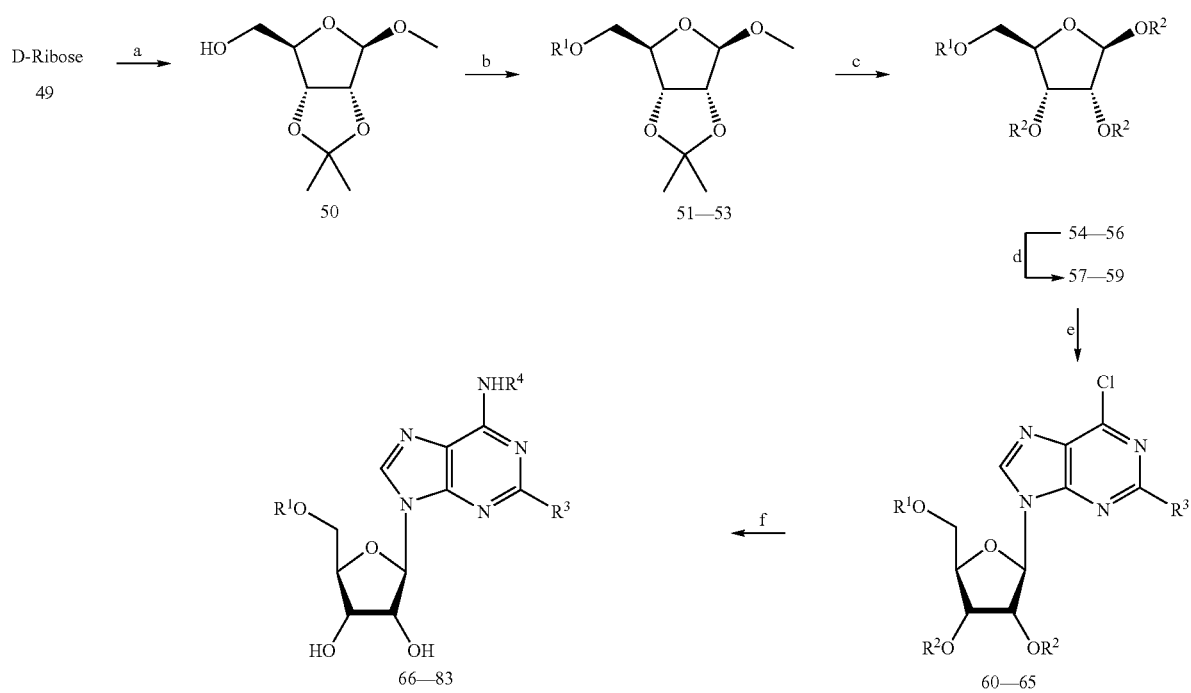

Reaction conditions: a: acetone; MeOH, 2,2-dimethoxypropane, HCl gas, b: NaH, DMF, alkylhalide, c: i) 0.04 M NaOH ii) BaCO₃, d) pyridine, DMAP, acetic anhydride, e: 1,2-dichloroethane, silylated base, TMSOTf, f. i) EtOH/NH₃ or ii) abs. EtOH, appropriate amine According to this scheme, the protected ribose (50) was obtained by leading HCl gas through a solution of the starting material D-ribose (49) in a mixture of acetone, MeOH and 2,2-dimethoxypropane.[48] Alkylation of the free hydroxyl group of 50 was performed under standard conditions, i.e. treatment with NaH in DMF under cooling, followed by the addition of the alkylhalide iodomethane, iodoethane or cyclopropylbromide, respectively. Subsequently, the protecting groups of the alkylated compounds 51–53 were removed by refluxing the material in aqueous HCl (0.04 M) for 2 hours, and compounds 54–56 were obtained.[49] The hydroxyl groups of 54–56 were then protected with acetyl groups. The fully protected compounds 57–59 were then coupled to the appropriate heterocyclic base, e.g. 6-chloropurine or 2,6-dichloropurine, according to the Vorbröggen method[45] to give compounds 60–65 in good yields (48–84%). Amination with EtOH/NH₃, cyclopentylamine or 3-iodobenzylamine gave the unprotected substituted adenosine derivatives 68–83.[1,5]

As will be detailed in the following specific examples, the compounds of the present invention are biologically active.

The term "biologically active" indicates that the compound of the present invention has a biological activity, for example, a measurable effect on a target receptor. As will be detailed hereinafter, the compound of the present invention may induce the biological action of adenosine receptors, thus acting as adenosine receptor agonists.

The term "agonist" used herein refers to a biologically active ligand, which binds to its complementary biologically active receptor and activates the latter either to cause a biological response in the receptor or to enhance preexisting biological activity of the receptor. The agonist in fact mimics the effect of the natural ligand, in the present case, the adenosine, or at times, even increases or prolongs the duration of the biological effect obtained as compared to the effect induced by the natural ligand.

More preferably and as will be shown in the following Specific Examples, the compounds of the present invention are partial agonists of adenosine receptors.

A compound according to the invention is considered a "partial agonist" if it is unable to produce maximal activation of the receptor to which it binds no matter how high is its concentration.

The present invention also provides pharmaceutical compositions comprising as active ingredient an effective amount of one or more of a compound of the general formula (I):

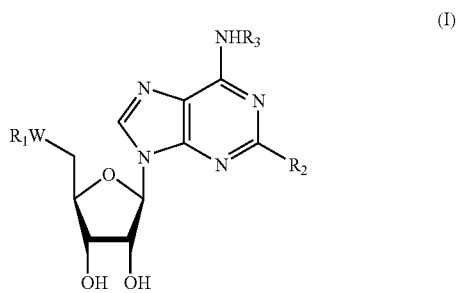

(I)

in which
W represents an oxygen, or sulfur atom;
R₁ represents a lower alkyl or lower cycloalkyl;
R₂ represents a halogen, lower alkenyl, lower alkynyl or lower alkylidenehydrazino;

R₃ represents a lower alkyl, lower cycloalkyl, (ar)alkyl, aryl or anilide, said cycloalkyl, aryl or (ar)alkyl may be substituted with one or more halogen atom(s), hydroxy, hydroxyalkyl;

or a salt of said compound.

The "effective amount" for purposes herein is determined by such considerations as may be known in the art. The amount must be effective to achieve the desired therapeutic effect e.g. activation or inhibition of cAMP through the binding of the compounds of the present invention to an adenosine receptor. The effective amount depends, inter alia, on the type and severity of a disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half life in the body, on undesired side effects, if any, on factors such as age and gender, etc.

The terms "treat", "treating" and "treatment" refer to the administering of a therapeutic amount of the compound or composition of the present invention which is effective to ameliorate undesired symptoms associated with a disease, to prevent the manifestation of such symptoms before they occur, to slow down the progression of a disease, to slow down the deterioration of symptoms, to slow down the irreversible damage caused by the chronic stage of a disease, to lessen the severity or cure a disease, to improve survival rate or more rapid recovery, to prevent the disease from occurring, or a combination of two or more of the above.

According to one embodiment of the invention, the disease is preferably such, which requires for its treatment the activation or inhibition of cAMP via the binding of a compound of the invention to an adenosine receptor. For example, compounds of the invention which in preference bind and activate the A₁ receptors may be implicated as e.g., sleep modulator, antihypertensives, analgesics, antidiabetic compounds, tissue-protective agents, compounds which bind and activate the A₂ₐ receptors may be implicated as e.g. antihypertensives and neuroleptics while compounds which bind and activate the A₃ receptors may be implicated as e.g. tissue-protective agents and anti-tumor agents.

The pharmaceutical composition of the present invention may father comprise pharmaceutically acceptable additives.

Further, the term "pharmaceutically acceptable additives" used herein refers to any substance combined with said compound and include, without being limited thereto, diluents, excipients, carriers, solid or liquid fillers or encapsulating materials which are typically added to formulations to give them a form or consistency when it is given in a specific form, e.g. in pill form, as a simple syrup, aromatic powder, and other various elixirs. The additives may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc.

Preferably, the additives are inert, non-toxic materials, which do not react with the active ingredient of the invention. Yet, the additives may be designed to enhance the binding of the active agent to its receptor. Further, the term additive may also include adjuvants, being substances affecting the action of the active ingredient in a predictable way.

The additives can be any of those conventionally used and are limited only by chemico-physical considerations, such as solubility and lack of reactivity with the compound of the invention, and by the route of administration.

The active agent of the invention may be administered orally to the patient. Conventional methods such as administering the compound/s in tablets, suspensions, solutions, emulsions, capsules, powders, syrups and the like are usable.

For oral administration, the composition of the invention may contain additives for facilitating oral delivery of the compound/s of the invention. Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodiumk talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active agent in a flavor, usually sucrose and acacia or tragacanth, as well as pastilles comprising the active ingredient in an inert base, such as gelatin and glycerin, or sucrose and acacia, emulsions, gels, and the like. Such additives are known in the art.

Alternatively, the compound/s may be administered to the patient parenterally. In this case, the composition will generally be formulated in a unit dosage injectable form (solution, suspension, emulsion). Pharmaceutical formulation suitable for injection may include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, lipid polyethylene glycol and the like), suitable mixtures thereof; a vegetable oil such as cottonseed oil, sesame oil, olive oil, soybean oil, corn oil, sunflower oil, or peanut oil; a fatty acid esters such as ethyl oleate and isopropyl myristate and variety of other solvent systems as known per se. The carrier may be chosen based on the physical and chemical properties of the active agent.

In case the active ingredient has poor water solubility, and an oily carrier is therefore used, proper fluidity can be maintained, for example, by the use of a emulsifiers such as phospholipids, e.g. lecithin or one of a variety of other pharmaceutically acceptable emulsifiers. As known per se, the proper choice if a surfactant and the treatment conditions may also permit to control the particle size of the emulsion droplets.

Suitable soaps for use in parenteral formulations, in case the active ingredient has poor water solubility, include fatty alkali metal, ammonium, and triethanolamine salts, and suitable detergents include oleic acid, stearic acid, and isostearic acid. Ethyl oleate and isopropyl myristate are examples of suitable fatty acid esters.

Suitable detergents for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

Further, in order to minimize or eliminate irritation at the site of injection, the compositions may contain one or more nonionic surfactants having a hydrophile-lipophile balance (HLB) of from about 12 to about 17. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The choice of an additive will be determined in part by the particular compound of the present invention, as well as by the particular method used to administer the composition.

Notwithstanding the above, the composition of the present invention may include one or more of the compounds of the present invention and may be comprise other biologically active substances, to provide a combined therapeutic effect.

The compounds and compositions of the present invention as set forth hereinabove and below are administered and dosed in accordance with good medical practice, taking into account the clinical conditions of the individual patient, the site and method of administration, scheduling of administration, individual's age, sex, body weight and other factors known to medical practitioners.

The dose may be single doses or multiple doses over a period of several days. The treatment generally has a length proportional to the length of the disease process and drug effectiveness and the individual species being treated. Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments, until the optimum effect under the circumstances is reached. Exemplary dosages range from about 0.001 mg/kg body weight to about 10 mg/kg body weight of the subject being treated/day.

Some of the new compounds of the invention are agonists of the A1 adenosine receptor ("A1 Agonist") some others are agonists of the A2 adenosine receptor ("A2 Agonist") and some others are agonists of the A3 adenosine receptor ("A3 Agonist"). Some of the compounds may also have agonistic activity to more than one of these adenosine receptors. Additionally, some of them show full agonistic activity and some show partial agonistic activity. Thus, different compounds of the invention may have different therapeutic applications based on their different agonistic activity. The agonistic activity for a specific compound may be determined based on its binding properties and on its biological effect. For example, it is known that A3 agonists can inhibit proliferation of tumor cells on the one hand and induce proliferation of white blood cells and neutrophils on the other hand (see WO01/19360). Thus, to determine whether a compound has an A3 agonistic activity, it may be incubated in vitro with tumor cells and with white blood cells and measure cell proliferation in order to show its dual effect on said cells. Furthermore, a compound shown to have an A3 agonistic activity in vitro may then be administered to animals using appropriate animal models (see WO01/19360) to determine its in vivo effect.

Similarly, A1 agonists are known to induce proliferation of white blood cells but, unlike A3 agonists, do not inhibit proliferation of tumor cells. Thus, an assay similar to that disclosed above, compounds of A1 agonistic activity may be determined.

For example, compounds that have either A1 or A3 agonistic activity may be used for protection against drug-induced myelotoxicity. Compounds, having an A3 agonistic activity may be used for anti-cancer agents.

Compounds with A2 agonistic activity are known to be active as neuroleptic agents, e.g. for the treatment of psychosis, or for wound healing. Thus, appropriate models to test such activity may be used in order to evaluate whether a given compound is an A2 agonist.

Additionally, various binding assays known per se may also be used in order to determine affinity of the compounds to any one of the adenosine receptors.

The therapeutic utility for a given compound can thus be determined based on such assays.

The invention has been described in an illustrative manner, and it is to be understood that the terminology which has been used, is intended to be in the nature of words of description rather than of limitation. Obviously, many modifications and variations of the present invention are possible in light of the above teaching. It is therefore, to be understood that within the scope of the appended claims, the invention may be practiced otherwise than as specifically described hereinafter.

Throughout the description various publications are referred to by a number. Full citations of the publications are listed at the end of the description before the claims.

SPECIFIC EXAMPLES

Example 1

Synthesis of C2,5'-disubstituted Adenosine Derivatives

Chemistry—General

Chemicals and solvents. Guanosine was obtained from Aldrich (Aldrich Chemie, Sigma-Aldrich Chemie BV, Zwijndrecht, The Netherlands). All other reagents were from standard commercial sources and of analytic grade. [$^3$H] DPCPX (1,3-dipropyl-8-cyclopentylxanthine), [$^3$H]ZM 241385 and [$^{125}$I]AB-MECA were purchased from NEN (Hoofddorp, The Netherlands).

Chromatography. Thin-layer chromatography (TLC) was carried out using aluminium sheets (20×20 cm) with silica gel $F_{254}$ from Merck. Spots were visualized under UV (254 nm). Preparative column chromatography was performed on silica gel (230–400 mesh ASTM).

Instruments and Analysis. Elemental analyses were performed for C, H, N (Department of Analytical Chemistry, Leiden University, The Netherlands). $^{13}$C NMR spectra were measured at 50.1 MHz with a JEOL JNM-FX 200 spectrometer equipped with a PG 200 computer operating in the Fourier-transform mode. $^1$H NMR spectra were measured at 200 MHz, using the above mentioned spectrometer, or at 300 MHz, using a Bruker WM-300 spectrometer equipped with an ASPECT-2000 computer operating in the Fourier-transform mode. Chemical shifts for $^1$H and $^{13}$C NMR are given in ppm (δ) relative to tetramethylsilane (TMS) as internal standard.

All high resolution mass spectra were measured on a Finnigan MAT900 ass spectrometer equipped with a direct insertion probe for EI experiments (70 eV with resolution 1000) or on a Finnigan MAT TSQ-70 spectrometer equipped with an electrospray interface for ESI experiments. Spectra were collected by constant infusion of the analyte dissolved in 80/20 methanol/H$_2$O. ESI is a soft ionization technique resulting in protonated, sodiated species in positive ionization mode and deprotonated species in the negative ionization mode.

Resolution of the compounds was achieved by reverse-phase HPLC (Gilson HPLC system, 712 system controller software. Gilson Netherlands, Meyvis en Co BV, Bergen op Zoom, the Netherlands) using a 65% MeOH/31.5% H$_2$O/ 3.5% CH$_3$CN (v/v) mobile phase, an Alltima C18 5μ (250 mm×4.6 mm) or a nucleotide/nucleoside 7μ (250 mm×4.6 mm) column (Alltech Nederland BV, Breda, the Netherlands) at a flow rate of 0.7 ml/min. The peaks were defined by measurement of UV absorbance (254 nm). Retention times are given.

Melting points were determined in a Büchi capillary melting point apparatus.

Synthesis Procedures

Syntheses. 5'-Chloro-5'-deoxyguanosine (compound 16). Guanosine (43.5 g, 0.15 mol) was dissolved in hexamethylphosphorictriamide (HMPA, 40 ml, 0.23 mol). Thionyl chloride (61.5 ml, 0.85 mol) was added in 1 h. The mixture was stirred at ambient temperature for 1 h, diluted with water and chromatographed on Dowex 50 W (H$^+$). After washing with water (350 mL), the product was collected by eluting 5% aqueous ammonia (350 ml). The fraction was concentrated in vacuo.

Yield 40 g (0.13 mol, 86%), $^1$H NMR (DMSO-d$_6$) δ 10.53 (bs, 1H, NH), 7.89 (s, 1H, H-8), 6.50 (bs, 2H, NH$_2$), 5.72 (d, J=5.84 Hz, 1H, H-1'), 5.55 (d, J=6.52 Hz, 1H, OH-2'), 5.39–5.35 (m, 1H, OH-3'), 4.57 (q, J=5.15 Hz, 1H, H-2'), 4.16–4.05 (m, 1H, H-3'), 4.05–3.97 (m, 1H, H-4'), 3.86 (dq, J=11.67 Hz, 2H, H-5').

General procedure for the syntheses of 5'-alkylthio derivatives (compounds 17–20). The appropriate thiol (3.32 mmol) was dissolved in 10 ml 2 M NaOH. After stirring, 5'-chloro-5'-deoxyguanosine (16; 100 mg, 0.33 mmol) was slowly added. The mixture was refluxed for 2–2.5 h and then cooled to room temperature. It was acidified with acetic acid and a white precipitate was formed. The precipitate was filtered and dried.

5'-Deoxy-5'-methylthioguanosine (compound 17). The reaction was carried out with sodium thiomethoxide (27.42 g, 0.39 mol) and 16 (11.8 g, 39.1 mmol). Yield 10.41 g (33.2 mmol, 85%), $^1$H NMR (DMSO-d$_6$) δ 7.85 (s, 1H, H-8), 7.23 (bs, 2H, NH$_2$), 5.68 (d, J=6.18 Hz, 1H, H-1'), 4.53–4.51 (m, 1H, H-2'), 4.05–3.99 (m, 1H, H-3'), 3.99–3.95 (m, 1H, H-4'), 2.78 (t, J=6.52 Hz, 2H, H-5'), 1.67 (s, 3H, CH$_3$).

5'-Deoxy-5'-ethylthioguanosine (compound 18). The reaction was carried out with ethanethiol (20.6 ml (0.28 mol) and 16 (8.40 g, 27.8 mmol). Yield 6.98 g (21.3 mmol, 77%), $^1$H NMR (DMSO-d$_6$) δ 10.70 (bs, 1H, NH), 7.90 (s, 1H, H-8), 6.48 (bs, 2H, NH$_2$), 5.68 (d, J=6.18 Hz, 1H, H-1'), 5.52–5.48 (m, 1H, OH-2'), 5.32–5.19 (m, 1H, OH-3'), 4.55–4.52 (m, 1H, H-2'), 4.05–4.03 (m, 1H, H-3'), 4.03–3.91 (m, 1H, H-4'), 2.80 (pt, J=7.21 Hz, 2H, H-5'), 2.49 (m, 2H, CH$_2$), 1.13 (t, J=7.21 Hz, 3H, CH$_3$).

5'-Deoxy-5'-propylthioguanosine (compound 19). The reaction was carried out with 1-propanethiol (27.0 ml, 0.30 mol) and 16 (9.0 g, 29.8 mmol).

Yield 6.1 g (17.9 mmol, 60%), $^1$H NMR (DMSO-d$_6$) δ 10.69 (bs, 1H, NH), 7.90 (s, 1H, H-8), 6.51 (bs, 2H, NH$_2$), 5.67 (d, J=5.84 Hz, 1H, H-1'), 4.55 (t, J=3.42 Hz, 1H, H-2'), 4.03 (t, J=3.43 Hz, 1H, H-3'), 3.93 (pt, J=3.44 Hz, 1H, H-4'), 2.78 (pt, J=6.18 Hz, 2H, H-5'), 2.49 (m, 2H, SCH$_2$), 1.49 (q, J=7.20 Hz, 2H, CH$_2$CH$_3$), 0.86 (t, J=7.20 Hz, 3H, CH$_3$).

5'-Deoxy-5'-isopropylthioguanosine (compound 20). The reaction was carried out with 2-propanethiol (30.8 ml, 0.33 mol) and 16 (10.0 g, 33.2 mmol).

Yield 6.64 g (19.5 mmol, 59%), $^1$H NMR (DMSO-d$_6$) δ 10.68 (bs, 1H, NH), 7.90 (s, 1H, H-8), 6.49 (bs, 2H, NH$_2$), 5.67 (d, J=6.18 Hz, 1H, H-1'), 4.52 (t, J=5.49 Hz, 1H, H-2'), 4.03 (t, J=4.46 Hz, 1H, H-3'), 3.92 (pq, J=6.86 Hz, 1H, H-4'), 3.04–2.69 (m, 2H, H-5'), 3.04–2.69 (m, 1H, CH), 1.17 (d, J=6.53 Hz, 6H, CH$_3$).

General acetylation procedure of derivatives 17–20 to obtain compounds 21–24. To a suspension of compound 17 (0.46 mmol) and 4-dimethylaminopyridine (DMAP; 0.03 mmol) in a mixture of acetonitrile (5.7 ml) and triethylamine (154 μl, 1.1 mmol) was added acetic anhydride (95 μl, 1 mmol) at room temperature. The mixture was stirred for 1 h until the solution became clear. Methanol (10 ml) was added and the solution was stirred for 5–10 minutes, concentrated in vacuo and stirred with isopropanol. The white slurry obtained was filtered and subsequently stirred with hexane. The white precipitate was filtered and dried.

2',3'-di-O-Acetyl-5'-deoxy-5'-methylthioguanosine. (compound 21). The reaction was carried out with 5'-deoxy-5'-methylthioguanosine (17, 10.4 g, 33.2 mmol). Yield 10.5 g (26.4 mmol, 79%), $^1$H NMR (DMSO-d$_6$) δ 7.98 (s, 1H, H-8), 6.59 (bs, 2H, NH$_2$), 5.99–5.90 (m, 1H, H-1'), 5.99–5.90 (m, 1H, H-2'), 5.43 (t, J=3.78 Hz, 1H, H-3'), 4.24 (pq, J=3.19 Hz, 1H, H-4'), 2.96–2.88 (m, 2H, H-5'), 2.11, 2.07 (2×s, 6H, 2×COCH$_3$), 2.00 (s, 3H, SCH$_3$).

2',3'-di-O-Acetyl-5'-deoxy-5'-ethylthioguanosine (compound 22). The reaction was carried out with 5'-deoxy-5'-ethylthioguanosine (18, 6.98 g, 21.3 mmol). Yield 7.94 g (19.3 mmol, 91%), $^1$H NMR (DMSO-d$_6$) δ 7.95 (s, 1H, H-8), 6.86 (bs, 2H, NH$_2$), 5.97–5.89 (m, 1H, H-1'), 5.97–5.89 (m, 1H, H-2'), 5.30 (pq, J=3.26 Hz, 1H, H-3'), 4.21 (pq, J=3.12 Hz, 1H, H-4'), 3.00–2.90 (m, 2H, H-5'), 2.52 (pq, J=7.45 Hz, 2H, CH$_2$), 2.10, 1.99 (2×s, 6H, 2×COCH$_3$), 1.13 (t, J=7.42 Hz, 3H, CH$_3$).

2',3'-di-O-Acetyl-5'-deoxy-5'-propylthioguanosine (compound 23). The reaction was carried out with 5'-deoxy-5'-propylthioguanosine (19, 5.74 g, 16.8 mmol). Yield 5.71 g (13.4 mmol, 80%), $^1$H NMR (DMSO-d$_6$) δ 10.71 (bs, 1H, NH), 7.97 (s, 1H, H-8), 6.55 (bs, 2H, NH$_2$), 5.95 (m, 1H, H-1'), 5.95 (m, 1H, H-2'), 5.41 (m, 1H, H-3'), 4.20 (m, 1H, H-4'), 2.95 (d, J=5.83 Hz, 2H, H-5'), 2.49 (m, 2H, SCH$_2$), 2.11, 1.99 (2×s, 6H, 2×COCH$_3$), 1.49 (q, J=6.86 Hz, 2H, CH$_2$CH$_3$), 0.86 (t, J=6.18 Hz, 3H, CH$_3$).

2',3'-di-O-Acetyl-5'-deoxy-5'-isopropylthioguanosine (compound 24). The reaction was carried out with 5'-deoxy-5'-isopropylthioguanosine (20, 6.64 g, 19.5 mmol). Yield 6.92 g (16.3 mmol, 83%), $^1$H NMR (DMSO-d$_6$) δ 10.80 (bs, 1H, NH), 7.98 (s, 1H, H-8), 6.58 (bs, 2H, NH$_2$), 5.94–5.90 (m, 1H, H-1'), 5.94–5.90 (m, 1H, H-2'), 5.42 (t, J=4.12 Hz, 1H, H-3'), 4.25–4.12 (m, 1H, H-4'), 2.99–2.93 (m, 3H, CH, H-5'), 2.10, 2.00 (2×s, 6H, 2×COCH$_3$), 1.16 (d, J=6.18 Hz, 6H, 2×CH$_3$).

General chlorination procedure of derivatives 21–24 to obtain compounds 25–28. To a suspension of the appropriate 2',3'-di-O-acetyl-5'-alkylthio-5'-deoxyguanosine (19.3 mmol, predried) and tetraethylammonium chloride (6.48 g, 39.1 mmol; pre-dried in vacuo at 80° C.) in acetonitrile (40 ml) were added N,N-dimethylaniline (2.52 ml, 20.0 mmol, dried and distilled from KOH), and phosphoryl chloride ($POCl_3$, 10.95 ml, 0.12 mol, freshly distilled) at room temperature. The flask was placed in an oil bath preheated at 100° C. and the solution was refluxed for 10–15 minutes. Volatile materials were evaporated immediately in vacuo. The resulting yellow foam was dissolved in $CH_2Cl_2$ (100 ml) and stirred vigorously for 15 minutes with crushed ice. The layers were separated and the aqueous phase was extracted with $CH_2Cl_2$ again (75 ml). The combined organic layers were kept cold by addition of crushed ice and washed with cold water (3×75 mL), 5% $NaHCO_3/H_2O$ to pH 7, dried over $MgSO_4$ and filtered. The residue was purified by column chromatography.

2-Amino-6-chloro-9-(2,3-di-O-acetyl-5-deoxy-5-methylthio-β-D-ribofuranosyl)-purine (compound 25). The reaction was carried out with 2',3'-di-O-acetyl-5'-deoxy-5'-methylthioguanosine (21, 5.96 g, 15.0 mmol). The mixture was purified by column chromatography (eluens EtOAc:PE40/60=1:1 to 2:1).

Yield 3.83 g (9.21 mmol, 62%), $R_f$ 0.28 EtOAc: PE40/60=2:1). $^1H$ NMR DMSO-$d_6$) δ 8.40 (s, 1H, H-8), 7.08 (bs, 2H, $NH_2$), 6.10–5.99 (m, 2H, H-1', H-2'), 5.49–5.45 (m, 1H, H-3'), 4.31–4.24 (m, 1H, H-4'), 2.96 (pd, J=6.86 Hz, 2H, H-5'), 2.12, 2.06 (2×s, 6H, $COCH_3$), 1.97 (s, 3H, $SCH_3$).

2-Amino-6-chloro-9-(2,3-di-O-acetyl-5-deoxy-5-ethylthio-β-D-ribofuranosyl)-purine (compound 26). The reaction was carried out with 2',3'-di-O-acetyl-5'-deoxy-5'-ethylthioguanosine (22, 7.94 g, 19.3 mmol). The mixture was purified by column chromatography (eluens EtOAc:PE40/60=3:2). Yield 4.23 g (9.84 mmol, 51%), $R_f$ 0.51 (EtOAc: PE40/60=2:1). $^1H$ NMR (DMSO-$d_6$) δ 8.41 (s, 1H, H-8), 7.09 (bs, 2H, $NH_2$), 6.07 (d, J=6.75 Hz, 1H, H-1'), 6.01 (q, J=6.72 Hz, 1H, H-2'), 5.46 (dd, J=5.47 Hz, J=3.21 Hz, 1H, H-3'), 4.26 (dt, J=6.65 Hz, J=3.20 Hz, 1H, H-4'), 2.98 (pd, J=7.35 Hz, 2H, H-5'), 2.52 (q, J=7.58 Hz, 2H, $CH_2$), 2.12, 1.99 (2×s, 6H, 2×$COCH_3$), 1.12 (t, J=4.79 Hz, 3H, $CH_3$).

2-Amino-6-chloro-9-(2,3-di-O-acetyl-5-deoxy-5-propylthio-β-D-ribofuranosyl)-purine (compound 27). The reaction was carried out with 2',3'-di-O-acetyl-5'-deoxy-5'-propylthioguanosine (23, 5.71 g, 13.4 mmol). The mixture was purified by column chromatography (eluens EtOAc:PE40/60=1:1). Yield 4.41 g (9.91 mmol, 74%), $R_f$ 0.44 (EtOAc:PE 40/60=2:1). $^1H$ NMR (DMSO-$d_6$) δ 8.40 (s, 1H, H-8), 7.08 (bs, 2H, $NH_2$), 6.10–5.99 (m, 2H, H-1', H-2'), 5.46 (pt, J=3.09 Hz, 1H, H-3'), 4.25 (pq, J=3.09 Hz, 1H, H-4'), 2.97 (d, J=6.52 Hz, 2H, H-5'), 2.49 (m, 2H, $SCH_2$), 2.12, 1.99 (2×s, 6H, 2×$COCH_3$), 1.47 (pq, J=7.55 Hz, $CH_2CH_3$), 0.84 (t, J=7.21 Hz, 3H, $CH_3$).

2-Amino-6-chloro-9-(2,3-di-O-acetyl-5-deoxy-5-isopropylthio-β-D-ribofuranosyl)-purine (compound 28). The reaction was carried out with 2',3'-di-O-acetyl-5'-deoxy-5'-isopropylthioguanosine (24, 6.72 g, 15.8 mmol). The mixture was purified by column chromatography (eluens EtOAc:PE40/60=1:1). Yield 5.20 g (11.7 mmol, 74%), $R_f$ 0.39 (EtOAc:PE40/60=2:1). $^1H$ NMR (DMSO-$d_6$) δ 8.40 (s, 1H, H-8), 7.07 (bs, 2H, $NH_2$), 6.09–5.96 (m, 2H, H-1', H-2'), 5.48–5.44 (m, 1H, H-3'), 4.25–4.23 (m, 1H, H-4'), 3.01–2.92 (m, 2H, H-5'), 3.01–2.92 (m, 1H, CH), 2.12, 1.99 (2×s, 6H, 2×$COCH_3$), 1.15 (d, J=6.53 Hz, 6H, 2×$CH_3$).

General diazotization method of derivatives 25–28 to obtain compounds 29–32. Isopentylnitrite (23.2 mmol, 3.10 ml) was added to a mixture of the appropriate 2-amino-6-chloro-9-(2,3-di-O-acetyl-5-aklylthio-5-deoxy-δ-D-ribofuranosyl)-purine (7.49 mmol), $I_2$ (7.49 mmol, 1.90 g), $CH_2I_2$ (77.5 mmol, 6.24 ml) and CuI (7.87 mmol, 1.50 g) in 40 mL tetrahydrofuran. The dark brown solution was refluxed (under intensive cooling) for 40–60 minutes and then cooled to room temperature. The mixture was filtered and the filtrate was concentrated in vacuo. The residue was dissolved in $CH_2Cl_2$ and extracted with a saturated $Na_2S_2O_3$ solution, until tie colour disappeared. The organic layer was dried and concentrated. The brownish oil was purified by column chromatography.

6-Chloro-2-iodo-9-(2,3-di-O-acetyl-5-deoxy-5-methylthio-β-D-ribofuranosyl)-purine (compound 29). The reaction was carried out with 2-amino-6-chloro-9-(2,3-di-O-acetyl-5-deoxy-5-methylthio-β-D-ribofuranosyl)-purine (25, 3.83 g, 9.21 mmol). The mixture was purified by column chromatography (eluens $CH_2Cl_2$—5% MeOH in $CH_2Cl_2$). Yield 3.99 g (7.58 mmol, 82%), $R_f$ 0.62 (5% MeOH in $CH_2Cl_2$); $^1H$ NMR (DMSO-$d_6$) δ 8.84 (s, 1H, H-8), 6.27 (d, J=5.49 Hz, 1H, H-1'), 5.96 (t, J=5.49 Hz, 1H, H-2'), 5.58 (t, J=5.49 Hz, 1H, H-3'), 4.37–4.32 (m, 1H, H-4'), 2.98 (d, J=6.86 Hz, 2H, H-5'), 2.12, 2.07 (2×s, 6H, 2×$COCH_3$), 2.02 (s, 3H, $SCH_3$).

6-Chloro-2-iodo-9-(2,3-di-O-acetyl-5-deoxy-5-methylthio-β-D-ribofuranosyl)-purine (compound 30). The reaction was carried out with 2-amino-6-chloro-9-(2,3-di-O-acetyl-5-deoxy-5-ethylthio-β-D-ribofuranosyl)-purine (26, 3.22 g, 7.49 mmol). The mixture was purified by column chromatography (eluens $CH_2Cl_2$). Yield 2.88 g (5.33 mmol, 71%), $R_f$ 0.71 (5% MeOH in $CH_2Cl_2$); $^1H$ NMR (DMSO-$d_6$) δ 8.48 (s, 1H, H-8), 5.91 (d, J=5.49 Hz, 1H, H-1'), 5.61 (t, J=5.49 Hz, 1H, H-2'), 5.22 (t, J=4.80 Hz, 1H, H-3'), 3.97 (q, J=3.77 Hz, 1H, H-4'), 2.65 (d, J=6.87 Hz, 2H, H-5'), 2.49 (q, J=7.21 Hz, 2H, $CH_2$), 1.76, 1.66 (2×s, 6H, 2×$COCH_3$), 0.77 (t, J=7.20 Hz, 3H, $CH_3$).

6-Chloro-2-iodo-9-(2,3-di-O-acetyl-5-deoxy-5-propylthio-β-D-ribofuranosyl)-purine (compound 31). The reaction was carried out with 2-amino-6-chloro-9-(2,3-di-O-acetyl-5-deoxy-5-propylthio-β-D-ribofuranosyl)-purine (27, 4.41 g, 9.91 mmol). The mixture was purified by column chromatography (eluens EtOAc:PE40/60=1:1) Yield 4.02 g (7.23 mmol, 73%), $R_f$ 0.50 (EtOAc:PE40/60=2:1); $^1H$ NMR (DMSO-$d_6$) δ 8.83 (s, 1H, H-8), 6.27 (d, J=5.49 Hz, 1H, H-1'), 5.97 (t, J=5.49 Hz, 1H, H-2'), 5.58 (t, J=5.15 Hz, 1H, H-3'), 4.32 (q, J=3.77 Hz, 1H, H-4'), 2.99 (d, J=6.53 Hz, 2H, H-5'), 2.12, 2.02 (2×s, 6H, 2×$COCH_3$), 1.54–1.43 (m, 4H, $CH_2CH_2$), 0.84 (t, J=7.21 Hz, 3H, $CH_3$).

6-Chloro-2-iodo-9-(2,3-di-O-acetyl-5-deoxy-5-isopropylthio-β-D-ribofuranosyl)-purine (compound 32). The reaction was carried out with 2-amino-6-chloro-9-(2,3-di-O-acetyl-5-deoxy-5-isopropylthio-β-D-ribofuranosyl)-purine (28, 5.20 g, 11.7 mmol). The mixture was purified by column chromatography (eluens EtOAc:PE 40/60=1:1).). Yield 4.88 g (8.76 mmol, 75%/O), $R_f$ 0.47 (EtOAc:PE40/60=2:1); $^1H$ NMR (DMSO-$d_6$) δ 8.82 (s, 1H, H-8), 6.26 (d, J=5.49 Hz, 1H, H-1'), 5.96 (t, J=5.49 Hz, 1H, H-2'), 5.59 (t, J=5.20 Hz, 1H, H-3'), 4.31 (pt J=5.15 Hz, 1H, H-4'), 3.02–2.95 (m, 2H, H-5'), 3.02–2.95 (m, 1H, CH), 2.11, 2.02 (2×s, 6H, 2×$COCH_3$), 1.16 (d, J=4.80 Hz, 6H, 2×$CH_3$).

General procedure for $N^6$-amination and deprotection of derivatives 29–32 to obtain 33–36. The appropriate 6-chloro-2-iodo-9-(2,3-di-O-acetyl-5-alkylthio-5-deoxy-β-D-ribofuranosyl)-purine (5.33 mmol) was stirred with 50 mL $EtOH/NH_3$ for 64 h. The mixture was concentrated and purified by column chromatography.

5'-Deoxy-2-iodo-5'-methylthioadenosine (compound 33). The reaction was carried out with 6-chloro-2-iodo-9-(2,3-di-O-acetyl-5-deoxy-5-methylthio-β-D-ribofuranosyl)-purine (29, 3.99 g, 7.58 mmol). The mixture was purified by column chromatography (10% MeOH in $CH_2Cl_2$). Yield 2.21 g (5.22 mmol, 69%), mp 90–93÷C; $R_f$ 0.24 (10% MeOH in $CH_2Cl_2$). The product was recrystallized from EtOAc; $^1H$ NMR (DMSO-$d_6$) δ 8.29 (s, 1H, H-8), 7.71 (bs, 2H, $NH_2$), 5.79 (d, J=5.84 Hz, 1H, H-1'), 5.52 (d, J=6.52 Hz, 1H, OH-2'), 5.35 (d, J=5.80 Hz, 1H, OH-3'), 4.69 (m, 1H, H-2'), 4.11–4.02 (m, 1H, H-3'), 4.11–4.02 (m, 1H, H-4'), 2.85–2.80 (m, 2H, H-5'), 2.06 (s, 3H, $SCH_3$); MS m/z 424 (M+H)$^+$; Anal. ($C_{11}H_{14}IN_5O_3S$.0.35 EtOAc) C, H, N.

5'-Deoxy-2–5'-ethylthioiodoadenosine (compound 34). The reaction was carried out with 6-chloro-2-iodo-9-(2,3-di-O-acetyl-5-deoxy-5-ethylthio-β-D-ribofuranosyl)-purine (30, 2.88 g, 5.33 mmol). The mixture was purified by column chromatography (eluens EtOAc). Yield 2.05 g (4.69 mmol, 88%), mp 76–79÷C; $R_f$ 0.15 (5% MeOH in $CH_2Cl_2$); $^1H$ NMR (DMSO-$d_6$) δ 8.29 (s, 1H, H-8), 7.27 (bs, 2H, $NH_2$), 5.79 (d, J=6.18 Hz, 1H, H-1'), 5.50 (d, J=6.18 Hz, 1H, OH-2'), 5.34 (d, J=4.80 Hz, 1H, OH-3'), 4.69 (q, J=5.15 Hz, 1H, H-2'), 4.11–4.07 (m, 1H, H-3'), 4.07–3.96 (m, 1H, H-4'), 2.86 (pt, J=5.84 Hz, 2H, H-5'), 2.53 (q, J=7.21 Hz, 2H, $CH_2$), 1.98, 1.74 (2×s, 6H, 2×$COCH_3$), 1.14 (t, J=7.21 Hz, 3H, $CH_3$), MS m/z 438 (M+H)$^+$; Anal. ($C_{12}H_{16}IN_5O_3S$) C, H, N.

5'-Deoxy-2-iodo-5'-propylthioadenosine (compound 35). The reaction was carried out with 6-chloro-2-iodo-9-(2,3-di-O-acetyl-5-deoxy-5-propylthio-δ-D-ribofuranosyl)-purine (31, 4.02 g, 7.23 mmol). The mixture was purified by column chromatography (eluens 10% MeOH in $CH_2Cl_2$). Yield 2.35 g (5.21 mmol, 72%), mp 98–101÷C; $R_f$ 0.30 (10% MeOH in $CH_2Cl_2$); $^1H$ NMR (DMSO-$d_6$) δ 8.30 (s, 1H, H-8), 7.73 (bs, 2H, $NH_2$), 5.71 (d, J=6.18 Hz, 1H, H-1'), 5.52 (d, J=6.18 Hz, 1H, OH-2'), 5.35 (d, J=5.15 Hz, 1H, OH-3'), 4.72 (q, J=5.15 Hz, 1H, H-2'), 4.15–4.08 (m, 1H, H-3'), 4.08–3.96 (m, 1H, H-4'), 2.86 (pt, J=5.84 Hz, 2H, H-5'), 2.49–2.46 (m, 2H, $SCH_2$), 1.51 (q, J=7.21 Hz, 2H, $CH_2CH_3$), 0.87 (t, J=7.21 Hz, 3H, $CH_3$); MS m/z 452 (M+H)$^+$; Anal. ($C_{13}H_{18}IN_5O_3S$) C, H, N.

5'-Deoxy-2-iodo-5'-isopropylthioadenosine (compound 36). The reaction was carried out with 6-chloro-2-iodo-9-(2,3-di-O-acetyl-5-deoxy-5-isopropylthio-β-D-ribofuranosyl)-purine (32, 4.88 g, 8.76 mmol). The mixture was purified by column chromatography (eluens 10% MeOH in $CH_2Cl_2$). Yield 2.77 g (6.13 mmol, 70%), mp 102–104÷C; $R_f$ 0.33 (10% MeOH in $CH_2Cl_2$). The product was recrystallised from EtOAc; $^1H$ NMR (DMSO-$d_6$) δ 8.29 (s, 1H, H-8), 7.71 (bs, 2H, $NH_2$), 5.79 (d, J=6.18 Hz, 1H, H-1'), 5.50 (d, J=5.83 Hz, 1H, OH-2'), 5.34 (d, J=4.80 Hz, 1H, OH-3'), 4.69 (q, J=5.49 Hz, 1H, H-2'), 4.10 (pq, J=3.43 Hz, 1H, H-3'), 3.97 (pq, J=3.44 Hz, 1H, H-4'), 2.97–2.82 (m, 2H, H-5'), 2.97–2.87 (m, 1H, CH), 1.17 (d, J=6.52 Hz, 6H, 2×$CH_3$); MS m/z 452 (M+H)$^+$; Anal. ($C_{13}H_{18}IN_5O_3S$0.11 EtOAc) C, H, N.

General procedure for the introduction of a 1-hexyn group at derivatives 1 and 33–36, to obtain 4 and 37–40. To a solution of the appropriate 5'-alkylthio-5'-deoxy-2-iodoadenosine (0.92 mmol) in 7 ml dry acetonitrile and 7 ml triethylamine under a nitrogen atmosphere was added CuI (0.07 mmol, 13.3 mg), $PdCl_2$ (0.05 mmol, 8.47 mg) and $Ph_3P$ (0.1.1 mmol). To the suspension was added 1-hexyn (4.45 mmol, 511 µl) and the mixture was stirred overnight under nitrogen atmosphere. The light brown solution was filtered and concentrated. The residue was extracted with water and EtOAc (3×50 ml), the organic layer was dried, concentrated and purified by column chromatography.

2-Iodoadenosine (1). was prepared according to literature.[18] Yield 80%; mp 185–187÷C; $R_f$ 0.21 (10% MeOH in $CH_2Cl_2$).

2-(1-Hexynyl)adenosine (4).[8] The reaction was carried out with 2-iodoadenosine (1, 440 mg, 1.12 mmol). The mixture was purified by column chromatography (eluens $CH_2Cl_2$ to 10% MeOH in $CH_2Cl_2$). Yield 330 mg (0.95 mmol, 85%), mp 106–109÷C; $R_f$ 0.10 (10% MeOH in $CH_2Cl_2$). The product was re-crystallized from $CH_2Cl_2$; $^1H$ NMR (DMSO-$d_6$) δ 8.37 (s, 1H, H-8), 7.41 (bs, 2H, $NH_2$), 5.84 (d, J=6.18 Hz, 1H, H-1'), 5.45 (d, J=6.18 Hz, 1H, OH-2'), 5.22–5.16 (m, 1H, OH-5'), 5.22–5.16 (m, 1H, OH-3'), 4.52 (q, J=5.15 Hz, 1H, H-2'), 4.11 (q, J=3.43 Hz, 1H, H-3'), 3.93 (pd, J=3.43 Hz, 1H, H-4'), 3.65–3.48 (m, 2H, H-5'), 2.39 (t, J=6.86 Hz, 2H, ≡$CCH_2$), 1.51–1.39 (m, 4H, $CH_2CH_2$), 0.90 (t, J=6.87 Hz, 3H, $CH_3$); MS m/z 348 (M+H)$^+$; Anal. ($C_{16}H_{21}N_5O_4$.0.22$CH_2Cl_2$) C, H, N.

5'-Deoxy-2-(1-hexynyl)-5'-methylthioadenosine (compound 37). The reaction was carried out with 5'-deoxy-2-iodo-5'-methylthioadenosine (33, 480 mg, 1.13 mmol). The mixture was purified by column chromatography (eluens $CH_2Cl_2$ to 10% MeOH in $CH_2Cl_2$). Yield 257 mg (0.68 mmol, 60%); mp 64–67÷C; $R_f$ 0.28 (10% MeOH in $CH_2Cl_2$). The product was re-crystallized from methanol; $^1H$ NMR (DMSO-$d_6$) δ 8.37 (s, 1H, H-8), 7.39 (s, 2H, $NH_2$), 5.85 (d, J=6.18 Hz, 1H, H-1'), 5.49 (d, J=6.18 Hz, 1H, OH-2'), 5.32 (d, J=4.81 Hz, 1H, OH-3'), 4.67 (q, J=5.49 Hz, 1H, H-2'), 4.12–3.95 (m, 1H, H-3'), 4.12–3.95 (m, 1H, H-4'), 2.84 (t, J=5.49 Hz, 2H, H-5'), 2.40 (t, J=6.68 Hz, 2H,≡$CCH_2$), 2.05 (s, 3H, $SCH_3$), 1.55-1.32 (m, 4H, ≡$CCH_2CH_2CH_2$), 0.90 (t, J=6.18 Hz, 3H, $CH_3$); MS m/z 378 (M+H)$^+$; Anal. ($C_{17}H_{23}N_5O_3S$0.56 $CH_3OH$) C, H, N.

5'-Deoxy-2-(1-hexynyl)-5'-ethylthioadenosine (compound 38). The reaction was carried out with 5'-deoxy-5'-ethylthio-2-iodoadenosine (34, 400 mg, 0.92 mmol). The mixture was purified by column chromatography (eluens $CH_2Cl_2$ to 10% MeOH in $CH_2Cl_2$). Yield 161 mg (0.41 mmol, 45%); mp 72–75÷C; $R_f$ 0.38 (10% MeOH in $CH_2Cl_2$). The product was re-crystallized from $CH_2Cl_2$; $^1H$ NMR (DMSO-$d_6$) δ 8.38 (s, 1H, H-8), 7.39 (s, 2H, $NH_2$), 5.85 (d, J=6.18 Hz, 1H, H-1'), 5.49 (d, J=6.52 Hz, 1H, OH-2'), 5.32 (d, J=4.81 Hz, 1H, OH-3'), 4.71–4.69 (m, 1H, H-2'), 4.11–4.00 (m, 1H, H-3'), 4.11–4.00 (m, 1H, H-4'), 2.85 (pd, J=7.55 Hz, 2H, H-5'), 2.49–2.40 (m, 2H, $SCH_2$), 2.49–2.40 (m, 2H, ≡$CCH_2$), 1.52–1.43 (m, 4H, ≡$CCH_2CH_2CH_2$), 1.14 (t, J=7.20 Hz, 3H, $SCH_2CH_3$), 0.90 (t, J=7.21 Hz, 3H, $CH_3$), MS m/z 392 (M+H)$^+$; Anal. ($C_{18}H_{25}N_5O_3S$.0.14 $CH_2Cl_2$) C, H, N.

5'-Deoxy-2-(1-hexynyl)-5'-propylthioadenosine (compound 39). The reaction was carried out with 5'-deoxy-2-iodo-5'-propylthioadenosine (35, 500 mg, 1.11 mmol). The mixture was purified by column chromatography (eluens $CH_2Cl_2$ to 10% MeOH in $CH_2Cl_2$). Yield 320 mg (0.79 mmol, 71%), mp 68–71÷C; $R_f$ 0.30 (5% MeOH in $CH_2Cl_2$). The product was re-crystallized from $CH_2Cl_2$; $^1H$ NMR (DMSO-$d_6$) δ 8.38 (s, 1H, H-8), 7.39 (s, 2H, $NH_2$), 5.86 (d, J=6.18 Hz, 1H, H-1'), 5.50 (d, J=5.83 Hz, 1H, OH-2'), 5.31 (d, J=4.81 Hz, 1H, OH-3'), 4.73 (q, J=5.15 Hz, 1H, H-2'), 4.10 (pq, J=4.81 Hz, 1H, H-3'), 4.01–3.99 (m, 1H, H-4'), 2.86 (pt, J=5.26 Hz, 2H, H-5'), 2.49–2.41 (m, 2H, ≡$CCH_2$), 249–2.41 (m, 2H, $SCH_2$), 1.61–1.44 (m, 4H, ≡$CCH_2CH_2CH_2$), 1.61–1.44 (m, 2H, $SCH_2CH_2$), 0.94–0.83 (m, 6H, 2×$CH_3$); MS m/z 406 (M+H)$^+$; Anal. ($C_{19}H_{27}N_5O_3S$0.12 $CH_2Cl_2$) C, H, N.

5'-Deoxy-2-(1-hexynyl)-5'-isopropylthioadenosine (compound 40). The reaction was carried out with 5'-deoxy-2-iodo-5'-isopropylthioadenosine (36, 500 mg, 1.11 mmol).

The mixture was purified by column chromatography (eluens $CH_2Cl_2$ to 10% MeOH in $CH_2Cl_2$). Yield 306 mg (0.75 mmol, 68%), mp 77–81÷C; $R_f$ 0.28 (5% MeOH in $CH_2Cl_2$). The product was re-crystallized from $CH_2Cl_2$; $^1$H NMR (DMSO-$d_6$) δ 8.39 (s, 1H, 1H-8), 7.40 (bs, 2H, $NH_2$), 5.86 (d, J=5.84 Hz, 1H, H-1'), 5.50 (d, J=6.17 Hz, 1H, OH-2'), 5.32 (d, J=4.81 Hz, 1H, OH-3'), 4.74 (q, J=5.83 Hz, 1H, H-2'), 4.12 (pq, J=3.77 Hz, 1H, H-3'), 4.09–3.98 (m, 1H, H-4'), 2.95–2.88 (m, 2H, H-5'), 2.95–2.88 (m, 1H, CH), 2.40 (t, J=6.52 Hz, 2H, =$CCH_2$), 1.53–1.45 (m, 4H, $CH_2CH_2$), 1.18 (d, J=6.86 Hz, 6H, $(CH_3)_2$), 0.91 (t, J=7.21 Hz, 3H, $CH_3$); MS m/z 406 (M+H)$^+$; Anal. ($C_{19}H_{27}N_5O_3S$.0.17 $CH_2Cl_2$) C, H, N.

General method for the introduction of a 2-hydrazino group at derivatives 1 and 33–36 to obtain 2 and 41–44. A pressure tube was charged with the appropriate 5'-alkylthio-5'-deoxy-2-iodoadenosine (1.37 mmol) and 10 ml isopropanol. To the obtained suspension hydrazine monohydrate (14.0 mmol, 678 µl) in 1 ml isopropanol was added. The mixture was heated to 80° C. and after 30 minutes a clear solution was obtained. The solution was heated overnight at 80° C. A white precipitate had appeared and the mixture was cooled to room temperature under vigorous stirring. The white powder was filtered and dried.

2-Hydrazinoadenosine (2).[7] The reaction was carried out with 2-iodoadenosine (1, 500 mg, 1.27 mmol). Yield 310 mg (1.04 mmol, 82%), $^1$H NMR (DMSO-$d_6$) δ 7.95 (s, 1H, H-8), 7.29 (bs, 1H, NH), 6.87 (bs, 2H, $NH_2$), 5.78 (d, J=6.18 Hz, 1H, H-1'), 5.43–5.29 (m, 1H, OH-2'), 5.29–5.05 (m, 1H, OH-5'), 5.29–5.05 (m, 1H, OH-3'), 4.59–4.56 (m, 1H, H-2'), 4.14–4.11 (m, 1H, H-3'), 3.91–3.89 (m, 1H, H-4'), 3.63–3.54 (m, 2H, H-5').

5'-Deoxy-2-hydrazino-5'-methylthioadenosine (compound 41). The reaction was carried out with 5'-deoxy-2-iodo-5'-methylthioadenosine (33, 540 mg, 1.28 mmol). Yield 240 mg (0.73 mmol, 57%), $^1$H NMR (DMSO-$d_6$) δ 7.94 (s, 1H, H-8), 7.30 (bs, 1H, NH), 6.82 (bs, 2H, $NH_2$), 5.77 (d, J=5.83 Hz, 1H, H-1'), 4.70 (t, J=5.83 Hz, 1H, H-2'), 4.13 (t, J=3.78 Hz, 1H, H-3'), 4.01–3.92 (m, 1H, H-4'), 2.81 (t, J=7.20 Hz, 2H, H-5'), 2.04 (s, 3H, $SCH_3$).

5'-Deoxy-2-hydrazino-5'-ethylthioadenosine (compound 42). The reaction was carried out with 5'-deoxy-2-iodo-5'-ethylthioadenosine (34, 600 mg, 1.37 mmol). Yield 358 mg (1.05 mmol, 76%), $^1$H NMR (DMSO-$d_6$) δ 7.94 (s, 1H, H-8), 7.31 (bs, 1H, NH), 6.83 (bs, 2H, $NH_2$), 5.77 (d, J=5.83 Hz, 1H, H-1'), 4.69 (t, J=5.49 Hz, 1H, H-2'), 4.13 (t, J=4.11 Hz, 1H, H-3'), 3.95–3.93 (m, 1H, H-4'), 2.84 (t, J=6.52 Hz, 2H, H-5'), 2.49–2.47 (m, 2H, $SCH_2$), 1.13 (t, J=7.56 Hz, 3H, $CH_3$).

5'-Deoxy-2-hydrazino-5'-propylthioadenosine (compound 43). The reaction was carried out with 5'-deoxy-2-iodo-5'-propylthioadenosine (35, 700 mg, 1.55 mmol). Yield 468 mg (1.32 mmol, 85%), $^1$H NMR (DMSO-$d_6$) δ 7.95 (s, 1H, H-8), 7.31 (bs, 1H, NH), 6.84 (bs, 2H, $NH_2$), 5.77 (d, J=5.15 Hz, 1H, H-1'), 4.71 (t, J=5.84 Hz, 1H, H-2'), 4.20–4.10 (m, 1H, H-3'), 4.07–3.91 (m, 1H, H-4'), 2.83 (pt, J=6.18 Hz, 2H, H-5'), 2.49–2.44 (m, 2H, $SCH_2$), 1.50 (pq, J=7.20 Hz, 2H, $CH_2CH_3$), 0.88 (t, J=7.55 Hz, 3H, $CH_3$).

5'-Deoxy-2-hydrazino-5'-isopropylthioadenosine (compound 44). The reaction was carried out with 5'-deoxy-2-iodo-5'-isopropylthioadenosine (36, 700 mg, 1.55 mmol). Yield 452 mg (1.27 mmol, 82%), $^1$H NMR (DMSO-$d_6$) δ 7.97 (s, 1H, H-8), 7.37 (bs, 1H, NH), 6.86 (bs, 2H, $NH_2$), 5.78 (d, J=5.49 Hz, 1H, H-1'), 4.70 (t, J=5.49 Hz, 1H, H-2'), 4.16 (t, J=4.46 Hz, 1H, H-3'), 3.95 (q, J=3.78 Hz, 1H, H-4'), 3.06–2.77 (m, 2H, H-5'), 3.06–2.77 (m, 1H, CH), 1.17 (d, J=6.86 Hz, 6H, 2×$CH_3$).

General procedure to convert the 2-hydrazino group of derivatives 2 and 41–44, into a 2-(N'-3-methyl-1-butyl-idenehydrazino) group in derivatives 3 and 45–48. A pressure tube was charged with the appropriate 5'-deoxy-2-hydrazino-5'-alkylthioadenosine (1.05 mmol) and 8 ml methanol. 1.2 Molar equivalents (1.40 mmol, 146 µl) isovaleraldehyde were added and the mixture was refluxed for 1.8 h. The mixture was concentrated in vacuo and purified by column chromatography.

2-(N'-3-Methyl-1-butylidenehydrazino)adenosine (compound 3).[7] The reaction was carried out with 2-hydrazinoadenosine (2, 310 mg, 1.04 mmol). Yield 274 mg (0.75 mmol, 72%), mp 176–179÷C; $R_f$ 0.20 (10% MeOH in $CH_2Cl_2$). The product was recrystallised from MeOH; $^1$H NMR (MeOD) δ 8.02 (s, 1H, H-8), 7.34 (t, J=6.18 Hz, 1H, N=CH), 5.93 (d, J=5.84 Hz, 1H, H-1'), 4.67 (t, J=5.49 Hz, 1H, H-2'), 4.34–4.30 (m, 1H, H-3'), 4.14 (q, J=3.09 Hz, 1H, H-4'), 3.81 (dq, J=16.82 Hz, J=3.09 Hz, 2H, H-5'), 2.26–2.17 (m, 2H, $CH_2$), 1.89–1.83 (m, 1H, $CH(CH_3)_2$), 0.99 (d, J=6.87 Hz, 6H, $(CH_3)_2$); MS m/z 366 (M+H)$^+$; Anal. ($C_{15}H_{23}N_7O_4$.0.54 $CH_3OH$) C, H, N.

5'-Deoxy-2-(N-3'-methyl-1-butylidenehydrazino)-5'-methylthioadenosine (compound 45). The reaction was carried out with 5'-deoxy-2-hydrazino-5'-methylthioadenosine (41, 240 mg, 0.73 mmol). The mixture was purified by column chromatography (eluens 10% MeOH in $CH_2Cl_2$). Yield 210 mg (0.53 mmol, 73%), mp 122–125÷C; $R_f$ 0.25 (10% MeOH in $CH_2Cl_2$). The product was recrystallized from $CH_2Cl_2$; $^1$H NMR (DMSO-$d_6$) δ 10.02 (bs, 1H, NH), 7.98 (s, 1H, H-8), 7.33 (t, J=5.49 Hz, 1H, N=CH), 6.91 (bs, 2H, $NH_2$), 5.77 (d, J=6.17 Hz, 1H, H-1'), 5.49–5.41 (m, 1H, OH-2'), 5.24–5.22 (m, 1H, OH-3'), 4.75–4.71 (m, 1H, H-2'), 4.10–4.05 (m, 1H, H-3'), 4.05–3.95 (m, 1H, H-4'), 2.91–2.83 (m, 2H, H-5'), 2.91–2.83 (m, 1H, $CH(CH_3)_2$), 2.12–2.08 (m, 2H, $CH_2$), 2.04 (s, 3H, $SCH_3$), 0.91 (t, J=6.87 Hz, 6H, $CH_3$), MS m/z 396 (M+H)$^+$; Anal. $C_{16}H_{25}N_7O_3S$0.33 $CH_2Cl_2$) C, H, N.

5'-Deoxy-2-(N'-3-methyl-1-butylidenehydrazino)-5'-ethylthioadenosine compound 46). The reaction was carried out with 5'-deoxy-2-hydrazino-5'-ethylthioadenosine (42, 358 mg, 1.05 mmol). The mixture was purified by column chromatography (eluens 10% MeOH in $CH_2Cl_2$). Yield 193 mg (0.47 mmol, 45%), mp 106–109÷C; $^1$H NMR (DMSO-$d_6$) δ10.32 (bs, 1H, NH), 8.02 (s, 1H, H-8), 7.25–7.09 (m, 1H, N=CH), 6.91 (bs, 2H, $NH_2$), 5.79 (d, J=6.16 Hz, 1H, H-1'), 5.50–5.36 (m, 1H, OH-2'), 5.28–5.16 (m, 1H, OH-3'), 4.79–4.68 (m, 1H, H-2'), 4.19–4.11(m, 1H, H-3'), 4.06–3.95 (m, 1H, H-4'), 2.98–2.80 (m, 3H, H-5', $CH(CH_3)_2$), 2.49–2.47 (m, 2H, $SCH_2$), 2.11 (t, J=6.41 Hz, 2H, $CHCH_2$), 1.15 (t, J=9.30 Hz, 3H, $SCH_2CH_3$), 0.94–0.83 (m, 6H, 2×$CH_3$); MS m/z 410 (M+H)$^+$; HPLC Alltima C18 5u column (150 mm×4.6 mm) Reversed phase, flow 1 mL/min. System A: 20–100% MeOH in $H_2O$ in 40 min.; retention time: 25.31 min. System B: 20–100% $CH_3CN$ in $H_2O$ in 35 min.; retention time: 5.59 min.

5'-Deoxy-2-(N'-3-methyl-1-butylidenehydrazino)-5'-propylthioadenosine (compound 47). The reaction was carried out with 5'-deoxy-2-hydrazino-5'-propylthioadenosine (43, 468 mg, 1.32 mmol). The mixture was purified by column chromatography (eluens 10% MeOH in $CH_2Cl_2$). Yield 364 mg (0.86 mmol, 65%), mp 150–152÷C; $^1$H NMR (DMSO-$d_6$) δ 10.02 (bs, 1H, NH), 7.98 (s, 1H, H-8), 7.34 (t, J=5.80 Hz, 1H, N=CH), 6.91 (bs, 2H, $NH_2$), 5.76 (d, J=6.16 Hz, 1H, H-1'), 5.43 (pd, J=4.55 Hz, 1H, OH-2'), 5.21–5.19 (m, 1H, OH-3'), 4.75 (q, J=5.28 Hz, 1H, H-2'), 4.11 (pq, J=3.25 Hz, 1H, H-3'), 3.96 (pq, J=2.76 Hz, 1H, H-4'), 2.96–2.80 (m, 2H, H-5'), 2.96–2.80 (m, 1H, $CH(CH_3)_2$), 2.49–2.47 (m, 2H, SCH$_2$), 2.09 (t, J=6.52 Hz, 2H, CHCH$_2$), 1.48 (pq, J=7.29 Hz, 2H, SCH$_2$CH$_2$), 0.94–0.83 (m, 9H, 3×CH$_3$), MS m/z 424 (M+H)$^+$; Anal. (C$_{18}$H$_{29}$N$_7$O$_3$S.0.72 H$_2$O) C, H, N.

5'-Deoxy-2-(N'-3-methyl-1-butylidenehydrazino)-5'-isopropthioadenosine (compound 48). The reaction was carried out with 5'-deoxy-2-hydrazino-5'-isopropylthioadenosine (44, 452 mg, 1.27 mmol). The mixture was purified by column chromatography (eluens 10% MeOH in CH$_2$Cl$_2$).

Yield 350 mg (0.83 mmol, 65%), mp 156–158÷C; $^1$H NMR (DMSO-d$_6$) δ10.03 (bs, 1H, NHM, 7.99 (s, 1H, H-8), 7.33 (t, J=5.86 Hz, 1H, N=CH), 6.93 (bs, 2H, NH$_2$), 5.76 (d, J=6.07 Hz, 1H, H-1'), 5.45 (d, J=6.07 Hz, 1H, OH-2'), 5.22 (d, J=4.80 Hz, 1H, OH-3'), 4.71 (q, J=5.37 Hz, 1H, H-2'), 4.12 (pq, J=3.38 Hz, 1H, H-3'), 3.98–3.92 (m, 1H, H-4'), 2.94 (pt, J=6.38 Hz, 1H, SCH), 2.86 (pq, J=6.83 Hz, 2H, H-5'), 2.08 (t, J=6.62 Hz, 2H, CHCH$_2$), 1.86–1.76 (m, 1H, CH(CH$_3$)$_2$), 1.15 (d, J=6.70 Hz, 6H, SCH(CH$_3$)$_2$)), 0.90 (d, J=6.54 Hz, 6H, 2×CH$_3$); MS m/z 424 (M+H)$^+$; HPLC Alltima C18 5 u column (150 mm×4.6 mm) Reversed phase, flow 1 ml/min. System A: 20–100% MeOH in H$_2$O in 40 min.; retention time: 27.40 min. System B.: 20–100% CH$_3$CN in H$_2$O in 35 min.; retention time: 11.34 min.

An elemental analysis for compounds 1, 3, 4, 33–40, 45 and 47 is provided in Table 1, hereinbelow.

TABLE 1

Elemental Analysis

| No | Mol. Formula | Atom Calculated | Determined |
|---|---|---|---|
| 1 | C$_{10}$H$_{12}$IN$_5$O$_4$.0.33 EtOAc | C 32.18% | C 32.48% |
| | | H 3.49% | H 3.10% |
| | | N 16.60% | N 16.72% |
| 3 | C$_{15}$H$_{23}$N$_7$O$_4$.0.54 CH$_3$OH | C 48.77% | C 49.16% |
| | | H 6.63% | H 6.49% |
| | | N 25.62% | N 25.41% |
| 4 | C$_{16}$H$_{21}$N$_5$O$_4$.0.22 CH$_2$Cl$_2$ | C 53.25% | C 53.31% |
| | | H 5.91% | H 5.82% |
| | | N 19.15% | N 19.05% |
| 33 | C$_{11}$H$_{14}$IN$_5$O$_3$S.0.35 EtOAc | C 32.82% | C 32.93% |
| | | H 3.73% | H 3.56% |
| | | N 15.41% | N 15.51% |
| 34 | C$_{12}$H$_{16}$IN$_5$O$_3$S | C 32.96% | C 33.14% |
| | | H 3.69% | H 3.60% |
| | | N 16.02% | N 16.01% |
| 35 | C$_{13}$H$_{18}$IN$_5$O$_3$S | C 34.60% | C 34.86% |
| | | H 4.02% | H 4.11% |
| | | N 15.52% | N 15.20% |
| 36 | C$_{13}$H$_{18}$IN$_5$O$_3$S.0.11 EtOAc | C 35.00% | C 35.05% |
| | | H 4.12% | H 4.20% |
| | | N 15.20% | N 15.29% |
| 37 | C$_{17}$H$_{23}$N$_5$O$_3$S.0.56 CH$_3$OH | C 53.34% | C 53.28% |
| | | H 6.43% | H 6.10% |
| | | N 17.71% | N 17.64% |
| 38 | C$_{18}$H$_{25}$N$_5$O$_3$S.0.14 CH$_2$Cl$_2$ | C 54.04% | C 54.11% |
| | | H 6.32% | H 5.95% |
| | | N 17.38% | N 17.30% |
| 39 | C$_{19}$H$_{27}$N$_5$O$_3$S.0.12 CH$_2$Cl$_2$ | C 55.20% | C 55.35% |
| | | H 6.60% | H 6.22% |
| | | N 16.83% | N 16.55% |
| 40 | C$_{19}$H$_{27}$N$_5$O$_3$S.0.17 CH$_2$Cl$_2$ | C 54.83% | C 54.86% |
| | | H 6.56% | H 6.22% |
| | | N 16.68% | N 16.68% |
| 45 | C$_{16}$H$_{25}$N$_7$O$_3$S.0.33 CH$_2$Cl$_2$ | C 46.31% | C 46.08% |
| | | H 6.11% | H 6.26% |
| | | N 23.15% | N 23.44% |
| 47 | C$_{18}$H$_{29}$N$_7$O$_3$S.0.72 H$_2$O | C 49.53% | C 49.48% |
| | | H 7.03% | H 6.71% |
| | | N 22.46% | N 22.50% |

Biology—General

Radioligand Binding Studies Measurements with [$^3$H] DPCPX in the absence of GTP were performed according to a protocol published previously.[33] Adenosine A$_{2A}$ receptor affinities were determined according to Gao et al.[34] Adenosine A$_3$ receptor affinities were determined essentially as described.[4,35] Briefly, assays were performed in 50/10/1 buffer (50 mM Tris/10 mM MgCl$_2$/1 mM ethylenediamine-tetra-acetic acid (EDTA) and 0.01% 3-([3-cholamidopropyl]-dimethylammonio)-1-propanesulfonate (CHAPS)) in glass tubes and contained 50 µL of a HEK 293 cell membrane suspension (10–30 µg), 25 µl [$^{125}$I]AB MECA (final concentration 0.15 nM), and 25 µL of ligand. Incubations were carried out for 1 hr at 37° C. and were terminated by rapid filtration over Whatman GF/B filters, using a Brandell cell harvester (Brandell, Gaithersburg, Md.). Tubes were washed three times with 3 ml of buffer. Radioactivity was determined in a Beckman 5500B γ-counter. Nonspecific binding was determined in the presence of 10$^{-5}$ M R-PIA.

cAMP assay A$_{2A}$ CHO cells expressing human adenosine A$_{2A}$ receptors were grown overnight as a monolayer in 24 wells tissue culture plates (400 µL/well; 2×10$^5$ cells/well). cAMP generation was performed in Dulbecco's Modified Eagles Medium (DMEM)/N-2-hydroxyethylpiperazin-N'-2-ethanesulfonic acid (HEPES) buffer (0.60 g HEPES/50 mL DMEM pH 7.4). To each well, washed three times with DMEM/HEPES buffer (250 µλ), 100 µl DMEM/HEPES buffer, 100 µl adenosine deaminase (final concentration 5 IU/ml) and 100 µl of a mixture of rolipram and cilostamide (final concentration 50 µM each) were added. After incubation for 40 minutes at 37° C., 100 µl agonist was added. Here, the full agonist CGS 21680 or compounds 1, 3, 4, 33–40 or 45–48 were used. After 15 minutes at 37° C., the reaction was terminated by removing the medium and adding 200 µl 0.1 M HCl. Wells were stored at –20° C. until assay.

cAMP assay A$_3$ CHO cells expressing the human adenosine A$_3$ receptor were grown overnight as a monolayer in 24 wells tissue culture plates (400 µl/well; 2×10$^5$ cells/well). cAMP generation was performed in Dulbecco's Modified Eagles Medium (DMEM)/N-2-hydroxyethylpiperazin-N'-2-ethansulfonic acid (HEPES) buffer (0.60 g HEPES/50 ml DMEM pH 7.4). To each well, washed three times with DMEM/HEPES buffer (250 µl), 100 µl adenosine deaminase (final concentration 5 IU/ml), 100 µl of a mixture of rolipram and cilostamide (final concentration 50 µM each) and 100 µl agonist (final concentration approx. 100× the K$_i$ value) were added. After incubation for 40 minutes at 37° C., 100 µl forskolin (final concentration 10 µM) was added. After 15 minutes at 37° C., the reaction was terminated by removing the medium and adding 200 µl 0.1 M HCl. Wells were stored at –20° C. until assay. The amounts of cAMP were determined after a protocol with cAMP binding protein[36] with the following minor modifications. As a buffer was used 150 mM K$_2$HPO$_4$/10 mM EDTA/0.2% Bovine Serum Albumine (BSA) at pH 7.5. Samples (20 µl+30 µl 0.1 M HCl) were incubated for at least 2.5 hours at 0° C. before filtration over Whatman GF/B filters. Filters were additionally rinsed with 2×2 ml Tris HCl buffer (pH 7.4, 4° C.). Filters were counted in Packard Emulsifier Safe scintillation fluid (3.5 ml) after 24 hours of extraction.

Data Analysis Apparent K$_i$ and EC$_{50}$ values were computed from the displacement curves by non-linear regression of the competition curves with the software package Prism (Graph Pad, San Diego, Calif.)

Biological Evaluation

All compounds were tested in radioligand binding assays to determine their affinities for the adenosine A$_1$ receptor in rat brain cortex, the A$_{2A}$ receptor in rat striatum and the human $A_3$ receptor as expressed in HEK 293 cells (Table 2). For the adenosine $A_1$ receptor, the tritiated antagonist, [$^3$H]-1,3-dipropyl-8-cyclopentylxanthine ([$^3$H]DPCPX), and for the adenosine $A_{2A}$ receptor, the tritiated antagonist [$^3$H]ZM 241385 were used. [$^{125}$I] AB-MECA, an $A_3$ receptor agonist, was also used. Displacement experiments were performed in the absence of GTP.

All compounds were also tested in functional assays. The ability of the compounds (1, 3, 4, 33–40 and 45–48) to either stimulate cAMP production through human adenosine $A_{2A}$ receptors expressed in CHO cells or inhibit the cAMP production in human adenosine $A_3$ receptors expressed in HEK 293 cells was assessed.

Results and Discussion

In a first attempt to synthesize the compounds of the invention 2-iodoadenosine (1) was used as the starting material[18]. It was noted that the 2-substituent should preferably be introduced prior to the 5'-substituent, since the latter was mostly varied. Substitution of the 2-iodo group of compound 1 with the desired substituents was quite straightforward. The 2-(N'-3-methyl-1-butylidenehydrazino) derivative (3) was synthesized by the condensation of 2-hydrazinoadenosine (2) with isovaleraldehyde.[7] The complete conversion of the iodo-nucleoside to its 2-(1-hexynyl) derivative (4) was carried out by a modification of the traditional palladium-catalyzed cross-coupling reaction.[8] However, subsequent introduction of a good leaving group at the 5'-position of compounds 2–4 failed. Chlorine was preferred as leaving group, since the high reactivities of a p-toluenesulfonyl or methanesulfonyl group can cause ring closure with the adenine part.[23] An improved chlorination method as described by Robins and co-workers[20] to introduce chlorine at the 5'-position, has been successfully used before.[5] In this procedure the formation of a diastereomeric sulfite ester, readily hydrolyzed in aqueous methanolic ammonia, renders the protection of the 2'- and 3'-hydroxyl groups unnecessary. However, when applied to compounds 2, 3 and 4 the desired products 5, 6 and 7 were not obtained. Different amounts of $SOCl_2$ and different temperatures either led to decomposition of the starting material (2) or resulted in the addition of chlorine to the multiple bond of the C2-substituent (3 or 4) besides 5'-chlorination. It was thus concluded that the reaction conditions of this chlorination method were too harsh. The conditions of another chlorination method described to selectively halogenate the 5'-position of different unprotected nucleosides by using carbon tetrahalides and triphenylphosphine,[24] appeared to be too mild. Straightforward mild Mitsunobu reaction conditions were tried as well, first applied to commercially available guanosine and adenosine. However, reaction conditions for selective 5'-chlorination only were difficult to control. Reaction with guanosine (–10° C. for 1 hour) led to chlorination of all three hydroxyl groups, while similar conditions (–10° C. for 15–30 minutes) left adenosine unreacted. In another route mild chlorination methods without interference of the 2'- and 3'-hydroxyl groups were explored by using partly protected starting materials. For this purpose, 2',3'-O-isopropylidene-2-iodoadenosine was successfully prepared by reaction of 2-iodoadenosine (1) with acetone and 70% $HClO_4$ as acid catalyst,[25] and the 2-(1-hexynyl) group was introduced as described above to yield 2-(1-hexynyl)-2',3'-O-isopropylideneadenosine. Chlorination of 2-(1-hexynyl)-2',3'-O-isopropylideneadenosine using $CCl_4$ and $PPh_3$ as described by Homma et al.,[25] yielded the chlorinated compound, but in a low 15% yield only. Unfortunately, problems were encountered in the next reaction. Several attempts to convert 5'-deoxy-2-(1-hexynyl)-5'-chloro-2',3'-O-isopropylideneadenosine into the 5'-(ethylthio)-substituted derivative by reaction with ethanethiol in either KOtBu in MeOH or 2 M $NaOH^1$ did not succeed. With the former procedure only starting material was obtained again, even after 5 hours at 95° C. The latter method caused significant decomposition and neither starting material nor product were obtained.

In yet another route the 5'-substituent was introduced prior to C2-substitution to circumvent all problems met in the previous routes. The method of Robins[20] yielded 5'-deoxy-2-iodo-5'-chloroadenosine from 2-iodoadenosine (1). However, besides the 5'-hydroxyl group, also the 2-iodo group of 1 was replaced by chlorine to some extent, and a mixture of 5'-deoxy-2-iodo-5'-chloroadenosine with 2,5'-dichloro-5'-deoxyadenosine was obtained. Separation of the two products by column chromatography proved impossible. Thus, it was necessary to go further back in the synthesis route, since pure 2,5'-dichloro-5'-deoxyadenosine, obtained by chlorination of 2-chloroadenosine, failed to react with ethanethiol under different conditions (either with KOtBu in MeOH at different temperatures that all regained starting material, or in 2 M NaOH at elevated temperatures yielding the 2,5'-diethylthio substituted derivatives). Finally, in Scheme 1 the successful synthesis of the desired compounds is depicted. The 5'-substituents were introduced at guanosine, which is also the precursor of 2-iodoadenosine (1). Although more laborious, this route starts with the introduction of the 5'-alkylthio substituents at guanosine to circumvent all described problems. Chlorination[20] of guanosine gave 5'-chloro-5'-deoxy-guanosine (16) in 93% yield. Compound 16 was reacted with the appropriate thiol in 2 M $NaOH^{1,5}$ and the 2'- and 3'-hydroxyl groups of compounds 17–20 were subsequently protected to yield the 2',3'-O-acetyl-5'-(alkylthio)-substituted derivatives 21–24. Several laboratories have described chlorination on the 6-position of purine nucleosides with phosphoryl chloride ($POCl_3$).[18,21] To prevent decomposition of the starting materials, the as chemicals used were either properly dried or freshly distilled, and compounds 25–28 were obtained in reasonable to good yields (40%–74%). Subsequently, the 2-amino group of compounds 25–28 was replaced by iodine. The method used[26] was a variation of the originally diazotization-iodine substitution procedure.[22] With this efficient method 29–32 were obtained in good yields (71–82%). Stirring 29–32 in ethanol freshly saturated with $NH_3$ readily removed the protecting groups and slowly aminated the 6-position to give the intermediates 33–36. NMR showed that amination at the 6-position needed stirring at room temperature for at least two days. Subsequent introduction of the C2-substituents was done as described above,[7,8] and compounds 37–40 and 45–48 were obtained in good yields.

Table 2 displays radioligand binding data for all synthesized final products 1, 3, 4, 33–40 and 45–48. In the Table, the substituents are as defined herein (with $R^3$ being a hydrogen), with reference to the compound of general formula (I).

TABLE 2

| | | | Radioligand binding assay $K_i$ (nM) or % displacement at $10^{-5}$ M | | |
|---|---|---|---|---|---|
| No | $R^1W$ | $R^2$ | $A_1{}^a$ | $A_{2A}{}^b$ | $A_3{}^c$ |
| 1 | OH | I | 36.1% | 4200 ± 80 | 297 ± 17 |
| 33 | SCH$_3$ | I | 42.8% | 3900 ± 580 | 257 ± 35 |
| 34 | SC$_2$H$_5$ | I | 386 ± 384 | 1200 ± 120 | 395 ± 61 |
| 35 | S-n-C$_3$H$_7$ | I | 1050 ± 485 | 440 ± 50 | 558 ± 179 |
| 36 | S-i-C$_3$H$_7$ | I | 56.2% | 820 ± 180 | 546 ± 86 |
| 4 | OH | C≡C(CH$_2$)$_3$CH$_3$ | 63.7% | 6 ± 1 | 16.9 ± 4.1 |
| 37 | SCH$_3$ | C≡C(CH$_2$)$_3$CH$_3$ | 35.9% | 60 ± 20 | 14.5 ± 3.4 |
| 38 | SC$_2$H$_5$ | C≡C(CH$_2$)$_3$CH$_3$ | 2180 ± 1980 | 110 ± 30 | 32.3 ± 11.8 |
| 39 | S-n-C$_3$H$_7$ | C≡C(CH$_2$)$_3$CH$_3$ | 46.5% | 170 ± 10 | 88.3 ± 6.6 |
| 40 | S-i-C$_3$H$_7$ | C≡C(CH$_2$)$_3$CH$_3$ | 1270 ± 740 | 220 ± 10 | 75.4 ± 43.1 |
| 3 | OH | NHN=CHCH$_2$CH(CH$_3$)$_2$ | 18.9% | 20 ± 7 | 38.3 ± 3.3 |
| 45 | SCH$_3$ | NHN=CHCH$_2$CH(CH$_3$)$_2$ | 18.9% | 220 ± 20 | 253 ± 36 |
| 46 | SC$_2$H$_5$ | NHN=CHCH$_2$CH(CH$_3$)$_2$ | 21.2% | 500 ± 40 | 814 ± 132 |
| 47 | S-n-C$_3$H$_7$ | NHN=CHCH$_2$CH(CH$_3$)$_2$ | 22.0% | 1500 ± 280 | 697 ± 31 |
| 48 | S-i-C$_3$H$_7$ | NHN=CHCH$_2$CH(CH$_3$)$_2$ | 13.0% | 1800 ± 230 | 409 ± 118 |

From this table it is clear that most compounds had very low or negligible affinity for the adenosine $A_1$ receptor. Also, most compounds did not show any preference in binding at either the adenosine $A_{2A}$ or the $A_3$ receptor, with reasonable to good affinities for both receptor subtypes. Some compounds were slightly selective for the adenosine $A_{2A}$ receptor (3, 4) with an $A_{2A}/A_3$ selectivity ratio significantly smaller than unity, while other compounds favored the adenosine As receptor more (1, 33–34, 38, 48) with an $A_{2A}/A_3$ selectivity ratio up to 15-fold (33). Substitution at the 2-position is known to increase selectivity for the adenosine $A_{2A}$ receptor.[7,8] More recently, radioligand binding studies of 2-(ar)alkynyl-substituted adenosine derivatives have shown that besides $A_1/A_{2A}$ selectivity, also $A_1/A_3$ selectivity is increased by these 2-substituents.[9,10,27] Indeed, the 2-(1-hexynyl) substituent induced high affinity for both the adenosine $A_{2A}$ and $A_3$ receptor compared to the $A_1$ receptor. High affinities for both the adenosine $A_{2A}$ and the $A_3$ receptor were also obtained with the 2-(N'-3-methylbutylidenehydrazino) derivatives, which had previously been tested in functional assays for the adenosine $A_1$ and $A_{2A}$ receptor only.[7] The 2-(1-hexynyl) derivatives (4, 37–40) had the highest affinities for both the adenosine $A_{2A}$ and $A_3$ receptor, compared to the 2-(N'-3-methylbutylidene)hydrazino and 2-iodo substituted compounds. Compound 4 had the highest affinity for the adenosine $A_{2A}$ receptor ($K_i$ value of 6 nM), while compound 37 had the highest affinity for the adenosine $A_3$ receptor ($K_i$ value of 14.5 nM). The adenosine $A_{2A}$ receptor is known to accommodate only C2 substituents with a restrained spacer.[28] This explains the rather low affinities of the 2-iodo derivatives (1, 33–36) for this receptor, and the good affinities of the compounds with larger C2 substituents (1-hexynyl or N'-3-methylbutylidenehydrazino) that contain a relatively rigid spacer. The affinities of the 2-iodo derivatives for the adenosine $A_3$ receptor are significantly better than for the $A_{2A}$ receptor, indicating that the C2 region of the adenosine $A_3$ receptor might be less restrained.

Although the 5'-substituents were primarily shown to induce partial agonism, they also had an effect on the affinity of the compounds. A similar change in affinity was observed for both the adenosine $A_{2A}$ and the $A_3$ receptor. On most occasions, a bulky 5'-substituent led to a decrease, in affinity for both receptor subtypes. Only in the 5'-substituted 2-iodoadenosine series (1, 33–36) adenosine $A_{2A}$ receptor affinity seemed to increase with a bulky substituent. The 5'-hydroxyl derivatives 1, 3 and 4, had the highest affinity for both the adenosine $A_{2A}$ and the $A_3$ receptor, whereas the compounds with the relatively large 5'-propylthio and 5'-isopropylthio substituents had the lowest affinity for the two receptor subtypes. Within the 2-iodoadenosine series increasing size of the 5'-substituent led to a 10-fold increase in $A_3/A_{2A}$ selectivity. On the other hand, within the 2-(1-hexynyl) and 2-(N'-3-methylbutylidenehydrazino) series, the larger 5'-substituents increased adenosine $A_3$ selectivity, with a 9- and 10-fold decrease of $A_3/A_{2A}$ selectivity, respectively. This is in line with previously reported data on $N^6$,5'-disubstituted adenosine derivatives.[5] There too, the introduction of 5'-alkylthio substituents at adenosine derivatives increased the selectivity for the adenosine $A_3$ receptor compared to the $A_{2A}$ receptor. Steric effects appear not to be the explanation for the decrease in adenosine $A_{2A}$ receptor affinity, since the size of, in particular, the 5'-ethylthio group fairly matches that of a 5'-N-ethylcarboxamido substituent, as in NECA and CGS21680. While MECA is known to have a higher affinity for the adenosine $A_3$ receptor than NECA,[29] the results presented herein suggest that the adenosine $A_3$ receptor is better able to accommodate larger 5'-alkylthio groups than the $A_{2A}$ receptor. In literature, modifications other than 5'alkylthio and 5'-N-alkylcarboxamido have been investigated for their affinities for the adenosine $A_{2A}$ or $A_3$ receptor. Mogensen et al. have shown that the relatively large 3-isoxazolyl substituent at the 5'-position of adenosine derivatives indeed decreases adenosine $A_{2A}$ receptor affinity compared to its 5'-N-methylcarboxamido derivative.[30] On the contrary, for poly-substituted adenosine derivatives with a 5-isoxazolyl substituent, it has been claimed that these compounds have a very high adenosine $A_{2A}$ receptor affinity and that they are selective compared to $A_3$.[31]

Table 3 shows the effects of the synthesized compounds in cAMP assays. The substituents are as shown in general formula (I) with $R^3$ representing a hydrogen.

TABLE 3 cAMP assay

| No | R$^1$W | R$^2$ | E$_{max}$ (%) A$_{2A}$$^a$ | EC$_{50}$ (μM) CHO cells A$_{2A}$ | E$_{max}$ (%) A$_3$$^b$ |
|---|---|---|---|---|---|
|  |  | CGS21680 | 100 | — | — |
|  |  | NECA | 102 ± 23 | 0.04 ± 0.004 | — |
|  |  | Cl-IB-MECA | — | — | 83 ± 2 (10) |
| 1 | OH | I | 112 ± 7 | 5.4 ± 0.7 | 68 ± 7 (30) |
| 33 | SCH$_3$ | I | n.a.$^c$ | — | 41 ± 17 (30) |
| 34 | SC$_2$H$_5$ | I | n.a.$^c$ | — | 14 ± 10 (30) |
| 35 | S-n-C$_3$H$_7$ | I | n.a.$^c$ | — | 10 ± 6 (30) |
| 36 | S-i-C$_3$H$_7$ | I | n.a.$^c$ | — | 17 ± 13 (30) |
| 4 | OH | C≡C(CH$_2$)$_3$CH$_3$ | 105 ± 4 | 0.010 ± 0.0003 | 79 ± 8 (3) |
| 37 | SCH$_3$ | C≡C(CH$_2$)$_3$CH$_3$ | 45 ± 6 | 0.7 ± 0.1 | 72 ± 9 (3) |
| 38 | SC$_2$H$_5$ | C≡C(CH$_2$)$_3$CH$_3$ | 79 ± 10 | 0.5 ± 0.02 | 50 ± 21 (3) |
| 39 | S-n-C$_3$H$_7$ | C≡C(CH$_2$)$_3$CH$_3$ | 82 ± 7 | 0.8 ± 0.1 | 33 ± 29 (10) |
| 40 | S-i-C$_3$H$_7$ | C≡C(CH$_2$)$_3$CH$_3$ | 32 ± 4 | 3.6 ± 1.5 | 49 ± 22 (10) |
| 3 | OH | NHN=CHCH$_2$CH(CH$_3$)$_2$ | 92 ± 2 | 1.1 ± 0.2 | 24 ± 17 (3) |
| 45 | SCH$_3$ | NHN=CHCH$_2$CH(CH$_3$)$_2$ | 44 ± 4 | 5.0 ± 0.6 | 41 ± 16 (30) |
| 46 | SC$_2$H$_5$ | NHN=CHCH$_2$CH(CH$_3$)$_2$ | 101 ± 4 | 7.5 ± 0.3 | 7 ± 37 (100) |
| 47 | S-n-C$_3$H$_7$ | NHN=CHCH$_2$CH(CH$_3$)$_2$ | 126 ± 3 | 12.9 ± 0.9 | 16 ± 14 (100) |
| 48 | S-i-C$_3$H$_7$ | NHN=CHCH$_2$CH(CH$_3$)$_2$ | 56 ± 1 | 10.4 ± 1.0 | 26 ± 8 (30) |

$^a$E$_{max}$ compared to the E$_{max}$ of CGS 21680 (±SEM, n = 3; 10 μM) in A$_{2A}$CHO cells;
$^b$Percentage of inhibition of forskolin-induced (10 μM) cAMP production, compared to Cl-IB-MECA. In parentheses the concentration at which the effect was determined (μM, approx. 100 × K$_i$ value);
$^c$not active (no cAMP produced at 30 μM (35) or 100 μM; approx. 100 × K$_i$ value)

All compounds were first tested at concentrations of 1–100 μM (25 to 166 times the K$_i$ value), for determination of the amount of cAMP produced via the adenosine A$_{2A}$ receptor. For compounds 1, 4, 37–40, 3 and 45–48 full dose-response curves were recorded next. The E$_{max}$ values were determined from the fitted curves and compared to the maximal amount of cAMP (E$_{max}$) produced by the reference agonist, CGS21680 (10 μM).

Surprisingly, the 5'-substituted 2-iodo derivatives 33–36 did not produce any cAMP. This suggested either that they behaved as antagonists in this assay, or that they were substrates for adenosine deaminase (ADA) present in the assay. The latter explanation is however unlikely, since these compounds did not seem to be substrates for ADA in the cAMP assay for the adenosine A$_3$ receptor, in which ADA was present as well. All adenosine derivatives (1, 3 and 4) produced similar amounts of cAMP as the fall agonist CGS 21680, suggesting that they behaved as full agonists. The 5'-substituted derivatives within the 2-(1-hexyn-1-yl) series were partial agonists compared to 4 and CGS 21680. The 5'-substituted 2-(N'-3-methylbutylidenehydrazino) derivatives showed a similar trend in cAMP production, although with higher efficacies. The efficacies of compounds 46 and 47 were similar to that of the full agonist CGS21680 and thus 46 and 47 behaved as full agonists for this receptor. Overall, most of the C2,5'-disubstituted adenosine derivatives behaved as partial agonists for the adenosine A$_{2A}$ receptor in this assay. The compounds with either a 5'-ethylthio or a 5'-i-propylthio substituent (37, 40, 45 and 48) had the lowest efficacies. The EC$_{50}$ values for the adenosine A$_{2A}$ receptor were up to 54-fold higher than the K$_i$ values. The rank orders of potency and affinity were identical, however. It must be noted that the EC$_{50}$ values were determined for the human adenosine A$_{2A}$ receptor expressed in CHO cells, whereas the K$_i$ values were determined on rat striatum.[32]

The ability of the compounds to inhibit forskolin-stimulated (10 μM) cAMP production via the adenosine A$_3$ receptor was also studied. All compounds were tested at a single (final) concentration of 3–100 μM (73 to 200 times the K$_i$ value). The 2-iodo substituted derivatives (1, 33–36) inhibited the forskolin-induced cAMP production via the adenosine A$_3$ receptor, proof of the agonistic character of the compounds that were silent on the adenosine A$_{2A}$ receptor. Compounds 1 and 4, with an intact 5'-hydroxyl group, showed almost full inhibition of the cAMP production comparable with the reference full agonist Cl-IB-MECA. Compound 3 only gave 24% inhibition of the cAMP production, indicating that it behaved as a partial agonist for the adenosine A$_3$ receptor. The 5'-substituted derivatives all showed submaximal levels of inhibition of the forskolin-induced cAMP production, with the same trend within the three 2-substituted series (Table 3). This indicates that the di-substituted adenosine derivatives were all partial agonists for the adenosine A$_3$ receptor in this assay. The compounds with the 5'-methylthio substituent (33, 37, 45) had the highest intrinsic efficacies, whereas the compounds with a relatively large 5'-substituent (n-propylthio, 35 and 39) had the lowest intrinsic activities for the adenosine A$_3$ receptor.

Example 2

Synthesis of N$^6$,C2,5'-substituted Adenosine Derivatives

Chemistry—General

Chemicals and solvents Guanosine was obtained from Aldrich (Aldrich Chemie, Sigma-Aldrich Chemie BV, Zwijndrecht, The Netherlands). All other reagents were from standard commercial sources and of analytic grade. [$^3$H] DPCPX (1,3-dipropyl-8-cyclopentylxanthine), [$^3$H]ZM 241385 and [$^{125}$I]AB-MECA were purchased from NEN (Hoofddorp, The Netherlands).

Chromatography Thin-layer chromatography (TLC) was carried out using aluminium sheets (20×20 cm) with silica gel F$_{254}$ from Merck. Spots were visualised under UV (254 nm). Preparative column chromatography was performed on silica gel (230–400 mesh ASTM).

Instrument and Analyses Elemental analyses were performed for C, H, N (Department of Analytical Chemistry, Leiden University, The Netherlands). $^{13}$C NMR spectra were measured at 50.1 MHz with a JEOL JNM-FX 200 spectrometer equipped with a PG 200 computer operating in the Fourier-transform mode. 1H NMR spectra were measured at 200 MHz, using the above mentioned spectrometer, or at 300 MHz, using a Bruker WM-300 spectrometer equipped with an ASPECT-2000 computer operating in the Fourier-transform mode. Chemical shifts for $^1$H and $^{13}$C NMR are given in ppm ($\lambda$) relative to tetramethylsilane (TMS) as internal standard.

All high resolution mass spectra were measured on a Finnigan MAT900 mass spectrometer equipped with a direct insertion probe for EI experiments (70 eV with resolution 1000) or on a Finnigan MAT TSQ-70 spectrometer equipped with an electrospray interface for ESI experiments. Spectra were collected by constant infusion of the analyte dissolved in 80/20 methanol/H$_2$O. ESI is a soft ionization technique resulting in protonated, sodiated species in positive ionization mode and deprotonated species in the negative ionization mode.

Melting points were determined in a Büchi capillary melting point apparatus.

Synthesis Procedures

Syntheses methyl 2,3-O-isopropylidene-β-D-ribofuranoside (compound 50). A suspension of 88 g (0.59 mol) of dry D-ribose in acetone (400 ml), dimethoxypropane (176 ml) and MeOH (380 ml) was stirred, cooled in an ice-bath. Over a period of 4 hr, each 30 minutes HCl gas was led through the solution, and then the mixture was stirred overnight at room temperature. The mixture was neutralized with pyridine and concentrated in vacuum. The residue was extracted with H$_2$O and ether. The organic layers were combined, dried (MgSO$_4$) and concentrated. Yield 115 g (0.56 mol, 95%); R$_f$ 0.38 (PE40/60:EtOAc 1:1). $^1$H NMR (CDCl$_3$) δ 4.97 (s, 1H, H-1), 4.82–4.57 (2×d, 2H, J=6.18 Hz, H-2,3), 4.42–4.39 (m, 1H, H-4), 3.71–3.62 (m, 2H, H-5), 3.41 (s, 3H, OCH$_3$), 1.48, 1.31 (2×s, 6H, 2×CCH$_3$) ppm $^{13}$C NMR (CDCl$_3$) δ 112.02 (C(CH$_3$)$_2$), 109.8 (C-1), 88.13, 85.64, 81.38 (C-2,3,4), 63.80 (C-5), 55.24 (OCH$_3$), 26.24, 24.61 (2×CH$_3$) ppm General procedure for the alkylation of compound 50 into the methyl 5-O-alkyl-2,3-O-isopropylidene-β-D-ribofuranoside derivatives 51–53. Methyl 2,3-O-isopropylidene-β-D-ribofuranoside (50, 53.0 g, 0.26 mol) was dissolved in dry dimethylformamide (DMF, 300 ml). This was cooled (0° C.) and NaH (60% in mineral oil, 11.5 g, 0.29 mol) was slowly added. The mixture was allowed to warm to room temperature, cooled again, and the appropriate alkylhalide (0.31 mol) was added very slowly. The mixture was stirred at room temperature overnight. The mixture was treated with MeOH (100 ml) and concentrated in vacuo. It was coevaporated with toluene (2×). The (black) mixture was extracted with water and EtOAc (250 ml each). The water-layer was subsequently extracted with CH$_2$Cl$_2$. The organic layers were combined, dried (MgSO$_4$) and concentrated. The residue was purified by column chromatography.

Methyl 5-O-methyl-2,3-O-isopropylidene-β-D-ribofuranoside (compound 51). The reaction was carried out with 50 (53.0 g, 0.26 mol) and methane-iodine (CH$_3$I, 0.31 mol, 19.4 ml). The mixture was purified by column chromatography (eluens gradient PE40/60, PE40/60:EtOAc 2:1). Yield 55.1 g (0.25 mol, 97%) R$_f$ 0.56 (PE40/60:EtOAc 1:1). $^{13}$C NMR (CDCl$_3$) δ 111.71 (C(CH$_3$)$_2$), 108.79 (C-1), 84.76, 84.47, 81.70 (C-2,3,4), 73.18 (C-5), 58.38 (OCH$_3$), 54.03 (CH$_2$OCH$_3$), 25.98, 24.49 (2×C(CH$_3$)$_2$) ppm.

Methyl 5-O-ethyl-2,3-O-isopropylidene-β-D-ribofuranoside (compound 52). The reaction was carried out with 50 (33.4 g, 0.16 mol) and iodoethane (0.20 mol, 15.9ml). The mixture was purified by column chromatography (eluens gradient PE40/60, PE40/60:EtOAc 1:1). Yield 35.2 g (0.15 mol, 92%); R$_f$ 0.62 (PE40/60:EtOAc 1:1). $^{13}$C NMR (CDCl$_3$) δ 111.41 (C(CH$_3$)$_2$), 108.55 (C-1), 84.50, 81.55 (C-2,3,4), 70.78 (CH$_2$CH$_3$), 65.91 (C-5), 53.85 (OCH$_3$), 25.77, 24.31 (C(CH$_3$)$_2$), 14.48 (CH$_2$CH$_3$) ppm.

Methyl 5O-cyclopropyl-2,3-O-isopropylidene-β-D-ribofuranoside (compound 53). The reaction was carried out with 50 (43.6 g, 0.21 mol) and cyclopropylbromide (0.26 mol, 20.6 ml). Prior to treatment with MeOH, the mixture was stirred at room temperature. The mixture was purified by column chromatography (eluens gradient PE40/60, PE40/60:EtOAc 1:1). Yield 19.5 g (79.8 mmol, 38%); R$_f$ 0.70 (PE40/60:EtOAc 1:1). $^{13}$C NMR (CDCl$_3$) δ 111.94 (C(CH$_3$)$_2$), 108.90 (C-1), 84.88, 84.65, 81.85 (C-2,3,4), 71.19 (C-5), 54.38 (OCH), 53.21 (OCH$_3$), 26.15,24.72 (C(CH$_3$)$_2$), 5.37 (CH$_2$CH$_2$) ppm.

General procedure for the deprotection of compounds 51–53 into the 5-O-alkyl-β-D-ribofuranose derivatives 54–56. The appropriate methyl 5-O-alkyl-2,3-O-isopropylidene-β-D-ribofuranose (4.48 mmol) was dissolved in 15 mL HCl (0.04 M) and was refluxed for 2 h. The solution was neutralized with BaCO$_3$, filtered and concentrated. The mixture was purified by column chromatography.

5-O-Methyl-α,β-D-ribofuranose (compound 54). The reaction was carried out with methyl 5-O-methyl-2,3-O-isopropylidene-β-D-ribofuranoside (51, 1 g, 4.58 mmol). The mixture was purified by column chromatography (eluens 10% MeOH in EtOAc). Yield 0.44 g (2.68 mmol, 59%/); R$_f$ 0.34 (10% MeOH in EtOAc).

$^{13}$C NMR (MeOD) δ 103.12 (C-1, β), 97.78 (C-1, α), 83.94, 82.36, 77.37, 76.88, 72.61, 72.12 (C-2,3,4, α+β), 73.93 (C-5), 59.51, 59.39 (OCH$_3$, α+β) ppm.

5-O-Ethyl-α,β-D-ribofuranose (compound 55). The reaction was carried out with methyl 5-O-ethyl-2,3-O-isopropylidene-β-D-ribofuranoside (52, 1.0 g, 4.85 mmol). The mixture was purified by column chromatography (10% MeOH in EtOAc). Yield 0.56 g (3.14 mmol, 65%); R$_f$ 0.40 (10% MeOH in EtOAc). $^{13}$C NMR (MeOD) δ 102.88 (C-1, β), 97.51 (C-1, α), 84.09, 82.42, 76.60, 72.53, 72.03 (C-2,3,4, α+β), 73.40 (C-5), 67.83 (CH$_2$CH$_3$), 15.34 (CH$_3$) ppm.

5-O-Cyclopropyl-α,β-D-ribofuranose (compound 56). The reaction was carried out with methyl 5-O-cyclopropyl-2,3-O-isopropylidene-β-D-ribofuranoside (53, 4.4 g, 18 mmol). The mixture was purified by column chromatography (10% MeOH in EtOAc). Yield 2.09 g (11 mmol, 61%); R$_f$ 0.43 (10% MeOH in EtOAc). $^{13}$C NMR (MeOD) δ101.60 (C-1, β), 96.41 (C-1, α), 80.77, 79.42, 74.40, 73.53, 72.03 (C-2,3,4, α+β), 69.40 (C-5), 56.97 (CH) 7.83 (CH$_2$CH$_2$) ppm.

General procedure for the acylation of compounds 54–56 into the 1,2,3-tri-O-acetyl-5-O-alkyl-α,β-D-ribofuranose derivatives 57–59 The appropriate 5-O-alkyl-α,β-D-ribofuranose (2.68 mmol) was dissolved in 25 ml pyridine. A catalytic amount of dimethylaminopyridine (MAP) and acetic anhydride (8.84 mmol, 843 μl) were added. The mixture was stirred for 2 h at room temperature, was concentrated in7 vacuo and coevaporated with toluene. The oil was extracted with water and EtOAc (25 ml each). The organic layer was dried (MgSO$_4$) and concentrated and purified by column chromatography.

1,2,3-Tri-O-Acetyl-5-O-methyl-α,β-D-ribofuranose (compound 57). The reaction was carried out with 5-O-methyl-α,β-D-ribofuranose (54, 0.44 g, 2.68 mmol). The mixture was purified by column chromatography (eluens 10% MeOH in EtOAc). Yield 0.70 g (2.41 mmol, 90%); $R_f$ 0.76 (10% MeOH in EtOAc). $^{13}$C NMR (CDCl$_3$) δ 168.98, 168.68, 168.39 (3×C=O, α+β), 97.64 (C-1, β), 93.64 (C-1, α), 82.81, 80.30, 73.99, 73.67, 70.20, 69.67 (C-2,3,4, α+β), 71.75 (C-5), 58.67 (OCH$_3$), 20.26, 19.70 (3×COCH$_3$) ppm.

1,2,3-Tri-O-Acetyl-5-O-ethyl-α,β-D-ribofuranose (compound 58). The reaction was carried out with 5-O-ethyl-α,β-D-ribofuranose (7, 0.56 g, 3.14 mmol). The mixture was purified by column chromatography (eluens 10% MeOH in is EtOAc). Yield 0.85 g (2.79 mmol, 89%); $R_f$ 0.75 (10% MeOH in EtOAc); $^{13}$C NMR (CDCl$_3$) δ 168.68, 168.42, 168.02 (3×C=O), 97.43 (C-1, β), 93.40 (C-1, α), 82.69, 80.24, 73.50, 70.08, 69.53 (C-2,3,4, α+β), 69.38, 68.94 (C-5, α+β), 66.05 (CH$_2$CH$_3$), 19.96, 19.41 (3×COCH$_3$), 14.18 (CH$_2$CH$_3$) ppm.

1,2,3-Tri-O-Acetyl-5-O-cyclopropyl-α,β-D-ribofuranose (compound 59). The reaction was carried out with 5-O-cyclopropyl-α,β-D-ribofuranose (56, 3.42 g, 18.0 mmol). The mixture was purified by column chromatography (eluens 10% MeOH in EtOAc). Yield 4.74 g (15.0 mmol, 83%); $R_f$ 0.72 (10% MeOH in EtOAc); $^{13}$C NMR (CDCl$_3$) δ 169.27, 168.98, 168.74 (3×C=O), 97.81 (C-1, β), 93.78 (C-1, α), 82.84, 80.36, 73.91, 70.43, 69.88 (C-2,3,4, α+β), 69.79, 69.38 (C-5, α+β), 53.50 (CH), 20.55, 20.02 (3×COCH$_3$), 5.22 (CH$_2$CH$_2$) ppm.

General procedure for the coupling of compounds 57–59 to 6-chloropurine or 2,6-dichloropurine to give compounds 60–65

Silylation of the base The appropriate base (193.8 mg, 1.27 mmol) was treated with 1,1,1,3,3,3-hexamethyldisilazane (HMDS, 5 ml, 23.7 mmol) and 12.5 μl chlorotrimethylsilane (TMSCl, 0.1 mmol) at 130÷C for 20 hr. The silylated compound was concentrated and used without further purification.

Vorbrüggen coupling To the appropriate silylated base (12.9 mmol) was added the appropriate ribose (10.3 mmol) in 15 ml dry 1,2-dichloroethane. The residue was co-evaporated twice with dry 1,2-dichloroethane and subsequently dissolved in 75 ml dry 1,2-dichloroethane. The solution was gently refluxed and after 5 minutes trimethylsilyl-trifluoromethane sulfonate (TMS triflate) (997 μl, 5.16 mmol) was added. The mixture was refluxed for 2 hr, cooled to room temperature and diluted with CH$_2$Cl$_2$. It was extracted with 5% NaHCO$_3$ and water. The organic layer was dried (MgSO$_4$), concentrated -and purified by column chromatography.

6-Chloro-9-(2,3-di-O-acetyl-5-O-methyl-β-D-ribofuranose)-purine (compound 60). The reaction was carried out with silylated 6-chloropurine (12.9 mmol) and 1,2,3-tri-O-acetyl-5-O-methyl-α,β-D-ribofuranose (57, 3.0 g, 10.3 mmol). The mixture was purified by column chromatography (eluens 3% acetone in CH$_2$Cl$_2$). Yield 1.9 g (4.94 mmol, 48%); $R_f$ 0.11 (3% acetone in CH$_2$Cl$_2$). $^1$H NMR (CDCl$_3$) δ 8.75 (s 1H, H-8), 8.56 (s, 1H, H-2), 6.41 (d, 1H, J=6.18 Hz, H-1'), 5.80 (t, 1H, J=5.49 Hz, H-2'), 5.60–5.56 (m, 1H, H-3'), 4.39 (q, 1H, J=2.41 Hz, H-4'), 3.69 (dq, 2H, J=7.21 Hz, J=2.40 Hz, H-5'), 3.48 (s, 3H, OCH$_3$), 2.16, 2.03 (2×s, 6H, 2×COCH$_3$) ppm.

2,6-Dichloro-9-(2,3-di-O-acetyl-5-O-methyl-β-D-ribofuranosyl)-purine (compound 61). The reaction was carried out with silylated 2,6-dichloropurine (10.3 mmol) and 1,2,3-tri-O-acetyl-5-O-methyl-α,β-D-ribofuranose (57, 2.39 g, 8.24 mmol). The mixture was purified by column chromatography (eluens gradient 4%–6% acetone in CH$_2$Cl$_2$). Yield 2.91 g (6.94 mmol, 84%); $^1$H NMR (CDCl$_3$) δ 8.41 (s, 1H, H-8), 6.18 (d, 1H, J=6.52 Hz, H-1'), 5.60 (dd, 1H, J=6.18 Hz, J=5.49 Hz, H-2'), 5.39 (dd, 1H, J=5.15 Hz, J=2.06 Hz, H-3'), 4.25–4.23 (m, 1H, H-4'), 3.58–3.48 (m, 2H, H-5'), 3.33 (s, 3H, OCH$_3$), 2.00, 1.88 (2×s, 6H, 2×COCH$_3$) ppm.

6-Chloro-9-(2,3-di-O-acetyl-5-O-ethyl-β-D-ribofuranosyl)-purine (compound 62). The reaction was carried out with silylated 6-chloropurine (11.6 mmol) and 1,2,3-tri-O-acetyl-5-O-ethyl-α,β-D-ribofuranose (58, 2.82 g, 9.28 mmol). The mixture was purified by column chromatography (eluens gradient 4–6% acetone in CH$_2$Cl$_2$). Yield 3.03 g (7.60 mmol, 82%); $R_f$ 0.17 (3% acetone in CH$_2$Cl$_2$); $^1$H NMR (CDCl$_3$) δ 8.51 (s, 1H, H-8), 8.45 (s, 1H, H-2), 6.20 (d, 1H, J=6.18 Hz, H-1'), 5.64 (t, 1H, J=5.15 Hz, H-2'), 5.40–5.36 (m, 1H, H-3'), 4.24–4.18 (m 1H, H-4'), 3.53 (dq, 2H, J=13.73 Hz, J=2.06 Hz, H-5'), 3.42 (q, 2H, J=6.86 Hz, CH$_2$CH$_3$), 1.94, 1.81 (2×s, 6H, 2×COCH$_3$), 1.07 (t, 3H, J=6.86 Hz, CH$_2$CH$_3$); $^{13}$C NMR (CDCl$_3$) δ 169.33, 168.89 (2×C=O), 151.70, 151.32, 150.56, 143.26, 131.41 (C-2,4,5,6,8), 85.46, 82.78, 74.08, 74.86 (C-1',2',3',4'), 69.35, 66.90 (OCH2, C-5'), 20.28, 19.19 (2×COCH$_3$), 14.71 (CH$_3$) ppm.

2,6-Dichloro-9-(2,3-di-O-acetyl-5-O-ethyl-β-D-ribofuranosyl)-purine (compound 63). The reaction was carried out with silylated 2,6-dichloropurine (10.3 mmol) and 1,2,3-tri-O-acetyl-5-O-ethyl-α,β-D-ribofuranose (58, 2.51 g, 8.24 mmol). The mixture was purified by column chromatography (eluens gradient 4%–6% acetone in CH$_2$Cl$_2$). Yield 2.93 g (6.76 mmol, 82%); $^1$H NMR (CDCl$_3$) δ 8.66 (s, 1H, H-8), 6.39 (d, 1H, J=6.53 Hz, H-1'), 5.81 (dd, 1H, J=6.86 Hz, J=5.49 Hz, H-2'), 5.58 (dd, 1H, J=7.21 Hz, J=2.06 Hz, H-3'), 4.43–4.41 (m, 1H, H-4'), 3.75 (dq, 2H, J=10.64 Hz, J=2.41 Hz, H-5'), 3.64 (t, 2H, J=6.87 Hz, CH$_2$CH$_3$), 2.19, 2.06 (2×s, 6H, 2×COCH$_3$), 1.32 (t, 3H, J=6.86 Hz, CH$_2$CH$_3$) ppm.

6-Chloro-9-(2,3-di-O-acetyl-5-O-cyclopropyl-β-D-ribofuranosyl)-purine (compound 64). The reaction was carried out with silylated 6-chloropurine (9.79 mmol) and 1,2,3-tri-O-acetyl-5-O-cyclopropyl-α,β-D-ribofuranose (59, 2.48 g, 7.83 mmol). The mixture was purified by column chromatography (eluens gradient 4%–6% acetone in CH$_2$Cl$_2$). Yield 2.09 g (5.10 mmol, 65%); $^1$H NMR (CDCl$_3$) δ 8.76 (s, 1H, H-8), 8.59 (s, 1H, H-2), 6.42 (d, 1H, J=6.18 Hz, H-1'), 5.83–5.77 (m, 1H, H-2'), 5.57–5.53 (m, 1H, H-3'), 4.45–4.42 (m, 1H, H-4'), 3.87–3.77 (m, 2H, H-5'), 3.45–3.42 (m, 1H, CH), 2.19, 2.06 (2×s, 6H, 2×COCH$_3$), 0.67–0.55 (m, 4H, CH$_2$CH$_2$) ppm.

2,6-Dichloro-9-(2,3-di-O-acetyl-5-O-cyclopropyl-β-D-ribofuranosyl)-purine (compound 65). The reaction was carried out with silylated 2,6-dichloropurine (8.95 mmol) and 1,2,3-tri-O-acetyl-5-O-cyclopropyl-α,β-D-ribofuranose (59, 2.26 g, 7.16 mmol). The mixture was purified by column chromatography (eluens gradient 4%–6% acetone in CH$_2$Cl$_2$). Yield 2.55 g (5.73 mmol, 80%); 1H NMR (CDCl$_3$) δ 8.32 (s, 1H, H-8), 6.10 (d, 1H, J=6.18 Hz, H-1'), 5.52–5.46 (m, 1H, H-2'), 5.28–5.25 (m, 1H, H-3'), 4.20-4.17 (m, 1H, H-4'), 3.60 (q, 2H, J=7.56 Hz, H-5'), 3.24–3.19 (m, 1H, OCH), 1.91, 1.82 (2×s, 6H, 2×COCH$_3$), 0.43–0.32 (m, 4H, CH$_2$CH$_2$) ppm.

General procedure for the amination of compounds 60–65 into the substituted adenosine derivatives 66–83

Method A (synthesis of compounds 66, 69, 72, 75, 78 and 81) The appropriate 6-chloro-9-(2,3-di-O-acetyl-5-O-alkyl-β-D-ribofuranosyl)-purine or the appropriate 2,6-dichloro-9-(2,3-di-O-acetyl-5-O-alkyl-β-D-ribofuranosyl)-purine (1.53 mmol) was dissolved in EtOH/NH$_3$ (30 ml) and the mixture was stirred overnight at room temperature. The mixture was concentrated and purified by column chromatography.

Method B (synthesis of compounds 67, 68, 70, 71, 73, 74, 76, 77, 79, 80, 82 and 84) The appropriate 6-chloro-9-(2,3-di-O-acetyl-5-O-alkyl-β-D-ribofuranosyl)-purine or the appropriate 2,6-dichloro-9-(2,3-di-O-acetyl-5-O-alkyl-β-D-ribofuranosyl)-purine (1.53 mmol) was dissolved in EtOH absolute (10 ml). The appropriate amine (2.3 mmol) and Et$_3$N (1.91 mmol) were added and the mixture was refluxed overnight. The mixture was concentrated and dissolved in EtOH/NH$_3$ (30 ml) and stirred overnight at room temperature. The mixture was concentrated again and purified by column chromatography.

5'-O-methyladenosine (compound 66). Method A. The reaction was carried out with 6-chloro-9-(2,3-di-O-acetyl-5-O-methyl-β-D-ribofuranosyl)-purine (60, 682 mg, 1.77 mmol). The mixture was purified by column chromatography (eluens 5% MeOH in CH$_2$Cl$_2$). Yield 393 mg (1.40 mmol, 79%), mp 112–114° C.; R$_f$ 0.43 (10% MeOH in CH$_2$Cl$_2$); $^1$H NMR (DMSO-d$_6$) δ 8.28 (s, 1H, H-8), 8.14 (s, 1H, H-2), 7.26 (bs, 2H, NH$_2$), 5.87 (d, 1H, J=5.49 Hz, OH-2'), 5.25 (d, 1H, J=5.15 Hz, OH-3'), 4.57 (q, 1H, J=6.18 Hz, H-2'), 4.13 (q, 1H, J=4.47 Hz, H-3'), 3.99–3.98 (m, 1H, H-4'), 3.57–3.48 (m, 2H, H-5'), 3.28 (s, 3H, OCH$_3$) ppm; MS m/z 282 (M+H)$^{30}$ ; Anal. (C$_{11}$H$_{15}$N$_5$O$_4$. 0.5H$_2$O) C, H, N.

N$^6$-cyclopentyl-5'-O-methyladenosine (compound 67). Method B. The reaction was carried out with 6-chloro-9-(2,3-di-O-acetyl-5-O-methyl-β-D-ribofuranosyl)-purine (60, 589 mg, 1.53 mmol) and cyclopentylamine (2.3 mmol, 227 μl). The mixture was purified by column chromatography (eluens 5% MeOH in CH$_2$Cl$_2$). Yield 476 mg (1.36 mmol, 89%), mp 164–166° C.; R$_f$ 0.51 (eluens 10% MeOH in CH$_2$Cl$_2$). The product was re-crystallized from CH$_3$CN; $^1$H NMR (DMSO-d$_6$) δ 8.28 (s, 1H, H-8), 8.18 (s, 1H, H-2), 7.70 (d, 1H, J=7.55 Hz, NH), 5.89 (d, 1H, J=4.80 Hz, H-1'), 5.50 (d, 1H, J=5.15 Hz, OH-2'), 5.26 (d, 1H, J=5.15 Hz, OH-3'), 4.56 (q, 1H, J=4.12 Hz, H-2'), 4.13 (q, 1H, J=4.46 Hz, H-3'), 3.99 (q, 1H, J=4.12 Hz, H-4'), 3.57–3.42 (m, 2H, H-5'), 3.28 (s, 3H, OCH$_3$), 2.01–1.83 (m, 2H, cyclopentyl), 1.73–1.52 (m, 4H, cyclopentyl); MS m/z 350 (M+H)$^+$; Anal. (C$_{16}$H$_{23}$N$_5$O$_4$.0.7 CH$_3$CN) C, H, N.

N$^6$-(3-iodobenzyl)-5'-O-methyladenosine (compound 68). Method B. The reaction was carried out with 6-chloro-9-(2,3-di-O-acetyl-5-O-methyl-β-D-ribofuranosyl)-purine (60, 363 mg, 0.94 mmol) and 3-iodobenzylamine.HCl (1.41 mmol, 380 mg). The mixture was purified by column chromatography (eluens 5% MeOH in CH$_2$Cl$_2$). Yield 397 mg (0.80 mmol, 85%), mp 155–157° C.; R$_f$ 0.54 (eluens 10% MeOH in CH$_2$Cl$_2$); $^1$H NMR (DMSO-d$_6$) δ 8.40 (bs, 1H, NH), 8.33 (s, 1H, H-8), 8.21 (s, 1H, H-2), 7.70 (s, 1H, CCHCI), 7.57 (d, 1H, J=6.52 Hz, CCHCHCH), 7.34 (d, 1H, J=5.15 Hz, CCHCH), 7.08 (t, 1H, J=8.93 Hz, CCHCH), 5.89 (d, 1H, J=4.12 Hz, H-1'), 5.50–5.47 (m, 1H, OH-2'), 5.27–5.25 (m, 1H, OH-3'), 4.68–4.56 (m, 3H, H-2', NHCH$_2$), 4.14–4.13 (m, 1H, H-3'), 4.01–3.98 (m, 1H, H-4'), 3.57–3.53 (m, 2H, H-5'), 3.31 (s, 3H, OCH$_3$); MS m/z 498 (M+H)$^+$; Anal. (C$_{18}$H$_{20}$N$_5$O$_4$) C, H, N.

2-Chloro-5'-O-methyladenosine (compound 69). Method A. The reaction was carried out with 2,6-dichloro-9-(2,3-di-O-acetyl-5-O-methyl-β-D-ribofuranosyl)-purine (61, 667 mg, 1.59 mmol). The mixture was purified by column chromatography (eluens 5% MeOH in CH$_2$Cl$_2$). Yield 382 mg (1.21 mmol, 760%), mp 200–202° C.; R$_f$ 0.49 (10% MeOH in CH$_2$Cl$_2$); $^1$H NMR (DMSO-d$_6$) δ 8.30 (s, 1H, H-8), 7.83 (bs, 2H, NH$_2$), 5.80 (d, 1H, J=5.15 Hz, H-1'), 5.53 (d, 1H, J=6.12 Hz, OH-2'), 5.29 (d, 1H, J=5.49 Hz, OH-3'), 4.52 (q, 1H, J=5.84 Hz, H-2'), 4.11–3.99 (m, 2H, H-3',4'), 3.55–3.46 (m, 2H, H-5'), 3.28 (s, 3H, OCH$_3$); MS m/z 316 (M+H)$^+$; Anal. (C$_{11}$H$_{14}$ClN$_5$O$_4$.1.0 CH$_2$Cl$_2$) C, H, N.

N$^6$-Cyclopentyl-2-chloro-5'-O-methyladenosine (compound 70). Method B. The reaction was carried out with 2,6-dichloro-9-(2,3-di-O-acetyl-5-O-methyl-β-D-ribofuranosyl)-purine (61, 505 mg, 1.2 mmol) and cyclopentylamine (1.8 mmol, 178 μL). The mixture was purified by column chromatography (eluens 2% MeOH in CH$_2$Cl$_2$). Yield 364 mg (0.95 mmol, 79%), mp 124–126° C.; R$_f$ 0.15 (eluens 2% MeOH in CH$_2$Cl$_2$); $^1$H NMR (DMSO-d$_6$) δ 8.33 (bs, 1H, NH), 8.30 (s, 1H, H-8), 5.81 (d, 1H, J=4.46 Hz, H-1'), 5.51 (d, 1H, J=3.36 Hz, OH-2'), 5.29 (d, 1H, J=3.32 Hz, OH-3'), 4.59–4.29 (m, 2H, CH, H-2'), 4.41–3.99 (m, 2H, H-3',4'), 3.56–3.52 (m, 2H, H-5'), 1.94–1.92 (m, 2H, cyclopentyl), 1.71–1.50 (m, 4H, cyclopentyl); MS m/z 384 (M+H)$^+$; Anal. (C$_{16}$H$_{22}$ClN$_5$O$_4$.0.1 CH$_2$Cl$_2$) C, H, N.

N$^6$-(3-iodobenzyl)-2-Chloro-5'-O-methyladenosine (compound 71). Method B. The reaction was carried out with 2,6-dichloro-9-(2,3-di-O-acetyl-5-O-methyl-β-D-ribofuranosyl)-purine (61, 372 mg, 0.89 mmol) and 3-iodobenzylamine.HCl (1.34 mmol, 360 mg). The mixture was purified by column chromatography (eluens 2% MeOH in CH$_2$Cl$_2$). Yield 383 mg (0.72 mmol, 81%), mp 84–86° C.; R$_f$ 0.59 (10% MeOH in CH$_2$Cl$_2$). The product was recrystallised from CH$_3$COCH$_3$; $^1$H NMR (DMSO-d$_6$) δ 8.89 (bs, 1H, NH), 8.35 (s, 1H, H-8), 7.73 (s, 1H, CCHCl), 7.60 (d, 1H, J=5.83 Hz, CCHCHCH), 7.33 (d, 1H, J=6.12 Hz, CCHCH), 7.12 (t, 1H, J=7.55 Hz, CCHCH), 5.82 (d, 1H, J=5.15 Hz, H-1'), 5.54 (d, 1H, J=5.84 Hz, OH-2'), 5.30 (d, 1H, J=5.49 Hz, OH-3'), 4.61–4.51 (m, 3H, NHCH$_2$, H-2'), 4.09–4.00 (m, 2H, H-3',4'), 3.56–3.52 (m, 2H, H-5'), 3.28 (s, 3H, OCH$_3$); MS m/z 532 (M+H)$^-$; Anal. (C$_{18}$H$_{19}$ClIN$_5$O$_4$.0.3 CH$_3$COCH$_3$) C, H, N.

5'-O-Ethyladenosine (compound 72). Method A. The reaction was carried out with 6-chloro-9-(2,3-di-O-acetyl-5-O-ethyl-β-D-ribofuranosyl)-purine (62, 663 mg, 1.70 mmol). The mixture was purified by column chromatography (eluens 5% MeOH in CH$_2$Cl$_2$). Yield 407 mg (1.38 mmol, 81%), mp 110–112° C.; R$_f$ 0.48 (10% MeOH in CH$_2$Cl$_2$); $^1$H NMR (DMSO-d$_6$) δ 8.32 (s, 1H, H-8), 8.14 (s, 1H, H-2), 7.27 (bs, 2H, NH$_2$), 5.89 (d 1H, J=4.80 Hz, H-1'), 5.49 (d, 1H, J=5.84 Hz, OH-2'), 5.24 (d, 1H, J=5.15 Hz, OH-3'), 4.54 (q, 1H, J=5.14 Hz, H-2'), 4.15 (q, 1H, J=4.81 Hz, H-3'), 4.00 (q, 1H, J=4.46 Hz, H-4'), 3.58 (dq, 2H, J=9.27 Hz, 3.78 Hz, H-5'), 3.47 q, 2H, J=7.21 Hz, CH$_2$), 1.12 (t, 3H, J=7.20 Hz, CH$_3$); MS m/z 296 (M+H)$^+$; Anal. (C$_{12}$H$_{17}$N$_5$O$_4$.0.2 CH$_2$Cl$_2$) C, H, N.

N$^6$-cyclopentyl-5'-O-ethyladenosine (compound 73). Method B. The reaction was carried out with 6-chloro-9-(2,3-di-O-acetyl-5-O-ethyl-β-D-ribofuranosyl)-purine (62, 502 mg, 1.26 mmol) and cyclopentylamine (1.89 mmol, 187 μL). The mixture was purified by column chromatography (eluens 5% MeOH in CH$_2$Cl$_2$). Yield 316 mg (0.87 mmol, 69%), mp 134–136° C.; R$_f$ 0.49 (eluens 10% MeOH in CH$_2$Cl$_2$). The product was re-crystallized from CH$_3$CN; $^1$H NMR (DMSO-d$_6$) δ 8.31 (s, 1H, H-8), 8.19 (s, 1H, H-2), 7.72 (d, 1H, J=7.55 Hz, NH), 5.89 (d, 1H, J=5.15 Hz, H-1'), 5.55–5.25 (m, 2H, OH-2',3'), 4.53 (t, 1H, J=4.81 Hz, H-2'), 4.15 (t, 1H, J=2.40 Hz, H-3'), 4.01–3.96 (m, 1H, H-4'), 3.62-3.48 (m, 2H, H-5'), 3.46 (q, 2H, J=7.21 Hz, CH$_2$CH$_3$), 1.99–1.82 (m, 2H, cyclopentyl), 1.78–1.52 (m, 4H, cyclopentyl), 1.11 (t, 3H, J=7.21 Hz, CH$_3$); MS m/z 364 (M+H)$^+$; Anal. (C$_{17}$H$_{25}$N$_5$O$_4$.0.6 CH$_3$CN) C, H, N.

N$^6$-(3-Iodobenzyl)-5'-O-Ethyladenosine (compound 74). Method B. The reaction was carried out with 6-chloro-9-(2, 3-di-O-acetyl-5-O-ethyl-β-D-ribofuranosyl)-purine (62, 367 mg, 0.92 mmol) and 3-iodobenzylamine.HCl (1.38 mmol, 372 mg). The mixture was purified by column chromatography (eluens 5% MeOH in $CH_2Cl_2$). Yield 339 mg (0.66 mmol, 72%), mp 164–166° C.; $R_f$ 0.40 (10% MeOH in $CH_2Cl_2$). The product was re-crystallized from $CH_3CN$; $^1H$ NMR (DMSO-$d_6$) δ 8.45 (bs, 1H, NH), 8.37 (s, 1H, H-8), 8.21 (s, 1H, H-2), 7.71 (s, 1H, CCHCl), 7.57 (d, 1H, J=7.90 Hz, CCHCHCH), 7.34 (d, 1H, J=6.52 Hz, CCHCH), 7.09 (t, 1H, J=6.87 Hz, CCHCH), 5.91 (d, 1H, J=4.46 Hz, H-1'), 5.53 (d, 1H, J=5.49 Hz, OH-2'), 5.27 (d, 1H, J=4.80 Hz, OH-3'), 4.67–4.64 (m, 1H, $NHCH_2$), 4.56 (q, 1H, J=4.81 Hz, H-2'), 4.17 (q, 1H, J=4.81 Hz, H-3'), 4.00 (q, 1H, J=4.12 Hz, H-4'), 3.60 (dq, 2H, J=9.61 Hz, J=3.43 Hz, H-5'), 3.47 (q, 2H, J=6.52 Hz, $OCH_2CH_3$), 1.12 (t, 3,3 J=6.52 Hz, $CH_3$); MS m/z 512 (M+H)$^+$; Anal. ($C_{19}H_{22}IN_5O_4 \cdot 0.3 \, CH_3CN$) C, H, N.

2-Chloro-5'-O-ethyladenosine (compound 75). Method A. The reaction was carried out with 2,6-dichloro-9-(2,3-di-O-acetyl-5-O-ethyl-β-D-ribofuranosyl)-purine (63, 656 mg, 1.51 mmol). The mixture was purified by column chromatography (eluens 5% MeOH in $CH_2Cl_2$). Yield 388 mg (1.18 mmol, 78%), mp 117–119° C.; $R_f$ 0.50 (10% MeOH in $CH_2Cl_2$); $^1H$ NMR (DMSO-$d_6$) δ 8.34 (s, 1H, H-8), 7.83 (bs, 2H, $NH_2$), 5.81 (d, 1H, J=5.49 Hz, H-1'), 5.53 (d, 1H, J=5.83 Hz, OH-2'), 5.28 (d, 1H, J=5.14 Hz, OH-3'), 4.49 (q, 1H, J=4.81 Hz, H-2'), 4.13–4.01 (m, 1H, H-3'), 4.01–3.99 (m, 1H, H-4'), 3.62–3.42 (m, 2H, H-5'), 3.47 (q, 2H, J=6.87 Hz, $OCH_2$), 1.12 (t, 3H, J=6.87 Hz, $CH_3$); MS m/z 330 (M+)$^+$; Anal. ($C_{12}H_{16}ClN_5O_4 \cdot 0.4 \, CH_2Cl_2$) C, H, N.

$N^6$-cyclopentyl-2-Chloro-5'-O-ethyladenosine (compound 76). Method B. The reaction was carried out with 2,6-dichloro-9-(2,3-di-O-acetyl-5-O-ethyl-β-D-ribofuranosyl)-purine (63, 505 mg, 1.16 mmol) and cyclopentylamine (1.74 mmol, 172 μL). The mixture was purified by column chromatography (eluens 5% MeOH in $CH_2Cl_2$). Yield 323 mg (0.81 mmol, 70%), mp 114–116° C.; $R_f$ 0.55 (10% MeOH in $CH_2Cl_2$); $^1H$ NMR (DMSO-$d_6$) δ 8.34 (s, 1H, H-8), 8.32 (bs, 1H, NH), 5.82 (d, 1H, J=5.15 Hz, H-1'), 5.53 (d, 1H, J=5.18 Hz, OH-2'), 5.29 (d, 1H, J=5.15 Hz, OH-3'), 4.47–4.37 (m, 2H, CH, H-2'), 4.11–4.10 (m, 1H, H-3'), 4.00 (q, 1H, J=4.47 Hz, H-4'), 3.62–3.58 (m, 2H, H-5'), 3.47 (q, 2H, J=7.21 Hz, $CH_2CH_3$), 2.00–1.83 (m, 2H, cyclopentyl), 1.71–1.51 ((m, 4H, cyclopentyl), 1.12 (t, 3H, J=7.21 Hz, $CH_3$); MS m/z 399 (M+H)$^+$; Anal. ($C_{17}H_{24}ClN_5O_4$) C, H, N.

$N^6$-(3-iodobenzyl)-2-Chloro-5'-O-ethyladenosine (compound 77). Method B. The reaction was carried out with 2,6-dichloro-9-(2,3-di-O-acetyl-5-O-ethyl-β-D-ribofuranosyl)-purine (63, 375 mg, 0.87 mmol) and 3-iodobenzylamine.HCl (1.31 mmol, 352 mg). The mixture was purified by column chromatography (eluens 5% MeOH in $CH_2Cl_2$). Yield 366 mg (0.67 mmol, 77%), mp 80–82° C.; $R_f$ 0.53 (10% MeOH in $CH_2Cl_2$); $^1H$ NMR (DMSO-$d_6$) δ 8.97 (bs, 1H, NH), 8.40 (s, 1H, H-8), 7.74 (s, 1H, CCHCl), 7.60 (d, 1H, J=6.87 Hz, CCHCHCH), 7.35 (d, 1H, J=8.24 Hz, CCHCH), 7.12 (t, 1H, J=7.21 Hz, CCHCH), 5.84 (d, 1H, =4.46 Hz, H-1'), 5.56 (d, 1H, J=5.49 Hz, OH-2'), 5.30 (d, 1H, J=5.15 Hz, OH-3'), 4.60 (d, 2H, J=4.46 Hz, $NHCH_2$), 4.51 (d, 1H, J=5.15 Hz, H-2'), 4.14–4.11 (m, 1H, H-3'), 4.02 (q, 1H, J=3.43 Hz, H-4'), 3.63–3.58 (m, 2H, H-5'), 3.49 (q, 2H, J=6.52 Hz, $CH_2CH_3$), 1.13 (t, 3H, J=6.52 Hz, $CH_3$); MS m/z 546 (+H)$^+$; Anal. ($C_{19}H_{21}ClIN_5O_4 \cdot 0.8 \, HCON(CH_3)_2$) C, H, N.

$N^6$-Cyclopentyl-5'-O-Cyclopropyladenosine (compound 78). Method A. The reaction was carried out with 6-chloro-9-(2,3-di-O-acetyl-5-O-cyclopropyl-β-D-ribofuranosyl)-purine (64, 334 mg, 0.81 mmol). The mixture was purified by column chromatography (eluens 5% MeOH in $CH_2Cl_2$). Yield 172 mg (0.56 mmol, 69%), mp 130–132° C.; $R_f$ 0.49 (10% MeOH in $CH_2Cl_2$); $^1H$ NMR (DMSO-$d_6$) δ 8.27 (s, 1H, H-8), 8.14 (s, 1H, H-2), 7.28 (bs, 2H, $NH_2$), 5.87 (d, 1H, J=4.80 Hz, H-1'), 5.50 (d, 1H, J=5.84 Hz, OH-2'), 5.26 (d, 1H, J=5.49 Hz, OH-3'), 4.56 (q, 1H, J=4.81 Hz, H-2'), 4.10 (q, 1H, J=4.47 Hz, H-3'), 3.99 (q, 1H, J=3.78 Hz, H-4'), 3.67–3.59 (m, 2H, H-5'), 0.44–0.40 (m, 4H, $OCH_2CH_2$); MS m/z 308 (M+H)$^+$; Anal. ($C_{13}H_{17}N_5O_4 \cdot 0.2 \, CH_2Cl_2$) C, H, N.

$N^6$-Cyclopentyl-5'-O-cyclopropyladenosine (compound 79). Method B. The reaction was carried out wit 6-chloro-9-(2,3-di-O-acetyl-5-cyclopropyl-β-D-ribofuranosyl)-purine (64, 273 mg, 0.66 mmol) and cyclopentylamine (1.00 mmol, 98 μl). The mixture was purified by column chromatography (eluens 5% MeOH in $CH_2Cl_2$). Yield 173 mg (0.46 mmol, 70%), mp 126–128° C.; $R_f$ 0.53 (10% MeOH in $CH_2Cl_2$). The product was recrystallized from $(C_2H_5)_2O$; $^1H$ NMR (MeOD) δ 8.17 (s, 1H, H-8), 8.13 (s, 1H, H-2), 5.94 (d, 1H, J=4.46 Hz, H-1'), 4.44 (t, 1H, J=4.80 Hz, H-2'), 4.18 (t, 1H, J=5.15 Hz, H-3'), 4.11–4.06 (m, 1H, H-4'), 3.69 (q, 2H, J=9.95 Hz, H-5'), 3.24–3.19 (m, 1H, CH), 2.11–1.82 (m, 2H, cyclopentyl), 1.72–1.50 (m, 6H, cyclopentyl), 0.48–0.39 (m, 4H, $CH_2CH_2$); MS m/z 376 (M+H)$^+$; Anal. ($C_{18}H_{25}N_5O_4 \cdot 0.5 \, (C_2H_5)_2O$) C, H, N.

$N^6$-(3-Iodobenzyl)-5'-O-cyclopropyladenosine (compound 80). Method B. The reaction was carried out with 6-chloro-9-(2,3-di-O-acetyl-5-O-cyclopropyl-β-D-ribofuranosyl)-purine (64, 196 mg, 0.48 mmol) and 3-iodobenzylamine.HCl (0.72 mmol, 193 mg). The mixture was purified by column chromatography (eluens 5% MeOH in $CH_2Cl_2$). Yield 186 mg (0.36 mmol, 74%), mp 110–112° C.; $R_f$ 0.49 (10% MeOH in $CH_2Cl_2$); $^1H$ NMR (DMSO-$d_6$) δ 8.43 (bs, 1H, NH), 8.31 (s, 1H, H-8), 8.21 (s, 1H, H-2), 7.71 (s, 1H, CCHCl), 7.57 (d, 1H, J=7.55 Hz, CCHCHCH), 7.34 (d, 1H, J=7.89 Hz, CCHCH), 7.09 (t, 1H, J=7.90 Hz, CCHCH), 5.89 (d, 1H, J=5.15 Hz, H-1'), 5.49 (d, 1H, J=5.83 Hz, OH-2'), 5.27 (d, 1H, J=5.15 Hz, OH-3'), 4.68–4.55 (m, 2H, $NHCH_2$), 4.57 (q, 1H, J=5.49 Hz, H-2'), 4.11 (q, 1H, J=4.46 Hz, H-3'), 4.00 (q, 1H, J=4.11 Hz, H-4'), 3.67–3.62 (m, 2H, H-5'), 0.45–0.40 (m, 4H, $CH_2CH_2$); MS m/z 524 (M+H)$^+$; Anal. ($C_{20}H_{22}IN_5O_4 \cdot 0.7 \, CH_3OH$) C, H, N.

2-Chloro-5'-O-cyclopropyladenosine (compound 81). Method A. The reaction was carried out with 2,6-dichloro-9-(2,3-di-O-acetyl-5-O-cyclopropyl-β-D-ribofuranosyl)-purine (65, 649 mg, 1.46 mmol). The mixture was purified by column chromatography (eluens 5% MeOH in $CH_2Cl_2$). Yield 379 mg (1.11 mmol, 76%), mp 122–124° C.; $R_f$ 0.32 (10% MeOH in $CH_2Cl_2$); $^1H$ NMR (DMSO-$d_6$) δ 8.29 (s, 1H, H-8), 7.83 (bs, 2H, $NH_2$), 5.79 (d, 1H, J=5.49 Hz, H-1'), 5.52 (d, 1H, J=6.18 Hz, OH-2'), 5.29 (d, 1H, J=5.29 Hz, OH-3'), 4.51 (q, 1H, J=5.84 Hz, H-2'), 4.08–3.99 (m, 2H, H-3',4'), 3.68–3.63 (m, 2H, H-5'), 0.45–0.41 (m, 4H, $CH_2CH_2$); MS m/z 342 (M+H)$^+$; Anal. ($C_{13}H_{16}ClIN_5O_4 \cdot 0.8 \, HCON(CH_3)_2$) C, H, N.

$N^6$-cyclopentyl-2-Chloro-5'-O-cyclopropyladenosine (compound 82). Method B. The reaction was carried out with 2,6-dichloro-9-(2,3-di-O-acetyl-5-O-cyclopropyl-β-D-ribofuranosyl)-purine (65, 543 mg, 1.22 mmol) and cyclopentylamine (1.83 mmol, 180 μL). The mixture was purified by column chromatography (eluens 5% MeOH in $CH_2Cl_2$). Yield 400 mg (0.98 mmol, 80%), mp 104–106° C.; $R_f$ 0.51 (10% MeOH in $CH_2Cl_2$). The product was re-crystallized from $(C_2H_5)_2O$; $^1H$ NMR (DMSO-$d_6$) δ 8.34 (bs, 1H, NH), 8.28 (s, 1H, H-8), 5.81 (d, 1H, J=5.15 Hz, H-1'), 5.53 (d, 1H, J=5.84 Hz, OH-2'), 5.29 (d, 1H, J=5.15 Hz, OH-3'), 4.50 (q, 1H, J=5.15 Hz, H-2'), 4.50–4.47 (m, 1H, CH), 4.09–3.99 (m, 2H, H-3',4'), 3.68–3.63 (m, 2H, H-5'), 1.94–1.89 (m, 2H, cyclopentyl), 1.71-1.50 (m, 4H, cyclopentyl), 0.46–0.41 (m, 4H, OCHCH$_2$CH$_2$); MS m/z 410 (M+H)$^+$; Anal. (C$_{18}$H$_{24}$ClN$_5$O$_4$.0.2(C$_2$H$_5$)$_2$O) C, H, N.

N$^6$-(3-Iodobenzyl)-2-chloro-5'-O-cyclopropyladenosine (compound 83). Method B. The reaction was carried out with 2,6-dichloro-9-(2,3-di-O-acetyl-5-O-cyclopropyl-β-D-ribofuranosyl)-purine (65, 483 mg, 1.08 mmol) and 3-iodobenzylamine.HCl (1.63 mmol, 439 mg). The mixture was purified by column chromatography (eluens 5% MeOH in CH$_2$Cl$_2$). Yield 435 mg (0.78 mmol, 72%), mp 94–96° C.; R$_f$ 0.49 (10% MeOH in CH$_2$Cl$_2$); $^1$H NMR (DMSO-d$_6$) δ 8.93 (t, 1H, J=6.18 Hz, NH), 8.33 (s, 1H, H-8), 7.73 (s, 1H, CCHCl), 7.59 (d, 1H, J=7.90 Hz, CCHCHCH), 7.34 (d, 1H, J=7.55 Hz, CCHCH), 7.11 (t, 1H, J=7.55 Hz, CCHCH), 5.82 (d, 1H, J=5.14 Hz, H-1'), 5.54 (d, 1H, J=5.84 Hz, OH-2'), 5.30 (d, 1H, J=5.15 Hz, OH-3'), 4.61–4.48 (m, 3H, H-2', NHCH$_2$), 4.09–3.98 (m, 2H, H-3',4'), 3.68–3.58 (m, 2H, H-5'), 0.45–0.41 (m, 4H, cyclopropyl); MS m/z 559 (M+H)$^+$; Anal. (C$_{20}$H$_{21}$ClIN$_5$O$_4$.0.5 H$_2$O) C, H, N.

Elemental analyses for compounds 66–83 is provided herebelow:

TABLE 4

Elemental analysis

| No | Mol. Formula | Atom Calculated | Determined |
|---|---|---|---|
| 66 | C$_{11}$H$_{15}$N$_5$O$_4$.0.5 H$_2$O | C 45.51% | C 45.46% |
|  |  | H 5.56% | H 5.94% |
|  |  | N 24.13% | N 24.37% |
| 67 | C$_{16}$H$_{23}$N$_5$O$_4$.0.7 CH$_3$CN | C 55.27% | C 55.08% |
|  |  | H 6.69% | H 6.56% |
|  |  | N 21.11% | N 21.23% |
| 68 | C$_{18}$H$_{20}$IN$_5$O$_4$ | C 43.48% | C 43.82% |
|  |  | H 4.05% | H 3.94% |
|  |  | N 14.08% | N 13.74% |
| 69 | C$_{11}$H$_{14}$ClN$_5$O$_4$.1.0 CH$_2$Cl$_2$ | C 35.97% | C 35.97% |
|  |  | H 4.03% | H 4.21% |
|  |  | N 17.48% | N 17.65% |
| 70 | C$_{16}$H$_{22}$ClN$_5$O$_4$.0.1 CH$_2$Cl$_2$ | C 49.28% | C 49.65% |
|  |  | H 5.70% | H 5.52% |
|  |  | N 17.85% | N 18.38% |
| 71 | C$_{18}$H$_{19}$ClIN$_5$O$_4$.0.3 CH$_3$COCH$_3$ | C 41.33% | C 41.71% |
|  |  | H 3.82% | H 3.45% |
|  |  | N 12.75% | N 13.00% |
| 72 | C$_{12}$H$_{17}$N$_5$O$_4$.0.2 CH$_2$Cl$_2$ | C 46.92% | C 46.56% |
|  |  | H 5.62% | H 5.90% |
|  |  | N 22.43% | N 22.09% |
| 73 | C$_{17}$H$_{25}$N$_5$O$_4$.0.6 CH$_3$CN | C 56.33% | C 56.19% |
|  |  | H 6.96% | H 6.89% |
|  |  | N 20.21% | N 20.24% |
| 74 | C$_{19}$H$_{22}$IN$_5$O$_4$.0.3 CH$_3$CN | C 44.95% | C 45.37% |
|  |  | H 4.41% | H 4.60% |
|  |  | N 14.18% | N 13.94% |
| 75 | C$_{12}$H$_{16}$ClN$_5$O$_4$.0.4 CH$_2$Cl$_2$ | C 40.94% | C 40.80% |
|  |  | H 4.66% | H 5.03% |
|  |  | N 19.25% | N 19.29% |
| 76 | C$_{17}$H$_{24}$ClN$_5$O$_4$ | C 51.32% | C 51.65% |
|  |  | H 6.08% | H 5.72% |
|  |  | N 17.60% | N 17.85% |
| 77 | C$_{19}$H$_{21}$ClIN$_5$O$_4$.0.8 HCON(CH$_3$)$_2$ | C 42.53% | C 42.89% |
|  |  | H 4.44% | H 4.43% |
|  |  | N 13.44% | N 13.04% |
| 78 | C$_{13}$H$_{17}$N$_5$O$_4$.0.8 H$_2$O | C 48.56% | C 48.66% |
|  |  | H 5.82% | H 5.69% |
|  |  | N 21.78% | N 21.53% |
| 79 | C$_{18}$H$_{25}$N$_5$O$_4$.0.5 (C$_2$H$_5$)$_2$O | C 58.23% | C 58.50% |
|  |  | H 7.33% | H 6.87% |
|  |  | N 16.98% | N 17.05% |
| 80 | C$_{20}$H$_{22}$IN$_5$O$_4$.0.7 CH$_3$OH | C 45.55% | C 45.65% |
|  |  | H 4.58% | H 4.38% |
|  |  | N 12.83% | N 12.70% |
| 81 | C$_{13}$H$_{16}$ClN$_5$O$_4$.0.8 HCON(CH$_3$)$_2$ | C 46.21% | C 46.21% |
|  |  | H 5.44% | H 5.36% |
|  |  | N 20.30% | N 20.20% |

TABLE 4-continued

Elemental analysis

| No | Mol. Formula | Atom Calculated | Determined |
|---|---|---|---|
| 82 | C$_{18}$H$_{24}$ClN$_5$O$_4$.0.2 (C$_2$H$_5$)$_2$O | C 53.16% | C 53.08% |
|  |  | H 6.17% | H 6.52% |
|  |  | N 16.49% | N 16.74% |
| 83 | C$_{20}$H$_{21}$ClIN$_5$O$_4$.0.5 H$_2$O | C 42.38% | C 42.46% |
|  |  | H 3.91% | H 4.11% |
|  |  | N 12.36% | N 12.26% |

Biology—General

Radioligand Binding Studies Measurements with [$^3$H] DPCPX in the absence of GTP were performed according to a protocol published previously (rat A$_1$).[33] Adenosine A$_{2A}$ receptor (rat) affinities were determined according to Gao et al.[34] Adenosine A$_3$ receptor affinities were determined essentially as described.[4,35] Briefly, assays were performed in 50/10/1 buffer (50 mM Tris/10 mM MgCl$_2$/1 mM ethylenediaminetetra-acetic acid (EDTA) and 0.01% 3-([3-cholamidopropyl]-dimethylammonio)-1-propanesulfonate (CHAPS)) in glass tubes and contained 50 μL of a HEK 293 cell membrane suspension (10–30 μg), 25 μl [$^{125}$I]AB MECA (final concentration 0.15 nM), and 25 μl of ligand. Incubations were carried out for 1 hr at 37° C. and were terminated by rapid filtration over Whatman GF/B filters, using a Brandell cell harvester (Brandell, Gaithersburg, Md.). Tubes were washed three times with 3 ml of buffer. Radioactivity was determined in a Beckman 5500B γ-counter. Nonspecific binding was determined in the presence of 10$^{-5}$ M R-PIA.

cAMP assay A$_1$ and A$_3$ CHO cells expressing either the human adenosine A$_1$ or A$_3$ receptor were grown overnight as a monolayer in 24 wells tissue culture plates (400 μl/well; 2×10$^5$ cells/well). cAMP generation was performed in Dulbecco's Modified Eagles Medium (DMEM)/N-2-hydroxyethylpiperazin-N'-2-ethansulfonic acid (HEPES) buffer (0.60 g HEPES/50 ml DMEM pH 7.4). To each well, washed two times with DMEM/HEPES buffer (250 μl), 100 μl adenosine deaminase (final concentration 5 IU/ml), 100 μl of a mixture of rolipram and cilostamide (final concentration each 50 μM) and 100 μl agonist (final concentration ±100 times the K$_i$ value) were added. After incubation for 40 minutes at 37° C., 100 μl forskolin (final concentration 10 μM) was added. After 15 minutes at 37° C., the reaction was terminated by removing the medium and adding 200 μL 0.1 M HCl. Wells were stored at −20° C. until assay The amounts of cAMP were determined after a protocol with cAMP binding protein[28] with the following minor modifications. As a buffer was used 150 mM K$_2$HPO$_4$/10 mM EDTA/0.2% Bovine Serum Albumine (BSA) at pH 7.5. Samples (20 μl+30 μl 0.1 M HCl) were incubated for at least 2.5 hours at 0° C. before filtration over Whatman GF/B filters. Filters were additionally rinsed with 2×2 ml TrisHCl buffer (pH 7.4, 4° C.). Filters were counted in Packard Emulsifier Safe scintillation fluid (3.5 ml) after 24 hours of extraction.

Data Analysis Apparent K$_i$ and EC$_{50}$ values were computed from the displacement curves by nonlinear regression of the competition curves with the software package Prism (Graph Pad, San Diego, Calif.).

All compounds were tested in radioligized binding assays to determine their affinities for the adenosine A$_1$ receptor in rat brain cortex, the A$_{2A}$ receptor in rat striatum and the human A$_3$ receptor as expressed in HEK 293 cells (Table 5).

For the adenosine $A_1$ receptor, the tritiated antagonist, [$^3$I]-1,3-dipropyl-8-cyclopentylxanthine ([$^3$H]DPCPX), and for the adenosine $A_{2A}$ receptor, the tritiated antagonist [$^3$H]ZM 241385 were used. [$^{125}$I]AB-MECA, an $A_3$ receptor agonist, was also used. Displacement experiments were performed in the absence of GTP.

All compounds were also tested in functional assays. First, the ability of the compounds (66–83) to inhibit the forskolin (10 µM) induced cAMP production via human adenosine adenosine $A_1$ receptors expressed in CHO cells or by human adenosine $A_3$ receptors expressed in HEK 293 cells was assessed. Second, the modulation of guanosine-5'-O-(3-[$^{35}$S]thio)triphosphate ([$^{35}$S]GTPγS) binding to cell membranes was determined when compounds 66–83 bound to the receptors. Membrane preparations from rat brain cortex ($A_1$ receptors) and from CHO cells stably transfected with human adenosine $A_3$ receptors were used (no significant stimulation occurred with membranes prepared from the HEK 293 cells used in the binding studies).

Results and Discussion

Selective alkylation at the 5'-position of adenosine, or one of its derivatives, is rather difficult, since one must be very careful to prevent alkylation at the more reactive nitrogen atoms present in the base moiety (except for the $N^6$ nitrogen, which is less reactive). Treatment of either 2',3'-O-isopropylideneadenosine or 2',3'-O-isopropylideneinosine with KOH, 18-crown-6 and iodomethane[50,51] yielded the N1-methylated derivative or a mixture of the N1-methylated product together with the N1,5'-dimethylated one, respectively. Refluxing a 5'-chloro-5'-deoxyadenosine derivative in methanolate regained only starting material. Therefore, alkylation of the ribose first, and then coupling the product to the appropriate heterocyclic base was selected as the preferred procedure and subsequently perform other reactions.

Protection of the 1-, 2- and 3-hydroxyl groups of D-ribose (49) was performed according to a method described by Leonard et al.[48] with a modification. D-ribose was dissolved in a mixture of acetone, MeOH and 2,2-dimethoxypropane, and HCl gas was bubbled directly through the solution, instead of adding MeOH saturated with HCl gas. The protected β-sugar (50) was obtained in good yield (95%). For alkylation of the 5-hydroxyl group, 50 was dissolved in DMF and NaH under cooling (not in the case of cyclopropylbromide), and the appropriate alkylhalide was added at room temperature. Compounds 51–53 were obtained in 38–97% yield.

In general, benzoyl protecting groups at the 2-, 3- and 5-position of the sugar moiety have been used to improve the formation of 62-nucleosides over α-nucleosides in the glycosylation reaction, i.e. when the protected sugar is coupled to a heterocyclic base.[44] Hence, the isopropylidene protecting group of 51 was removed to obtain the methyl 5-O-methyl-D-ribofuranoside derivative. Subsequent treatment with benzoylchloride in $CH_2Cl_2$ and pyridine yielded the desired methyl 2,3-di-O-benzoyl-5-O-methyl-D-ribofuranoside, although is was difficult to remove the excess of benzoylchloride.[52] The conversion of the 1-O-methyl group into a 1-O-acetyl group succeeded in reasonable yield by treatment of methyl 2,3-di-O-benzoyl-5-O-methyl-D-ribofuranoside with acetic acid, acetic, anhydride and sulfuric acid.[52] Since this method is quite laborious, the possibility of using a fully acetyl protected sugar was explored as well. Removal of the protecting groups of compounds 51–53 with aqueous sulfuric acid (0.02 M) and EtOH gave, besides the desired product, also a significant amount of the 1-O-ethyl substituted derivative. Instead, refluxing 51–53 with 0.04 M HCl and subsequent neutralization with $BaCO_3$ gave compounds 54–56 in good yields.[49] Introduction of the acetyl protecting groups to give 57–59 was also achievable. The coupling of 57 with 6-chloropurine according to Vorbrüggen led to the formation of 6-chloro-9-(2,3-di-O-acetyl-5-O-methyl-β-D-ribofuranosyl)-purine (60) in a satisfactory yield (48%), suggesting that the laborious benzoyl-protection was not necessary. Compounds 61–65 were obtained in even higher yields (65–84%) starting from 57–59, and from NMR spectroscopy it was concluded that only the β-congener was formed. The Lewis acid used in the Vorbrüggen method, trimethylsilyl-trifluoromethane sulfonate (TMS triflate), belongs to a relatively new family of acids. It was compared with the more traditional Lewis acid stannic chloride ($SnCl_4$), described as high-yielding.[53] Both Lewis acids led to similar yields of the coupled product as a result of the glycosylation of 6-chloro-purine and commercially available 1-O-acetyl-2,3,5-tri-O-benzoyl-β-D-ribofuranose. Finally, amination of compounds 60–65 with either $EtOH/NH_3$, cyclopentylamine or 3-iodobenzylamine gave the unprotected $N^6$,5'-di or $N^6$,C2,5'-trisubstituted adenosine derivatives 66–83.[89]

Table 5 displays radioligand binding data for all synthesized di- and tri-substituted final products, wherein the substituents are as shown in general formula (I) and W represents an oxygen atom.

TABLE 5

Radioligand binding assay
$K_i$ (nM) or % displacement at $10^{-5}$ M

| No | $R_1$ | $R_2$ | $R_3$ | $A_1$[a] | $A_{2A}$[b] | $A_3$[c] | $A_1/A_3$ |
|---|---|---|---|---|---|---|---|
| CPA | H | H | c-$C_5H_9$ | 7.14 ± 2.30 | 45.9% | 281 ± 56 | 0.02 |
| 2-Cl-CPA | H | Cl | c-$C_5H_9$ | 9.47 ± 0.86 | 53.1% | 204 ± 44 | 0.05 |
| IB MECA | — | H | $CH_2(C_6H_4)$-m-I | 1400 ± 240 | 39.4% | 6.9 ± 0.2 | 208 |
| 2-Cl-IB MECA | — | Cl | $CH_2(C_6H_4)$-m-I | 710 ± 41 | 23.5% | 7.2 ± 0.9 | 98 |
| 66 | Me | H | H | 164 ± 37 | 261 ± 65 | 40.3 ± 8.1 | 4.1 |
| 67 | Me | H | c-$C_5H_9$ | 33.7 ± 6.9 | 366 ± 109 | 79.0 ± 30.0 | 0.4 |
| 68 | Me | H | $CH_2(C_6H_4)$-m-I | 179 ± 40 | 373 ± 80 | 4.2 ± 0.5 | 42.6 |
| 69 | Me | Cl | H | 169 ± 30 | 284 ± 55 | 28.3 ± 13.0 | 6.0 |
| 70 | Me | Cl | c-$C_5H_9$ | 16.3 ± 1.3 | 1390 ± 140 | 44.9 ± 4.9 | 0.4 |
| 71 | Me | Cl | $CH_2(C_6H_4)$-m-I | 112 ± 10 | 527 ± 21 | 7.3 ± 0.2 | 15.3 |
| 72 | Et | H | H | 2300 ± 320 | 415 ± 69 | 23.3 ± 3.9 | 98.7 |
| 73 | Et | H | c-$C_5H_9$ | 27.8 ± 2.2 | 33.9% | 32.3 ± 9.2 | 0.9 |
| 74 | Et | H | $CH_2(C_6H_4)$-m-I | 198 ± 36 | 40.4% | 3.3 ± 1.0 | 60.0 |

TABLE 5-continued

Radioligand binding assay
$K_i$ (nM) or % displacement at $10^{-5}$ M

| No | $R_1$ | $R_2$ | $R_3$ | $A_1{}^a$ | $A_{2A}{}^b$ | $A_3{}^c$ | $A_1/A_3$ |
|---|---|---|---|---|---|---|---|
| 75 | Et | Cl | H | 327 ± 15 | 659 ± 168 | 15.1 ± 6.9 | 21.7 |
| 76 | Et | Cl | c-$C_5H_9$ | 27.1 ± 1.8 | 1730 ± 700 | 67.0 ± 44.6 | 0.4 |
| 77 | Et | Cl | $CH_2(C_6H_4)$-m-I | 254 ± 28 | 848 ± 60 | 7.4 ± 1.0 | 34.3 |
| 78 | c-Prop | H | H | 575 ± 52 | 739 ± 16 | 45.6 ± 7.4 | 12.6 |
| 79 | c-Prop | H | c-$C_5H_9$ | 40.5 ± 6.4 | 24.3% | 104 ± 20 | 0.4 |
| 80 | c-Prop | H | $CH_2(C_6H_4)$-m-I | 733 ± 36 | 43.7% | 9.1 ± 1.9 | 80.5 |
| 81 | c-Prop | Cl | H | 595 ± 84 | 885 ± 89 | 26.7 ± 4.3 | 22.3 |
| 82 | c-Prop | Cl | c-$C_5H_9$ | 80.8 ± 12.0 | 34.6% | 86.0 ± 15.5 | 0.9 |
| 83 | c-Prop | Cl | $CH_2(C_6H_4)$-m-I | 1430 ± 200 | 38.7% | 20.5 ± 8.1 | 69.8 |

[a]Displacement of [$^3$H]DPCPX from rat cortical membranes.[24,33]
[b]Displacement of [$^3$H]ZM241385 from rat striatal membranes.[23,34]
[c]Displacement of [$^{125}$I]AB MECA from the human $A_3$ receptor expressed in HEK 293 cells.[26,35]

From this table, it is evident that most compounds had lower affinity for the adenosine $A_{2A}$ receptor than for the adenosine $A_1$ or $A_3$ receptors. Compounds with an unsubstituted $N^6$ amino group (66, 69, 72, 75, 78, 81) showed adenosine $A_3$ receptor selectivity compared to $A_1$, with $A_1/A_3$ selectivity ratios ranging from 4.1 for compound 66 to 98.7 for compound 72. A cyclopentyl group at the $N^6$-position induced high adenosine $A_1$ receptor affinities and also the highest selectivity for the $A_1$ receptor, whereas the $N^6$-(3-iodobenzyl) adenosine derivatives had the highest adenosine $A_3$ receptor affinities and were highly selective for this receptor, in line with earlier reports on these $N^6$-substituents.[1,2,5] In general, the adenosine $A_1$ receptor affinities were unchanged or increased (up to 2-fold) when a chlorine was introduced at the 2-position, with a concomitant slight increase in adenosine $A_1$ receptor selectivity (up to 4-fold). The introduction of chlorine at the 2-position had more variable effects on the affinity and selectivity for the adenosine $A_3$ receptor. The adenosine $A_3$ receptor affinities of the $N^6$-unsubstituted derivatives were slightly increased, whereas for the $N^6$-(3-iodobenzyl) substituted compounds they were decreased somewhat. The selectivity for the adenosine $A_3$ receptor was decreased up to approx. 4-fold, when chlorine was introduced at C2. The effect of chlorine at the 2-position on receptor affinity was difficult to predict in the case of substituted adenosines. It has been shown that for both CPA and $N^6$-(3-iodobenzyl)adenosine the affinity and selectivity for the adenosine $A_1$ receptor is increased when compared to the $A_{2A}$ receptor.[54] However, when chlorine was introduced at the 2-position of 5'-N-methylcarboxamido-substituted $N^6$-(3-iodobenzyl) adenosine[55] the affinity for both the adenosine $A_1$ and $A_{2A}$ receptors was decreased, while $A_3$ receptor affinity increased. On the contrary, in the present study introduction of chlorine at the 2-position of 5'-O-alkyl substituted derivatives slightly decreased adenosine $A_3$ receptor selectivity of the compounds compared to the $A_1$ receptor.

The 5'-substituents also influenced the affinity and selectivity of the compounds. For the adenosine $A_1$ receptor the compounds with a 5'-O-methyl group had the highest receptor affinities, whereas the 5'-O-cyclopropyl substituted derivatives displayed the lowest affinities in most cases. Only within the $N^6$,C2-unsubstituted series (66, 72, 78) 5'-O-ethyl-adenosine had the lowest affinity for the adenosine $A_1$ receptor. In case of the adenosine $A_3$ receptor, the derivatives with a 5'-O-ethyl substituent had the highest receptor affinities. The adenosine $A_3$ receptor affinities of the 5'-O-methyl substituted derivatives were equal or somewhat higher than the 5'-O-cyclopropyl substituted ones. Although a 5'-O-cyclopropyl group is tolerated fairly well on both the adenosine $A_1$ and $A_3$ receptor ($K_i$ values in the low nanomolar range), smaller groups seemed to be preferred, e.g. 5'-O-methyl for the adenosine $A_1$ receptor and 5'-O-ethyl for the $A_3$ receptor. The 5'-O-methyl group induced the highest adenosine $A_1$ receptor selectivity in most cases (within the series containing the same $N^6$- and C2-substituents), whereas the 5'-O-cyclopropyl induced most often the highest adenosine $A_3$ receptor selectivity compared to $A_1$. The compounds with a 5'-O-ethyl substituent had higher affinities than those with a 5'-O-methyl for the adenosine $A_3$ receptor, and had the highest selectivity for this receptor in most cases as well, compared to the $A_{2A}$ receptor. Although MECA has been described to have higher affinity (and selectivity) than NECA for the adenosine $A_3$ receptor compared to the $A_{2A}$ receptor, as demonstrated herein the adenosine $A_3$ receptor accommodates the rather large 5'-alkylthio substituents better than the smaller ones (5'-methylthio). The results disclosed herein show that the adenosine $A_3$ receptor is well capable of accommodating large 5'-substituents. Finally, compound 74 displayed a higher affinity for the adenosine $A_3$ receptor ($K_i$ value of 3.3 nM) than both reference compounds IB-MECA and 2-Cl-IB-MECA, although its selectivity for the adenosine $A_3$ compared to the $A_1$ receptor was somewhat less.

In Table 6 the ability of the compounds to inhibit forskolin-induced (10 μM) cAMP production is given.

TABLE 6 inhibition[a] of forskolin-induced cAMP

| No | $R_1$ | $R_2$ | $R_3$ | % inhib. $A_1{}^b$ | % inhib. $A_3{}^c$ |
|---|---|---|---|---|---|
| CPA | — | — | — | 69 ± 3 | — |
| Cl-IB-MECA | — | — | — | — | 83 ± 1 |
| 66 | Me | H | H | 75 ± 3 | 76 ± 2 |
| 67 | Me | H | c-$C_5H_9$ | 74 ± 4 | 58 ± 6 |
| 68 | Me | H | $CH_2(C_6H_4)$-m-I | 53 ± 10 | 33 ± 9 |
| 69 | Me | Cl | H | 78 ± 4 | 69 ± 3 |
| 70 | Me | Cl | c-$C_5H_9$ | 73 ± 4 | 42 ± 6 |
| 71 | Me | Cl | $CH_2(C_6H_4)$-m-I | 37 ± 15 | 17 ± 7 |
| 72 | Et | H | H | 57 ± 11 | 65 ± 7 |
| 73 | Et | H | c-$C_5H_9$ | 69 ± 6 | 37 ± 6 |
| 74 | Et | H | $CH_2(C_6H_4)$-m-I | 6 ± 21 | 11 ± 6 |
| 75 | Et | Cl | H | 67 ± 7 | 51 ± 5 |
| 76 | Et | Cl | c-$C_5H_9$ | 62 ± 6 | 31 ± 9 |
| 77 | Et | Cl | $CH_2(C_6H_4)$-m-I | −72 ± 38[#] | 7 ± 4 |
| 78 | c-Prop | H | H | 61 ± 2 | 59 ± 6 |

TABLE 6-continued inhibition[a] of forskolin-induced cAMP

| No | $R_1$ | $R_2$ | $R_3$ | % inhib. $A_1$[b] | % inhib. $A_3$[c] |
|----|-------|-------|-------|-------------------|-------------------|
| 79 | c-Prop | H  | c-$C_5H_9$ | 62 ± 4 | 26 ± 7 |
| 80 | c-Prop | H  | $CH_2(C_6H_4)$-m-I | −104 ± 22[#] | 10 ± 12 |
| 81 | c-Prop | Cl | H | 49 ± 9 | 44 ± 8 |
| 82 | c-Prop | Cl | c-$C_5H_9$ | 43 ± 9 | 19 ± 7 |
| 83 | c-Prop | Cl | $CH_2(C_6H_4)$-m-I | −118 ± 41[#] | −2.6 ± 4 |

[a]percentage inhibition (±SEM, n = 3)
[b]compared to the reference full agonist CPA (10 μM) in $A_1$ CHO cells
[c]compared to the reference full agonist Cl-IB-MECA (10 μM) All compounds were tested at ± 100 × $K_i$ value.
[#]seemed to behave as inverse (partial) agonist in this assay Table 6 shows that compounds within the three $N^6$-substituted series showed similar trends in inhibition of the forskolin-induced cAMP production via the adenosine $A_1$ receptor. Compounds with an intact amino group at the 6-position and the $N^6$-cyclopentyl substituted derivatives were able to inhibit the cAMP production to a similar extent, almost as well as the reference full agonist CPA, whereas the $N^6$-(3-iodobenzyl) substituted derivatives inhibited the forskolin-induced cAMP production somewhat less. Compound 68 had a lower intrinsic activity than compounds 66 and 67, while only the $N^6$-substituent is different, implicating that a 3-iodobenzyl group at $N^6$ can induce partial agonism for the adenosine $A_1$ receptor. Furthermore, within the three $N^6$-substituted series the 5'-O-methyl substituted derivatives had highest intrinsic activities compared to the 5'-O-ethyl and 5'-O-cyclopropyl substituted ones. The latter compounds displayed the lowest intrinsic activities and behaved as partial agonists for the adenosine $A_1$ receptor in this assay. Here, the effect of the chlorine at the C2-position on the intrinsic activity is not unambiguous.

Example 3

Materials

Compounds 34, 37, 69 and 70 were dissolved in dimethylsulfoxide (DMSO) and further diluted either in RPMI (for in vitro studies) or in PBS (for the in vivo studies).

Methods

G-CSF in Human Cord Blood

Human cord blood samples were collected, from delivery room immediately after birth. Experiments were performed in accordance with the guidelines established by the Institutional Helsinky Committee at the Rabin Medical Center, Petah Tikva, Israel. The sample was loaded on ficoll histopaque in equal volume and centrifuged for 20 minutes at 1700 RPM. Mononuclear cells were collected, wash twice with PBS and incubated (1.5×10[6] cell/ml) in RPMI supplemented with 20% of Human AB serum and 50 μM of the various compounds for 48 hr. Supernatants were collected, aliquoted and stored in −20° C. The level of G-CSF was measured using a commercial human ELISA kit (R&D systems, Minneapolis, Minn.).

Bone Marrow Cells Proliferation Assay

Bone marrow cells were obtained from the femur of ICR mice. Cells were disaggregated by passing them through a 25G needle. Cells (3×10[5]/well) were incubated with RPMI medium, containing 10% fetal bovine serum (FBS) (Biological Industries, Beit Haemek, Israel), in 96 microtiter plates for 48 hr, in the presence of the various compounds, at concentration of 10 μM. Cultures containing cells suspended in RPMI medium and 10% FBS served as control. In the last 18 hours of incubation, each well was pulsed with 1 μCi ³[H]-thymidine after which cells were harvested and ³[H]-thymidine uptake was determined in an LKB liquid scintillation counter (LKB, Piscataway, N.J., USA).

In vivo Studies

To examine the capability of the various compounds to elevate hematological parameters like the White Blood cells (WBC) and absolute neutrophil counts (ANC), the compounds were given to naive mice orally twice a day (each dose 150 μg/kg body weight) for two consecutive days. Blood samples were withdrawn 48 following the last compounds administration. White blood cells counts were carried out in a Coulter counter and differential cell counts were performed on smear preparations stained with May-Grunvald-Giemsa solution. Also serum samples were colleted for G-CSF measurements as described above.

Results and Discussion

Compounds 34, 37, 69 and 70 were evaluated for their activity as agonists of the A1 or A3 adenosine receptor, by determining their in vitro and in vivo effect on G-CSF production, as well as their effect of the proliferation of bone marrow cells, white blood cells and neutrophil cells.

FIG. 1 shows that the tested compounds were capable of inducing G-CSF production in vitro as compared to the control (no drug). The inducing effect was at times to a level similar to that obtained with the known A3 receptor agonist, IB-MECA.

Figure 2:
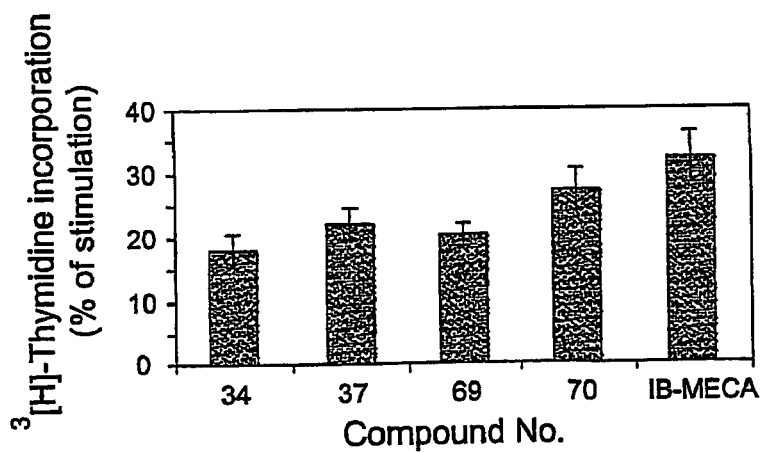
FIG. 2 is a bar graph showing results of in vitro assay in which proliferation of bone marrow cells was tested in the presence of 10 µM of the compound. In particular, the effect of compounds 34, 37, 69 and 70 (as referenced hereinbelow) on [$^3$H] thymidine incorporation was examined as compared to the effect of an adenosine A3 receptor agonist, IB-MECA, which served as the control.

In addition, the tested compounds were shown to induce bone marrow cell proliferation as determined by ³[H]-thymidine incorporation in cells incubated with the different compounds or with IB-MECA (as a positive control). The results are presented in FIG. 2.

Figure 3A:
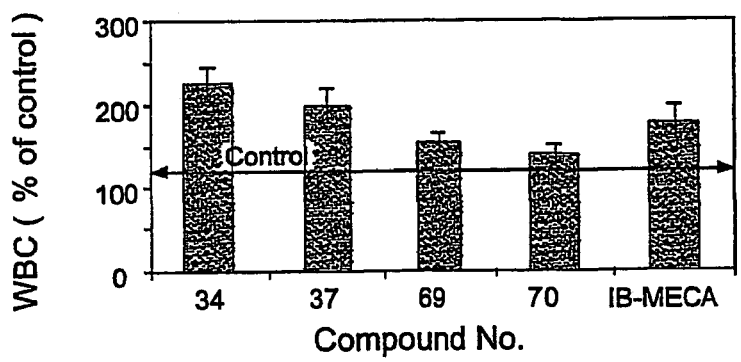
FIGS. 3A–3C are bar graphs showing results of in vivo assays in which the effect of some compounds of the invention on white blood cell count (FIG. 3A), absolute neutrophil counts (ANC) (FIG. 3B), and serum G-CSF levels (FIG. 3C) in naive mice inoculated with two daily doses of compounds 34, 37, 69 and 70 (as referenced hereinbelow) (150 µmole/kg body weight per dose).
Figure 3B:
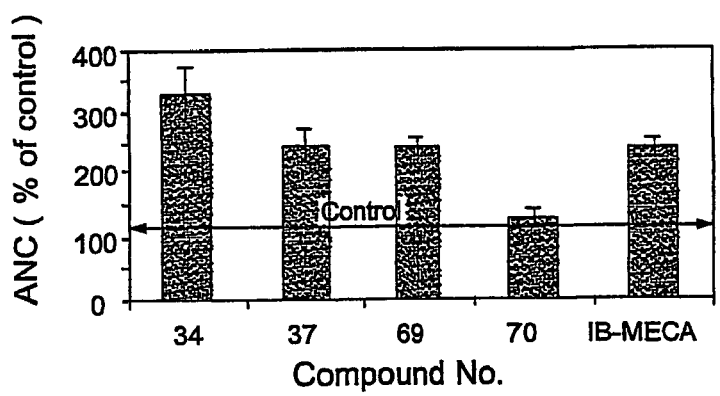
Figure 3C:
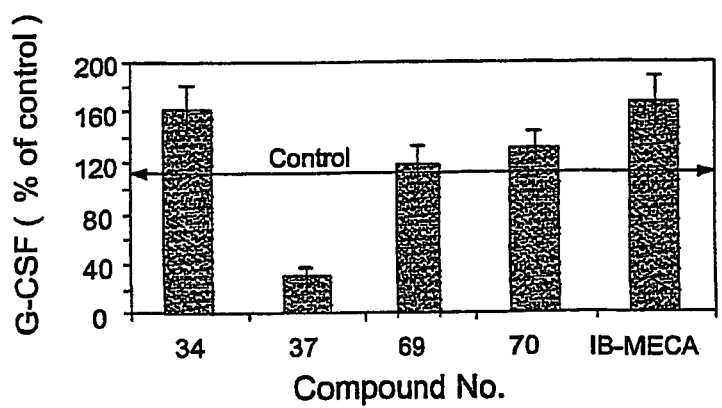

In vivo effect of the tested compounds is presented in FIGS. 3A, 3B and 3C. In particular, when the tested compounds were provided orally to mice, the levels of white blood cells, neutrophils and serum G-CSF were elevated as a result of the treatment.

The above results suggest that the tested compounds, i.e. compounds 34, 36, 69 and 70 may be agonists of the A1 or A3 adenosine receptor and thus have a therapeutic utility, e.g. in protecting against drug-induced myelotoxicity.

LIST OF REFERENCES

1. Van der Wenden, E. M., Carnielli, M., Roelen, H. C. P. F., Lorenzen, A., von Frijtag Drabbe Künzel, J. K., IJzerman, A. P., *J. Med. Chem.*, 1998, 41, 102–108.
2. Roelen, H., Veldman, N., Spek, A. L., von Frijtag Drabbe K☐nzel, J., Mathot, R. A., IJzerman, A. P., *J. Med. Chem.*, 1996, 39, 1463–1471.
3. Gallo-Rodriquez, C., Ji, X., Melman, N., Siegman, B. D., Sanders, L. H., Orlina, J., Fischer, B., Pu, Q., Olah, M. E., van Galen, P. J. M., Stiles, G. L., Jacobson, K. A., *J. Med. Chem.*, 1994, 37, 636–646.
4. Van Galen, P. J. M., Van Bergen, A. H., Gallo-Rodriquez, C., Melman, N., Olah, M. E., IJzerman, A. P., Stiles, G. L., Jacobson, K. A., *Mol. Pharmacol.*, 1994, 45, 1101–1111.
5. Van Tilburg, E. W., Von Frijtag Drabbe Künzel, J., Groote, M., Vollinga, R. C., Lorenzen, A., IJzerman, A. P., *J. Med. Chem.*, 1999, 42, 1393–1400.

6. Hutchison, A. J., Williams, M., deJesus, R, Yokoyama, R., Oei, H. H., Ghai, G. R., Webb, R. L., Zoganas, H. C., Stone, G. A., Jarvis, M. F., *J. Med. Chem.*, 1990, 33, 1919–1924.
7. Niiya; K., Olsson, R. A., Thompson, R. D., Silvia, S. K., Ueeda, M., *J. Med. Chem.*, 1992, 35, 4557–4561.
8. Cristalli, G., Eleuteri, A., Vittori, S., Volpini, R., Lohse, M. J., Klotz, K.-N., *J. Med. Chem.*, 1992, 35,2363–2368.
9. Klotz, K.-N., Camaioni, E., Volpini, R., Kachler, S., Vittori, S., Cristalli, G., *Naunyn-Schmiedeberg's Arch. Pharmacol.*, 1999, 360, 103–108.
10. Volpini, R., Camaioni, E., Costanzi, S., Vittori, S., Klotz, K.-N., Cristalli, G., *Nucleosides and Nucleotides*, 1999, 18, 2511–2520.
11. Clarke, W. P., Bond, R. A., The exclusive nature of intrinsic efficacy, *TiPS*, 1998, 19, 270–276.
12. Kenakin, T., *TiPS*, 1995, 16, 188–192.
13. Fuxe, K., Ferre, S., Zoli, M., Agnati, L. F, *Brain Res. Brain Res. Rev.*, 1998, 26, 258–273.
14. Kafka, S. H., Corbett, R., *Eur. J. Pharmacol.*, 1996, 295, 147–154.
15. Liang, B. T., Jacobson, K. A., *Proc. Natl. Acad. Sci. USA.*, 1998, 95, 6995–6999.
16. Jacobson, K. A., Lubitz, D. K. J. E. v., Daly, J. W., Fredholm, B. B., *TiPS*, 1996, 17, 108–113.
17. Jacobson, M. A., Bai, T. R, in *Purinergic approaches in experimental therapeutics*, Jacobson, K. A., Jarvis, M. F., Ed.; Wiley-Liss, Inc: New York, 1997; pp 315–331.
18. Robins, M. J., Uznanski, B., *Can. J. Chem.*, 1981, 59, 2601–2607.
19. Matsuda, A., Shinozaki, M., Miyasaka, T., Machida, H., Abiru, T., *Chem. Pharm. Bull.*, 1985, 33, 1766–1769.
20. Robins, M. J., Hansske, F., Wnuk, S. F., Kanai, T., *Can. J. Chem.*, 1991, 69, 1468–1474.
21. Nair, V., Young, D. A., *J. Org. Chem.*, 1984, 49,4340–4344.
22. Nair, V., Richardson, S. G., *Synthesis*, 1982, 670–673.
23. Srivastava, P. C., Robins, R. K., Meyer, R. B. J., in *Chemistry of nucleosides and nucleotides*, I. Townsend, L. B., Ed.; Plenum Press: New York, 1988; pp 113–282.
24. Verheyden, J. P. H., Moffatt, J. G., *J. Org. Chem.*, 1972, 37, 2289–2299.
25. Homma, H., Watanabe, Y., Abiru, T., Murayama, T., Nomura, Y., Matsuda, A., *J. Med. Chem.*, 1992, 35, 2881–2890.
26. Matsuda, A., Shinozaki, M., Yamaguchi, T., Homma, H., Nomoto, R., Miyasaka, T., Watanabe, Y., Abiru, T., Nucleosides and nucleotides. 103. 2-Alkynyladenosines: *J. Med. Chem.*, 1992, 35, 241–252.
27. Cristalli, G., Camaioni, E., Costanzi, S., Vittori, S., Volpini, R., Klotz, K. N., *Drug Dev. Res.*, 1998, 45, 176–181.
28. Ueeda, M., Thompson, R. D., Arroyo, L. H., Olsson, R. A., *J. Med. Chem.*, 1991, 34, 1340–1344.
29. De Zwart, M., Kourounakis, A., Kooijman, H., Spek, A. L., Link, R., von Frijtag Drabbe Künzel, J. K., IJzerman, A. P, *J. Med. Chem.*, 1999, 42, 1384–1392.
30. (30) Mogensen, J. P., Roberts, S. M., Bowler, A. N., Thomsen, C., Knutsen, L. J. S., *Bioorg. Med. Chem. Lett.*, 1998, 8, 1767–1770.
31. Chan, C., (GB), G. W., *PCT Int. Appl.* 104 pp. WO 99/38877 A2 990805, 1999.
32. Kull, B., Arslan, G., Nilsson, C., Owman, C., Lorenzen, A., Schwabe, U., Fredholm, B. B., *Biochem. Pharmacol*, 1999, 57, 65–75.
33. Pirovano, I. M., IJzerman, A. P., Van Galen, P. J. M., Soudijn, W., *Eur. J. Pharmacol.*, 1989, 172, 185–193.
34. Gao, Z.-G., IJzerman, A. P., *Biochem. Pharmacol.*, in press.
35. Olah, M. E., Gallo-Rodriquez, C., Jacobson, K. A., Stiles, G. L., *Mol. Pharmacol.*, 1994, 45, 978–982.
36. Van der Wenden, E. M., Hartog-Witte, H. R., Roelen, H. C. P. F., Von Frijtag Drabbe Künzel, J. K., Pirovano, I. M., Mathot, R. A. A., Danhof, M., Van Aerschot, A., Lidaks, M. J., IJzerman, A. P., Soudijn, W., *Eur. J. Pharmacol-Mol Pharmacol. Sect.*, 1995, 290, 189–199.
37. Liu, G.-S., Downey, J. M., Cohen, M. V., *In Purinergic approaches in experimental therapeutics*. Jacobson, K. A., Jarvis, M. F., Ed.; Wiley-Liss, Inc: New York, 1997; pp 153–172.
38. lLondos, C., Honner, R. C., Dhillon, G. S., *J. Biol. Chem.*, 1980, 260, 15139–15145.
39. Saloranta, C., Fransilla-Kallunki, A., Ekstrand, A., Taskinen, M.-R., Groop, L., *Diabetologia*, 1991, 34, 409–415.
40. IJzerman, A. P., Van der Wenden, E. M., von Frijtag Drabbe Künzel, J. K., Mathôt, R. A. A., Danhof, M., Borea, P. A., Varani, K., *Naunyn-Schmiedeberg's Arch. Pharmacol.*, 1994, 350, 638–645.
41. Lorenzen, A., Sebastiao, A. M., Sellink, A., Vogt, H., Schwabe, U., Ribeiro, J. A., IJzerman, A. P., *Eur. J. Pharmacol.*, 1997, 334, 299–307.
42. Van der Graaf, P. H., Van Schaick, E. A., Visser, S. A. G., De Greef, H. J. M. M., IJzerman, A. P;, Danhof, M., *J. Pharmacol, Exp. Ther.*, 1999, 290, 702–709.
43. Gin, J. B., Dekker, C. A., *Biochem.*, 1968, 7, 1413–1420.
44. Vorbrüggen, H., Höfle, G., *Chem. Ber.*, 1981, 114, 1256–1268.
45. Vorbrüggen, H., Krolikiewicz, K., Bennua, B., *Chem. Ber.*, 1981, 114, 1234–1255.
46. Lorenzen, A., Fuss, M., Vogt, H., Schwabe, U., *Mol. Pharmacol.*, 1993, 44, 115–123.
47. Lorenzen, A., Guerra, L., Vogt, H., Schwabe, U., *Mol. Pharmacol.*, 1996, 49, 915–926.
48. Leonard, N. J., Carraway, K. L., *J. Heterocycl. Chem.*, 1966, 3, 485–487.
49. Levene, P. A., Stiller, E. T *J. Biol. Chem.*, 1934, 187–201.
50. Bessodes, M., Shamsazar, J., Antonakis, K., *Synthesis*, 1988, 560–562.
51. McCall, M. J., Taylor, M. R., *Acta Cryst.*, 1976, B32, 1687–1691.
52. Visser, G. M., Thesis: "*Synthesis of some modified nucleotide derivatives and the possible role of mirror-image nucleotides in molecular evolution*". 1986, pp 52.
53. Saneyoshi, M., Satoh, E., *Chem. Pharm. Bull.*, 1979,27, 2518–2521.
54. Lohse, M. J., Klotz, K.-N., Schwabe, U, Cristalli, G., Vittori, S., Grifantini, M., *Naunyn-Schmiedeberg's Arch. Arch. Pharmacol.*, 1988, 337, 687–689.
55. Kim, H. O., Siddiqi, S. M., Olah, M. E., Stiles, G. L., K. A., J., *J. Med. Chem.*, 1994, 37, 3614–3621.

The invention claimed is:
1. A compound of the general formula (I):

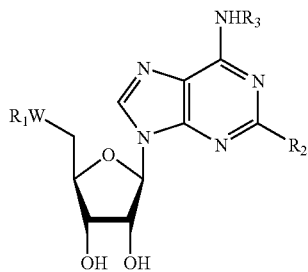

wherein
W represents an oxygen atom or a sulfur atom;
$R_1$ represents lower alkyl or lower cycloalkyl;
$R_2$ represents halogen, lower alkenyl, lower alkynyl or lower alkylidenehydrazino;
$R_3$ represents hydrogen, lower alkyl, lower cycloalkyl, (ar)alkyl, aryl or anilide; wherein said cycloalkyl aryl and (ar)alkyl may be substituted with one or more subtituents selected from halogen, hydroxyl, and hydroxyalkyl;
or a salt of said compound,
wherein when W is a sulfur atom, $R_1$ is a lower alkyl, $R_2$ is a halogen and $R_3$ is hydrogen, then $R_2$ is iodo.

2. The compound of claim 1, wherein W represents a sulfur atom, $R_1$ represents a lower alkyl group, $R_2$ represents an iodo and $R_3$ represents hydrogen.

3. The compound of claim 2, wherein W represents a sulfur atom, $R_1$ represents a lower alkyl selected from the group consisting of methyl, ethyl, n-propyl and i-propyl, $R_2$ represents an iodo and $R_3$ represents hydrogen.

4. The compound of claim 1, wherein W represents a sulfur atom, $R_1$ represents a lower alkyl group, $R_2$ represents an alkynyl group and $R_3$ represents hydrogen.

5. The compound of claim 4, wherein W represents a sulfur atom, $R_1$ represents a lower alkyl selected from the group consisting of methyl, ethyl, n-propyl and i-propyl, $R_2$ represents 1-hexynyl and $R_3$ represents hydrogen.

6. The compound of claim 1, wherein W represents a sulfur atom, $R_1$ represents a lower alkyl, $R_2$ represents alkylidenehydrazino and $R_3$ represents hydrogen.

7. The compound of claim 6, wherein W represents a sulfur atom, $R_1$ represents a lower alkyl selected from the group consisting of methyl, ethyl, n-propyl and i-propyl, $R_2$ represents N'-3-methyl-1-butylidenehydrazino and $R_3$ represents hydrogen.

8. The compound of claim 1, wherein W represents an oxygen atom, $R_1$ represents a lower alkyl, $R_2$ represents a halogen atom and $R_3$ represents a substituent selected from the group consisting of hydrogen, cycloalkyl, substituted (ar)alkyl and unsubstituted (ar)alkyl.

9. The compound of claim 1, wherein W represents an oxygen atom, $R_1$ represents methyl, ethyl or cyclopropyl, $R_2$ represents chloro, and $R_3$ represents hydrogen, cyclopentyl or halobenzyl.

10. The compound of claim 9, wherein said halobenzyl is 3-iodobenzyl.

11. The compound of claim 1, which is selected from the following compounds:
5'-deoxy-2-iodo-5'methylthioadenosine;
5'-deoxy-2-iodo-5'-ethylthioadenosine;
5'-deoxy-2-iodo-5'-propylthioadenosine;
5'-deoxy-2-iodo-5'-isopropylthioadenosine;
5'-deoxy-2-(1-hexynyl)-5'-methylthioadenosine;
5'-deoxy-2-(1-hexynyl)-5'-ethylthioadenosine;
5'-deoxy-2-(1-hexynyl)-5'-propylthioadenosine;
5'-deoxy-2-(1-hexynyl)-5'-isopropylthioadenosine;
5'-deoxy-2-(N'-3-methyl-1-butylidenehydrazino)-5'-methylthioadenosine;
5'-deoxy-5'-ethylthio-2-(N'-3-methyl-1-butylidenehydrazino) adenosine;
5'-deoxy-2-(N'-3-methyl-1-butylidenehydrazino)-5'-propylthioadenosine;
5'-deoxy-2-(N'-3-methyl-1-butylidenehydrazino)-5'-isopropylthioadenosine;
2-chloro-5'-O-methyladenosine;
$N^6$-cyclopentyl-2-chloro-5'-O-methyladenosine;
2-chloro-5'-O-methyladenosine;
2-chloro-5'-O-ethyladenosine;
$N^6$-cyclopentyl-2-chloro-5'-O-ethyladenosine;
$N^6$-(3-iodobenzyl)-2-chloro-5'-O-ethyladenosine;
2-chloro-5'-O-cyclopropyladenosine;
$N^6$-cyclopentyl-2-chloro-5'-O-cyclopropyladenosine; and
$N^6$-(3-iodobenzyl)-2-chloro-5'-O-cyclopropyladenosine.

12. A pharmaceutical composition comprising as an active ingredient a compound of general formula (I):

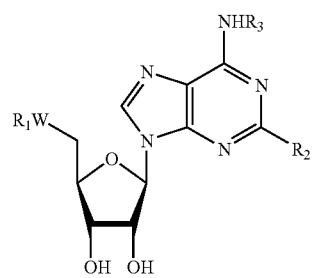

wherein
W represents an oxygen atom or a sulfur atom;
$R_1$ represents lower alkyl or lower cycloalkyl;
$R_2$ represents halogen, alkenyl, alkynyl or alkylidenehydrazino,
$R_3$ represents hydrogen, lower alkyl, lower cycloalkyl, aryl, (ar)alkyl or anilide, wherein said cycloalkyl, aryl and (ar)alkyl may be substituted with one or more of the groups selected from halogen, hydroxyl and hydroxyalkyl; or a pharmaceutically acceptable salt thereof; in combination with pharmaceutically acceptable additive,
wherein when W is a sulfur atom, $R_1$ is a lower alkyl, $R_2$ is a halogen and $R_3$ is a hydrogen, then $R_2$ is iodo.

13. The composition of claim 12, wherein said active ingredient is a compound of formula (I) in which W represents a sulfur atom, $R_1$ represents lower alkyl, $R_2$ represents an iodo and $R_3$ represents hydrogen.

14. The composition of claim 13, wherein said active ingredient is a compound of formula (I) in which W represents a sulfur atom, $R_1$ represents a lower alkyl selected from the group consisting of methyl, ethyl, n-propyl and i-propyl, $R_2$ represents an iodo atom and $R_3$ represents hydrogen.

15. The composition of claim 12, wherein said active ingredient is a compound of formula (I) in which W represent a sulfur atom, $R_1$ represents a lower alkyl group, $R_2$ represents an alkynyl group and $R_3$ represents hydrogen.

16. The composition of claim 15, wherein said active ingredient is a compound of formula (I) in which W represents a sulfur atom, $R_1$ represents a lower alkyl selected from the group consisting of methyl, ethyl, n-propyl and i-propyl, $R_2$ represents 1-hexynyl and $R_3$ represents hydrogen.

17. The composition of claim 12, wherein said active ingredient is a compound of formula (I) in which W represents a sulfur atom, $R_1$ represents a lower alkyl, $R_2$ represents alkylidenehydrazino and $R_3$ represents hydrogen.

18. The composition of claim 17, wherein said active ingredient is a compound of formula (I) in which W represents a sulfur atom, $R_1$ represents a lower alkyl selected from the group consisting of methyl, ethyl, n-propyl and i-propyl, $R_2$ represents N'-3-methyl-1-butylidenehydrazino and $R_3$ represents hydrogen.

19. The composition of claim 12, wherein said active ingredient is a compound of formula (I) in which W represents an oxygen atom, $R_1$ represents a lower alkyl, $R_2$ represents a halogen atom and $R_3$ represents a substituent selected from the group consisting of hydrogen, cycloalkyl, substituted (ar)alkyl and a unsubstituted (ar)alkyl.

20. The composition of claim 12, wherein said active ingredient is a compound of formula (I) in which W represents an oxygen atom, $R_1$ represents a methyl, ethyl or a cyclopropyl, $R_2$ represents a chlorine atom, and $R_3$ represents hydrogen, cyclopentyl or halobenzyl.

21. The composition of claim 20, wherein said halobenzyl is 3-iodobenzyl.

22. The composition of claim 12, wherein said active ingredient is selected from the following compounds:
   5'-deoxy-2-iodo-5'-methylthioadenosine;
   5'-deoxy-2-iodo-5'-ethylthio-adenosine;
   5'-deoxy-2-iodo-5'-propylthioadenosine;
   5'-deoxy-2-iodo-5'-isopropylthioadenosine;
   5'-deoxy-2-(1-hexynyl)-5'-methylthioadenosine;
   5'-deoxy-2-(1-hexynyl) 5'-ethylthioadenosine;
   5'-deoxy-2-(1-hexynyl)-5'-propylthioadenosine;
   5'-deoxy-2-(1hexynyl)-5'-isopropylthioadenosine;
   5'-deoxy-2-(N'-3-methyl-1-butylidenehydrazino)-5'-methylthioadenosine;
   5'-deoxy-2-(N'-3-methyl-1-butylidenehydrazino)-5'-ethylthioadenosine;
   5'-deoxy-2-(N'-3-methyl-1-butylidenehydrazino)-5'-propylthioadenosine;
   5'-deoxy-2-(N'-3-methyl-1-butylidenehydrazino)-5'-isopropthioadenosine;
   2-chloro-5'-O-ethyladenosine;
   $N^6$-cyclopentyl-2-chloro-5'-O-ethyladenosine;
   $N^6$-(3-iodobenzyl)-2-chloro-5'-O-ethyladenosine;
   2-chloro-5'-O-cyclopropyladenosine;
   $N^6$-cyclopentyl-2-chloro-5'-O-cyclopropyladenosine; and
   $N^6$-(3-iodobenzyl)-2-chloro-5'-O-cyclopropyladenosine.

23. A method for inhibition of adenylate cyclase via the binding of an adenosine receptor agonist to adenosine $A_1$ and/or $A_3$ receptors or the stimulation of adenylate cyclase via binding of an adenosine receptor agonist to adenosine $A_{2A}$ and/or $A_{2B}$ receptors, comprising administering to a subject in need thereof an effective amount of a pharmaceutical composition comprising a compound of the following general formula (I):

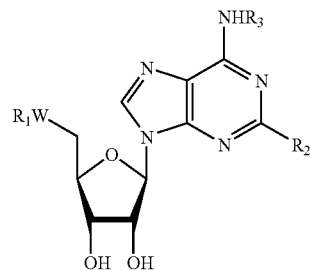

wherein
W represents an oxygen atom or a sulfur atom;
$R_1$ represents lower alkyl or lower cycloalkyl;
$R_2$ represents halogen, lower alkenyl, lower alkynyl or lower alkylidenehydrazino;
$R_3$ represents hydrogen, lower alkyl, lower cycloalkyl, (ar)alkyl, aryl or anilide; wherein said cycloalkyl aryl and (ar)alkyl may be substituted with one or more substituents selected from halogen, hydroxyl, and hydroxyalkyl;
or a pharmaceutically acceptable salt of said compound, wherein when W is a sulfur atom, $R_1$ is a lower alkyl, $R_2$ is a halogen and $R_3$ is hydrogen, then $R_2$ is iodo.

24. A compound of the general formula (I):

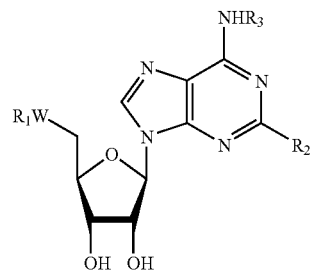

wherein
W represents an oxygen atom;
$R_1$ represents lower alkyl or lower cycloalkyl;
$R_2$ represents hydrogen, halogen, lower alkenyl, lower alkynyl or lower alkylidenehydrazino;
$R_3$ represents lower alkyl, lower cycloalkyl, (ar)alkyl, aryl or anilide; wherein said cycloalkyl, aryl and (ar)alkyl may be substituted with one or more substituents selected from halogen, hydroxyl, and hydroxyalkyl;
or a salt of said compound.

25. The compound of claim 24, wherein $R_1$ represents a lower alkyl, $R_2$ represents hydrogen and $R_3$ represents a lower cycloalkyl or (ar)alkyl; wherein said (ar)alkyl may be substituted with halogen.

26. The compound of claim 24, which is selected from the following compounds:
   $N^6$-cyclopentyl-5'-O-methyladenosine;
   $N^6$-(3-iodobenzyl)-5'-O-methyladenosine;
   $N^6$-cyclopentyl-5'-O-ethyladenosine;
   $N^6$-(3-iodobenzyl)-5'-O-ethyladenosine;
   $N^6$-cyclopentyl-5'-O-cyclopropyladenosine; and
   $N^6$-(3-iodobenzyl)-5'-O-cyclopropyladenosine.

27. A pharmaceutical composition comprising as active ingredient a compound of general formula (I):

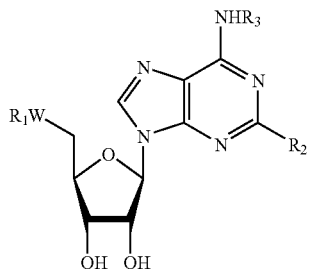

wherein:
W represents an oxygen atom;
$R_1$ represents lower alkyl or lower cycloalkyl;
$R_2$ represents hydrogen, halogen, lower alkenyl, lower alkynyl or lower alkylidenehydrazino;
$R_3$ represents lower alkyl, lower cycloalkyl, (ar)alkyl, aryl or anilide; wherein said cycloalkyl, aryl and (ar)alkyl may be substituted with one or more substituent selected from halogen, hydroxyl, and hydroxyalkyl;
or a pharmaceutically acceptable salt of said compound.

28. The composition of claim 27, wherein $R_1$ represents a lower alkyl, $R_2$ represents hydrogen and $R_3$ represents a lower cycloalkyl or (ar)alkyl; wherein said (ar)alkyl may be substituted with halogen.

29. The composition of claim 27, wherein said active ingredient is selected from the following compounds:
$N^6$-cyclopentyl-5'-O-methyladenosine;
$N^6$-(3-iodobenzyl)-5'-O-methyladenosine;
$N^6$-cyclopentyl-5'-O-ethyladenosine;
$N^6$-(3-iodobenzyl)-5'-O-ethyladenosine;
$N^6$-cyclopentyl-5'-O-cyclopropyladenosine; and
$N^6$-(3-iodobenzyl)-5'-O-cyclopropyladenosine.

* * * * *